US010815289B2

(12) United States Patent
Asaoka et al.

(10) Patent No.: US 10,815,289 B2
(45) Date of Patent: Oct. 27, 2020

(54) FC-BINDING PROTEIN, METHOD FOR PRODUCING SAID PROTEIN, ANTIBODY ADSORBENT USING SAID PROTEIN, AND METHOD FOR SEPARATING ANTIBODY USING SAID ADSORBENT

(71) Applicant: TOSOH CORPORATION, Yamaguchi (JP)

(72) Inventors: Yoshiharu Asaoka, Kanagawa (JP); Toru Tanaka, Kanagawa (JP); Yosuke Terao, Kanagawa (JP); Naoki Yamanaka, Kanagawa (JP); Natsuko Kizu, Kanagawa (JP); Masaru Aoki, Kanagawa (JP); Teruhiko Ide, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 474 days.

(21) Appl. No.: 15/321,916

(22) PCT Filed: Jun. 24, 2015

(86) PCT No.: PCT/JP2015/068259
§ 371 (c)(1),
(2) Date: Dec. 23, 2016

(87) PCT Pub. No.: WO2015/199154
PCT Pub. Date: Dec. 30, 2015

(65) Prior Publication Data
US 2017/0218044 A1  Aug. 3, 2017
US 2019/0211077 A2  Jul. 11, 2019

(30) Foreign Application Priority Data

Jun. 27, 2014 (JP) ................. 2014-133181
Jul. 17, 2014 (JP) ................. 2014-147206
Jul. 17, 2014 (JP) ................. 2014-147207
Dec. 25, 2014 (JP) ................. 2014-263407
Mar. 10, 2015 (JP) ................. 2015-047462
Jun. 5, 2015 (JP) ................. 2015-115078

(51) Int. Cl.
| | |
|---|---|
| C07K 1/00 | (2006.01) |
| C07H 21/02 | (2006.01) |
| C07H 21/04 | (2006.01) |
| C12P 21/06 | (2006.01) |
| C12N 1/20 | (2006.01) |
| C12N 5/00 | (2006.01) |
| C07K 16/00 | (2006.01) |
| C07K 14/735 | (2006.01) |
| C07K 1/22 | (2006.01) |
| C12P 21/02 | (2006.01) |
| C12N 15/09 | (2006.01) |
| C07K 16/06 | (2006.01) |
| B01D 15/38 | (2006.01) |
| B01J 20/281 | (2006.01) |
| G01N 33/68 | (2006.01) |
| G01N 30/00 | (2006.01) |

(52) U.S. Cl.
CPC .... C07K 14/70535 (2013.01); B01D 15/3809 (2013.01); C07K 1/22 (2013.01); C07K 16/00 (2013.01); C07K 16/065 (2013.01); C12N 15/09 (2013.01); C12P 21/02 (2013.01); G01N 30/482 (2013.01); G01N 33/6854 (2013.01); C07K 2317/10 (2013.01); C07K 2317/41 (2013.01); C07K 2317/732 (2013.01); G01N 2030/486 (2013.01); G01N 2400/02 (2013.01)

(58) Field of Classification Search
None
See application file for complete search history.

(56) References Cited

U.S. PATENT DOCUMENTS

| | | | |
|---|---|---|---|
| 5,998,166 A | 12/1999 | Luo | |
| 8,313,913 B2 * | 11/2012 | Nakamura | ........... A61K 39/395 435/7.1 |

(Continued)

FOREIGN PATENT DOCUMENTS

| | | |
|---|---|---|
| JP | 11-511649 | 10/1999 |
| JP | 2002-531086 | 9/2002 |

(Continued)

OTHER PUBLICATIONS

G. Zou et al., "Chemoenzymatic Synthesis and Fcγ Receptor Binding of Homogeneous Glycoforms of Antibody Fc Domain. Presence of a Bisecting Sugar Moiety Enhances the Affinity of Fc to FcγIIIa Receptor", Journal of the American Chemical Society, 2011, pp. 18975-19881, vol. 133.

(Continued)

*Primary Examiner* — Chun W Dahle
(74) *Attorney, Agent, or Firm* — Greenblum & Bernstein, P.L.C.

(57) ABSTRACT

Provided are: an Fc-binding protein having improved stability, particularly to heat and acid; a method for producing the protein; an antibody adsorbent using the protein; and a method for separating the antibodies using the adsorbent. Specifically provided are: an Fc-binding protein having improved stability to heat and acid, achieved by substituting an amino-acid residue in a specific position in the extracellular region of human FcγRIIIa with another specific amino acid; a method for producing the protein; an antibody adsorbent using the protein; and a method for separating the antibodies using the adsorbent.

8 Claims, 8 Drawing Sheets
Specification includes a Sequence Listing.

(56) References Cited

U.S. PATENT DOCUMENTS

| | | |
|---|---|---|
| 2007/0207163 A1 | 9/2007 | Sondermann et al. |
| 2013/0079499 A1 | 3/2013 | Hatayama et al. |
| 2017/0218044 A1* | 8/2017 | Asaoka .................. C07K 16/00 |

FOREIGN PATENT DOCUMENTS

| | | | |
|---|---|---|---|
| WO | WO-8911490 A1 * | 11/1989 | ....... C07K 14/70535 |
| WO | 2011/111393 | 9/2011 | |
| WO | 2013/120929 | 8/2013 | |
| WO | 2015/041303 | 3/2015 | |

OTHER PUBLICATIONS

K. Rogers et al., "IgG Fc Receptor III Homologues in Nonhuman Primate Species: Genetic Characterization and Ligand Interactions", The Journal of Immunology, 2006, pp. 3848-3856, vol. 177.

T. Takai, "Role of Fcγ receptors in immune regulation and diseases", Jpn. J. Clin. Immunol., 2005, pp. 318-326, vol. 28, including an english language summary.

J. Galon et al., "Affinity of the interaction between Fc gamma receptor type III (FCγRIII) and monomeric human IgG subclasses. Role of FCγRIII glycosylation", Eur. J. Immunol., 1997, pp. 1928-1932, vol. 27.

N. Takahashi, "Three-dimensional mapping of N-linked oligosaccharides using anion-exchange, hydrophobic and hydrophilic interaction modes of high-performance liquid chromotography", Journal of Chromatography A, 1996, pp. 217-225, vol. 720.

T. Schlothauer et al., "Analytical FcRn affinity chromotography for functional characterization of monoclonal antibodies", mAbs, 2013, pp. 576-586, vol. 5(4).

T. Shinkawa, "The Absence of Fucose but Not the Presence of Galactose or Bisecting N-Acetylglucosamine of Human IgG1 Complex-type Oligosaccharides Shows the Critical Role of Enchancing Antibody-dependent Cellular Cytotoxicity", J. Biol. Chem., 2003, pp. 3466-3473, vol. 278.

Search Report issued in International Bureau of WIPO Patent Application No. PCT/JP2015/068259, dated Sep. 29, 2015.

XP002776987, "Human IgG Fc gamma receptor IIIB extracellular domain protein, SEQ ID: 13", Retrieved from EBI accession No. GSP: AXU 36851, dated Mar. 18, 2010.

* cited by examiner

FIG. 4

| | Predicted glycan chain structure |
|---|---|
| N1 | Manα1-6<br>    Manα1-3 ⟶ Manα1-6<br>                 Manβ1-4GlcNAcβ1-4GlcNAc-PA<br>             Manα1-3 |
| N2 | GlcNAcβ1-2Manα1-6<br>                 Manβ1-4GlcNAcβ1-4GlcNAc-PA<br>GlcNAcβ1-2Manα1-3 |
| N3 | GlcNAcβ1-2Manα1-6        Fucα1-6<br>                 Manβ1-4GlcNAcβ1-4GlcNAc-PA<br>GlcNAcβ1-2Manα1-3 |
| N4 | Galβ1-4GlcNAcβ1-2Manα1-6    Fucα1-6<br>                       Manβ1-4GlcNAcβ1-4GlcNAc-PA<br>     GlcNAcβ1-2Manα1-3 |
| N5 | GlcNAcβ1-2Manα1-6        Fucα1-6<br>                 Manβ1-4GlcNAcβ1-4GlcNAc-PA<br>Galβ1-4GlcNAcβ1-2Manα1-3 |
| N6 | Galβ1-4GlcNAcβ1-2Manα1-6    Fucα1-6<br>                       Manβ1-4GlcNAcβ1-4GlcNAc-PA<br>Galβ1-4GlcNAcβ1-2Manα1-3 |
| M1 |                  GlcNAcβ1-2Manα1-6    Fucα1-6<br>                                   Manβ1-4GlcNAcβ1-4GlcNAc-PA<br>NeuSAcα2-3Galβ1-4GlcNAcβ1-2Manα1-3 |
| M2 |                Galβ1-4GlcNAcβ1-2Manα1-6    Fucα1-6<br>                                       Manβ1-4GlcNAcβ1-4GlcNAc-PA<br>NeuSAcα2-3Galβ1-4GlcNAcβ1-2Manα1-3 |
| D1 | NeuSAcα2-3Galβ1-4GlcNAcβ1-2Manα1-6    Fucα1-6<br>                                              Manβ1-4GlcNAcβ1-4GlcNAc-PA<br>NeuSAcα2-3Galβ1-4GlcNAcβ1-2Manα1-3 |

SEQUENCE LISTING

```
<160> NUMBER OF SEQ ID NOS: 107

<210> SEQ ID NO 1
<211> LENGTH: 254
<212> TYPE: PRT
<213> ORGANISM: Homo sapiens

<400> SEQUENCE: 1

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 2
<211> LENGTH: 528
<212> TYPE: DNA
<213> ORGANISM: Artificial Sequence
```

```
<220> FEATURE:
<223> OTHER INFORMATION: Description of Artificial Sequence: Synthetic
      polynucleotide encoding Fc gammma IIIa (E. coli codon)

<400> SEQUENCE: 2
ggcatgcgta ccgaagatct gccgaaagcg gtggtgtttc tggaaccgca gtggtatcgc      60
gtgctggaga aagattctgt gacccttaaa tgccagggcg cgtatagccc ggaagataac     120
agcacccagt ggttccacaa tgaaagcctg atttccagcc aggcgagcag ctactttatt     180
gatgcggcga cggtggatga tagcggcgaa tatcgttgcc agaccaacct gagcaccctg     240
agcgatccgg tgcagctgga ggtgcacatc gggtggcttc tgttacaggc tccacggtgg     300
gtgttcaaag aggaggatcc gattcatctg cggtgtcact cctggaagaa taccgccctg     360
cataaagtga cctacctgca aacggcaagg ggccgcaagt atttccacca caactccgac     420
ttctatattc ccaaagcgac gctgaaggac agcggcagct atttctgccg tgggctggtg     480
ggcagcaaaa atgtgagcag cgagaccgtg aatattacca ttacccaa                   528

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcatgcgta ccgaagatct gccgaaagcg gtggtgtttc t                          41

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tctccagcac gcgataccac tgcggttcca gaaacaccac cgctttcg                   48

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggtatcgcgt gctggagaaa gattctgtga cccttaaatg ccagggcg                   48

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
actgggtgct gttatcttcc gggctatacg cgccctggca tttaaggg                   48

<210> SEQ ID NO 7
<211> LENGTH: 48
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggaagataac agcacccagt ggttccacaa tgaaagcctg atttccag                        48

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
catcaataaa gtagctgctc gcctggctgg aaatcaggct ttcattgt                        48

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcgagcagct actttattga tgcggcgacg gtggatgata gcggcgaa                        48

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cagggtgctc aggttggtct ggcaacgata ttcgccgcta tcatccac                        48

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
accaacctga gcaccctgag cgatccggtg cagctggagg tgcacatc                        48

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ccaccgtgga gcctgtaaca gaagccaccc gatgtgcacc tccagctg                        48

<210> SEQ ID NO 13
<211> LENGTH: 48
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 13
tacaggctcc acggtgggtg ttcaaagagg aggatccgat tcatctgc                    48

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agggcggtat tcttccagga gtgacaccgc agatgaatcg gatcctcc                    48

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cctggaagaa taccgccctg cataaagtga cctacctgca aaacggca                    48

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cggagttgtg gtggaaatac ttgcggccct tgccgttttg caggtagg                    48

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agtatttcca ccacaactcc gacttctata ttcccaaagc gacgctga                    48

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agcccacggc agaaatagct gccgctgtcc ttcagcgtcg ctttggga                    48

<210> SEQ ID NO 19
<211> LENGTH: 48
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 19
ctatttctgc cgtgggctgg tgggcagcaa aaatgtgagc agcgagac                    48

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttgggtaatg gtaatattca cggtctcgct gctcacattt ttg                        43

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tagccatggg catgcgtacc gaagatctgc cgaaagc                               37

<210> SEQ ID NO 22
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cccaagctta atgatgatga tgatgatggc cccttgggt aatggtaata ttcacggtct       60
cgctgc                                                                 66

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
taatacgact cactataggg                                                  20

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tatgctagtt attgctcag                                                   19

<210> SEQ ID NO 25
<211> LENGTH: 216
<212> TYPE: PRT
```

<210> SEQ ID NO 25
<211> LENGTH: 216
<212> TYPE: PRT
<213> ORGANISM: Artificial Sequence
<220> FEATURE:
<223> OTHER INFORMATION: Description of Artificial Sequence: Synthetic pET-CD16 polypeptide

<400> SEQUENCE: 25

```
Met Lys Ile Lys Thr Gly Ala Arg Ile Leu Ala Leu Ser Ala Leu Thr
1               5                   10                  15
Thr Met Met Phe Ser Ala Ser Ala Leu Ala Lys Ile Glu Glu Ala Met
                20                  25                  30
Gly Met Arg Thr Glu Asp Leu Pro Lys Ala Val Val Phe Leu Glu Pro
            35                  40                  45
Gln Trp Tyr Arg Val Leu Glu Lys Asp Ser Val Thr Leu Lys Cys Gln
    50                  55                  60
Gly Ala Tyr Ser Pro Glu Asp Asn Ser Thr Gln Trp Phe His Asn Glu
65                  70                  75                  80
Ser Leu Ile Ser Ser Gln Ala Ser Ser Tyr Phe Ile Asp Ala Ala Thr
                85                  90                  95
Val Asp Asp Ser Gly Glu Tyr Arg Cys Gln Thr Asn Leu Ser Thr Leu
            100                 105                 110
Ser Asp Pro Val Gln Leu Glu Val His Ile Gly Trp Leu Leu Leu Gln
        115                 120                 125
Ala Pro Arg Trp Val Phe Lys Glu Glu Asp Pro Ile His Leu Arg Cys
130                 135                 140
His Ser Trp Lys Asn Thr Ala Leu His Lys Val Thr Tyr Leu Gln Asn
145                 150                 155                 160
Gly Lys Gly Arg Lys Tyr Phe His His Asn Ser Asp Phe Tyr Ile Pro
                165                 170                 175
Lys Ala Thr Leu Lys Asp Ser Gly Ser Tyr Phe Cys Arg Gly Leu Val
            180                 185                 190
Gly Ser Lys Asn Val Ser Ser Glu Thr Val Asn Ile Thr Ile Thr Gln
        195                 200                 205
Gly Gly His His His His His His
    210                 215
```

<210> SEQ ID NO 26
<211> LENGTH: 648
<212> TYPE: DNA
<213> ORGANISM: Artificial Sequence
<220> FEATURE:
<223> OTHER INFORMATION: Description of Artificial Sequence: Synthetic pET-CD16 polynucleotide

<400> SEQUENCE: 26

```
atgaaaataa aaacaggtgc acgcatcctc gcattatccg cattaacgac gatgatgttt    60
tccgcctcgg ctctcgccaa atcgaagaa gccatgggca tgcgtaccga agatctgccg    120
aaagcggtgg tgtttctgga accgcagtgg tatcgcgtgc tggagaaaga ttctgtgacc    180
cttaaatgcc agggcgcgta tagcccggaa gataacagca cccagtggtt ccacaatgaa    240
agcctgattt ccagccaggc gagcagctac tttattgatg cggcgacggt ggatgatagc    300
ggcgaatatc gttgccagac caacctgagc accctgagcg atccggtgca gctggaggtg    360
cacatcgggt ggcttctgtt acaggctcca cggtgggtgt tcaaagagga ggatccgatt    420
catctgcggt gtcactcctg gaagaatacc gccctgcata agtgaccta cctgcaaaac    480 ggcaagggcc gcaagtattt ccaccacaac tccgacttct atattcccaa agcgacgctg    540
aaggacagcg gcagctattt ctgccgtggg ctggtgggca gcaaaaatgt gagcagcgag    600
```
accgtgaata ttaccattac ccaaggggc catcatcatc atcatcat                648

<210> SEQ ID NO 27
<211> LENGTH: 216
<212> TYPE: PRT
<213> ORGANISM: Artificial Sequence
<220> FEATURE:
<223> OTHER INFORMATION: Description of Artificial Sequence: Synthetic
      FcR2 polypeptide

<400> SEQUENCE: 27

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Phe Leu Glu Pro
        35                  40                  45

Gln Trp Asn Arg Val Leu Glu Lys Asp Ser Val Thr Leu Lys Cys Gln
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Phe Ile Asp Ala Ala Thr
                85                  90                  95

Val Asp Asp Ser Gly Glu Tyr Arg Cys Gln Thr Asn Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Glu Glu Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215
```

<210> SEQ ID NO 28
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide encoding FcR2

<400> SEQUENCE: 28
atgaaaataa aaacaggtgc acgcatcctc gcattatccg cattaacgac gatgatgttt    60
tccgcctcgg ctctcgccaa aatcgaagaa gccatgggca tgcgtaccga agatctgccg   120
aaagcggagg tgtttctgga accgcagtgg aatcgcgtgc tggagaaaga ttctgtgacc   180
cttaaatgcc agggcgcgta tagcccggaa gataacagca cccagtggtt ccacaatgaa   240
agcctgattt ccagccaggc gagcagctac tttattgatg cggcgaccgt ggatgatagc   300
ggcgaatatc gttgccagac caacctgagc accctgagcg atccggtgca gctggaggtg   360

```
cacatcgggt ggcttctgtt acaggctcca cggtgggtgt tcaaagagga ggatccgatt    420
catctgcggt gtcactcctg gaagaatacc gccctgcata aagtgaccta cctgcaaaac    480
ggcaagggcc gcaagtattt ccaccataac tccgacttct atattcccaa agcgacgctg    540
aaggacagcg gcagctattt ctgccgtggg ctggtgggca gcaaaaatgt gagcagcgag    600
accgtgaata ttaccattac ccaagggggc catcatcatc atcatcat                 648
```

```
<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agccaggcga gcagctacct tattgatgcg                                      30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ccaccgtcgc cgcatcaata aggtagctgc                                      30

<210> SEQ ID NO 31
<211> LENGTH: 216
<212> TYPE: PRT
<213> ORGANISM: Artificial Sequence
<220> FEATURE:
<223> OTHER INFORMATION: Description of Artificial Sequence: Synthetic
      FcR3 polypeptide

<400> SEQUENCE: 31
```

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Phe Leu Glu Pro
        35                  40                  45

Gln Trp Asn Arg Val Leu Glu Lys Asp Ser Val Thr Leu Lys Cys Gln
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Asn Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Glu Glu Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
        210                 215

<210> SEQ ID NO 32
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide encoding FcR3

<400> SEQUENCE: 32
atgaaaataa aaacaggtgc acgcatcctc gcattatccg cattaacgac gatgatgttt     60
tccgcctcgg ctctcgccaa aatcgaagaa gccatgggca tgcgtaccga agatctgccg    120
aaagcggagg tgtttctgga accgcagtgg aatcgcgtgc tggagaaaga ttctgtgacc    180
cttaaatgcc agggcgcgta tagcccggaa gataacagca cccagtggtt ccacaatgaa    240
agcctgattt ccagccaggc gagcagctac cttattgatg cggcgacggt ggatgatagc    300
ggcgaatatc gttgccagac caacctgagc accctgagcg atccggtgca gctggaggtg    360
cacatcgggt ggcttctgtt acaggctcca cggtgggtgt tcaaagagga ggatccgatt    420
catctgcggt gtcactcctg gaagaatacc gccctgcata agtgaccta cctgcaaaac    480 ggcaagggcc gcaagtattt ccaccataac tccgacttct atattcccaa agcgacgctg    540
aaggacagcg gcagctattt ctgccgtggg ctggtgggca gcaaaaatgt gagcagcgag    600
accgtgaata ttaccattac ccaagggggc catcatcatc atcatcat              648

<210> SEQ ID NO 33
<211> LENGTH: 216
<212> TYPE: PRT
<213> ORGANISM: Artificial Sequence
<220> FEATURE:
<223> OTHER INFORMATION: Description of Artificial Sequence: Synthetic
      FcR4 polypeptide

<400> SEQUENCE: 33

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Phe Leu Glu Pro
        35                  40                  45

Gln Trp Asn Arg Val Leu Glu Lys Asp Ser Val Thr Leu Lys Cys Gln
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Asn Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Glu Gly Asp Pro Ile His Leu Arg Cys

```
                130                 135                 140
His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215

<210> SEQ ID NO 34
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide encoding FcR4

<400> SEQUENCE: 34
atgaaaataa aaacaggtgc acgcatcctc gcattatccg cattaacgac gatgatgttt      60
tccgcctcgg ctctcgccaa aatcgaagaa gccatgggca tgcgtaccga agatctgccg     120
aaagcggagg tgtttctgga accgcagtgg aatcgcgtgc tggagaaaga ttctgtgacc     180
cttaaatgcc agggcgcgta tagcccggaa gataacagca cccagtggtt ccacaatgaa     240
agcctgattt ccagccaggc gagcagctac cttattgatg cggcgacggt ggatgatagc     300
ggcgaatatc gttgccagac caacctgagc accctgagcg atccggtgca gctggaggtg     360
cacatcgggt ggcttctgtt acaggctcca cggtgggtgt tcaaagaggg ggatccgatt     420
catctgcggt gtcactcctg gaagaatacc gccctgcata agtgaccta cctgcaaaac      480 ggcaagggcc gcaagtattt ccaccacaac tccgacttct atattcccaa agcgacgctg     540
aaggacagcg gcagctattt ctgccgtggg ctggtgggca gcaaaaatgt gagcagcgag     600
accgtgaata ttaccattac ccaagggggc catcatcatc atcatcat                  648

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gaatatcgtt gccagaccag cctgagcacc                                       30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gatcgctcag ggtgctcagg ctggtctggc                                       30

<210> SEQ ID NO 37
<211> LENGTH: 216
```

<212> TYPE: PRT
<213> ORGANISM: Artificial Sequence
<220> FEATURE:
<223> OTHER INFORMATION: Description of Artificial Sequence: Synthetic
      FcR5a polypeptide

<400> SEQUENCE: 37

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Phe Leu Glu Pro
        35                  40                  45

Gln Trp Asn Arg Val Leu Glu Lys Asp Ser Val Thr Leu Lys Cys Gln
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215

<210> SEQ ID NO 38
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide encoding FcR5a

<400> SEQUENCE: 38
atgaaaataa aaacaggtgc acgcatcctc gcattatccg cattaacgac gatgatgttt      60
tccgcctcgg ctctcgccaa atcgaagaa gccatgggca tgcgtaccga agatctgccg       120
aaagcggagg tgtttctgga accgcagtgg aatcgcgtgc tggagaaaga ttctgtgacc      180
cttaaatgcc agggcgcgta tagcccggaa gataacagca cccagtggtt ccacaatgaa      240
agcctgattt ccagccaggc gagcagctac cttattgatg cggcgacggt ggatgatagc      300
ggcgaatatc gttgccagac cagcctgagc accctgagcg atccggtgca gctggaggtg      360
cacatcgggt ggcttctgtt acaggctcca cggtgggtgt tcaaagaggg ggatccgatt      420
catctgcggt gtcactcctg gaagaatacc gccctgcata agtgacctac ctgcaaaac      480 ggcaagggcc gcaagtattt ccaccacaac tccgacttct atattcccaa agcgacgctg      540

```
aaggacagcg gcagctattt ctgccgtggg ctggtgggca gcaaaaatgt gagcagcgag    600
accgtgaata ttaccattac ccaagggggc catcatcatc atcatcat                 648
```

<210> SEQ ID NO 39
<211> LENGTH: 216
<212> TYPE: PRT
<213> ORGANISM: Artificial Sequence
<220> FEATURE:
<223> OTHER INFORMATION: Description of Artificial Sequence: Synthetic
    FcR7a polypeptide

<400> SEQUENCE: 39

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Met Arg Thr Glu Asp Leu Pro Lys Ala Glu Val Ile Leu Glu Pro
            35                  40                  45

Gln Trp Asn Arg Val Leu Glu Lys Asp Ser Val Thr Leu Lys Cys Gln
        50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
                100                 105                 110

Ser Asp Pro Val Gln Leu Glu Val His Ile Gly Trp Leu Leu Leu Gln
            115                 120                 125

Ala Pro Arg Trp Glu Phe Lys Glu Gly Asp Pro Ile His Leu Arg Cys
        130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
        210                 215

<210> SEQ ID NO 40
<211> LENGTH: 648
<212> TYPE: DNA
<213> ORGANISM: Artificial Sequence
<220> FEATURE:
<223> OTHER INFORMATION: Description of Artificial Sequence: Synthetic
    polynucleotide encoding FcR7a

<400> SEQUENCE: 40

```
atgaaaataa aaacaggtgc acgcatcctc gcattatccg cattaacgac gatgatgttt    60
tccgcctcgg ctctcgccaa aatcgaagaa gccatgggca tgcgtaccga agatctgccg    120
aaagcggagg tgattctgga accgcagtgg aatcgcgtgc tggagaaaga ttctgtgacc    180
cttaaatgcc agggcgcgta tagcccggaa gataacagca cccagtggtt ccacaatgaa    240
agcctgattt ccagccaggc gagcagctac cttattgatg cggcgacggt ggatgatagc    300
ggcgaatatc gttgccagac cagcctgagc accctgagcg atccggtgca gctggaggtg    360
```

```
cacatcggqt ggcttctgtt acaggctcca cggtgggagt tcaaagaggg ggatccgatt      420
catctgcggt gtcactcctg aagaatacc gccctgcata aagtgaccta cctgcaaaac      480
ggcaagggcc gcaagtattt ccaccacaac tccgacttct atattcccaa agcgacgctg      540
aaggacagcg gcagctattt ctgccgtggg ctggtgggca gcaaaaatgt gagcagcgag      600
accgtgaata ttaccattac ccaaggggc catcatcatc atcatcat                   648
```

```
<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
accagcccac ggcaggaata gctgccgctg                                       30

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gacagcggca gctattcctg ccgtgggctg                                       30

<210> SEQ ID NO 43
<211> LENGTH: 216
<212> TYPE: PRT
<213> ORGANISM: Artificial Sequence
<220> FEATURE:
<223> OTHER INFORMATION: Description of Artificial Sequence: Synthetic
      FcR8 polypeptide

<400> SEQUENCE: 43
```

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Met Arg Thr Glu Asp Leu Pro Lys Ala Glu Val Ile Leu Glu Pro
            35                  40                  45

Gln Trp Asn Arg Val Leu Glu Lys Asp Ser Val Thr Leu Lys Cys Gln
        50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro 165                 170                 175
Lys Ala Thr Leu Lys Asp Ser Gly Ser Tyr Ser Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
        210                 215

<210> SEQ ID NO 44
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide encoding FcR8

<400> SEQUENCE: 44
atgaaaataa aaacaggtgc acgcatcctc gcattatccg cattaacgac gatgatgttt    60
tccgcctcgg ctctcgccaa aatcgaagaa gccatgggca tgcgtaccga agatctgccg   120
aaagcggagg tgattctgga accgcagtgg aatcgcgtgc tggagaaaga ttctgtgacc   180
cttaaatgcc agggcgcgta tagcccggaa gataacagca cccagtggtt ccacaatgaa   240
agcctgattt ccagccaggc gagcagctac cttattgatg cggcgacggt ggatgatagc   300
ggcgaatatc gttgccagac cagcctgagc accctgagcg atccggtgca gctggaggtg   360
cacatcgggt ggcttctgtt acaggctcca cggtgggagt tcaagagggg ggatccgatt   420
catctgcggt gtcactcctg gaagaatacc gccctgcata agtgacccta cctgcaaaac   480
ggcaagggcc gcaagtattt ccaccacaac tccgacttct atattcccaa agcgacgctg   540
aaggacagcg gcagctattc ctgccgtggg ctggtgggca gcaaaaatgt gagcagcgag   600
accgtgaata ttaccattac ccaagggggc catcatcatc atcatcat                648

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 gtgacccta aatgccgggg cgcgtatagc                                      30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ccgggctata cgcgccccgg catttaaggg                                     30

<210> SEQ ID NO 47
<211> LENGTH: 216
<212> TYPE: PRT
<213> ORGANISM: Artificial Sequence
<220> FEATURE:
<223> OTHER INFORMATION: Description of Artificial Sequence: Synthetic
      FcR9 polypeptide

<400> SEQUENCE: 47

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Ile Leu Glu Pro
        35                  40                  45

Gln Trp Asn Arg Val Leu Glu Lys Asp Ser Val Thr Leu Lys Cys Arg
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215
```

<210> SEQ ID NO 48
<211> LENGTH: 648
<212> TYPE: DNA
<213> ORGANISM: Artificial Sequence
<220> FEATURE:
<223> OTHER INFORMATION: Description of Artificial Sequence: Synthetic polynucleotide encoding FcR9

<400> SEQUENCE: 48

```
atgaaaataa aaacaggtgc acgcatcctc gcattatccg cattaacgac gatgatgttt     60
tccgcctcgg ctctcgccaa aatcgaagaa gccatgggca tgcgtaccga agatctgccg    120
aaagcggagg tgattctgga accgcagtgg aatcgcgtgc tggagaaaga ttctgtgacc    180
cttaaatgcc ggggcgcgta tagcccggaa gataacagca cccagtggtt ccacaatgaa    240
agcctgattt ccagccaggc gagcagctac cttattgatg cggcgacggt ggatgatagc    300
ggcgaatatc gttgccagac cagcctgagc accctgagcg atccggtgca gctggaggtg    360
cacatcgggt ggcttctgtt acaggctcca cggtgggagt tcaaagaggg ggatccgatt    420
catctgcggt gtcactcctg gaagaatacc gccctgcata agtgacctaa cctgcaaaac    480
ggcaagggcc gcaagtattt ccaccacaac tccgacttct atattcccaa agcgacgctg    540
aaggacagcg gcagctattc ctgccgtggg ctggtgggca gcaaaaatgt gagcagcgag    600
accgtgaata ttaccattac ccaagggggc catcatcatc atcatcat                648
```

<210> SEQ ID NO 49

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tgccggggcg cgtctagccc ggaagataac                                         30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gctagacgcg ccccggcatt taagggtcac                                         30

<210> SEQ ID NO 51
<211> LENGTH: 216
<212> TYPE: PRT
<213> ORGANISM: Artificial Sequence
<220> FEATURE:
<223> OTHER INFORMATION: Description of Artificial Sequence: Synthetic
      FcR10 polypeptide

<400> SEQUENCE: 51

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Met Arg Thr Glu Asp Leu Pro Lys Ala Glu Val Ile Leu Glu Pro
            35                  40                  45

Gln Trp Asn Arg Val Leu Glu Lys Asp Ser Val Thr Leu Lys Cys Arg
    50                  55                  60

Gly Ala Ser Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215

<210> SEQ ID NO 52
```

<210> SEQ ID NO 52
<211> LENGTH: 648
<212> TYPE: DNA
<213> ORGANISM: Artificial Sequence
<220> FEATURE:
<223> OTHER INFORMATION: Description of Artificial Sequence: Synthetic polynucleotide encoding FcR10

<400> SEQUENCE: 52

```
atgaaaataa aaacaggtgc acgcatcctc gcattatccg cattaacgac gatgatgttt      60
tccgcctcgg ctctcgccaa aatcgaagaa gccatgggca tgcgtaccga agatctgccg     120
aaagcggagg tgattctgga accgcagtgg aatcgcgtgc tggagaaaga ttctgtgacc     180
cttaaatgcc ggggcgcgtc tagcccggaa gataacagca cccagtggtt ccacaatgaa     240
agcctgattt ccagccaggc gagcagctac cttattgatg cggcgacggt ggatgatagc     300
ggcgaatatc gttgccagac cagcctgagc accctgagcg atccggtgca gctggaggtg     360
cacatcgggt ggcttctgtt acaggctcca cggtgggagt tcaaagaggg ggatccgatt     420
catctgcggt gtcactcctg gaagaatacc gccctgcata agtgacctta cctgcaaaac     480
ggcaagggcc gcaagtattt ccaccacaac tccgacttct atattcccaa agcgacgctg     540
aaggacagcg gcagctattc ctgccgtggg ctggtgggca gcaaaaatgt gagcagcgag     600
accgtgaata taaccattac ccaaggggggc catcatcatc atcatcat               648
```

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53

```
ggcgaatatc gttgccggac cagcctgagc                                        30
```

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54

```
ggtgctcagg ctggtccggc aacgatattc                                        30
```

<210> SEQ ID NO 55
<211> LENGTH: 216
<212> TYPE: PRT
<213> ORGANISM: Artificial Sequence
<220> FEATURE:
<223> OTHER INFORMATION: Description of Artificial Sequence: Synthetic FcR11 polypeptide

<400> SEQUENCE: 55

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Ile Leu Glu Pro
        35                  40                  45

Gln Trp Asn Arg Val Leu Glu Lys Asp Ser Val Thr Leu Lys Cys Arg
    50                  55                  60
```

Gly Ala Ser Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
            85                  90                  95

Val Asp Asp Ser Gly Glu Tyr Arg Cys Arg Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215

<210> SEQ ID NO 56
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide encoding FcR11

<400> SEQUENCE: 56
atgaaaataa aaacaggtgc acgcatcctc gcattatccg cattaacgac gatgatgttt      60
tccgcctcgg ctctcgccaa aatcgaagaa gccatgggca tgcgtaccga agatctgccg     120
aaagcggagg tgattctgga accgcagtgg aatcgcgtgc tggagaaaga ttctgtgacc     180
cttaaatgcc ggggcgcgtc tagcccggaa gataacagca cccagtggtt ccacaatgaa     240
agcctgattt ccagccaggc gagcagctac cttattgatg cggcgacggt ggatgatagc     300
ggcgaatatc gttgccggac cagcctgagc accctgagcg atccggtgca gctggaggtg     360
cacatcgggt ggcttctgtt acaggctcca cggtgggagt tcaaagaggg ggatccgatt     420
catctgcggt gtcactcctg gaagaatacc gccctgcata agtgaccta cctgcaaaac      480 ggcaagggcc gcaagtattt ccaccacaac tccgacttct atattcccaa agcgacgctg     540
aaggacagcg gcagctattc ctgccgtggg ctggtgggca gcaaaaatgt gagcagcgag     600
accgtgaata ttaccattac ccaagggggc catcatcatc atcatcat                  648

<210> SEQ ID NO 57
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cccaagctta tccgcaggta tcgttgcggc acccttgggt aatggtaata ttcacggtct      60
cgctgc                                                                 66

<210> SEQ ID NO 58
<211> LENGTH: 216
<212> TYPE: PRT
<213> ORGANISM: Artificial Sequence
<220> FEATURE:
<223> OTHER INFORMATION: Description of Artificial Sequence: Synthetic
    FcR5aCys polypeptide

<400> SEQUENCE: 58

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Phe Leu Glu Pro
        35                  40                  45

Gln Trp Asn Arg Val Leu Glu Lys Asp Ser Val Thr Leu Lys Cys Gln
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Cys Arg Asn Asp Thr Cys Gly
    210                 215

<210> SEQ ID NO 59
<211> LENGTH: 648
<212> TYPE: DNA
<213> ORGANISM: Artificial Sequence
<220> FEATURE:
<223> OTHER INFORMATION: Description of Artificial Sequence: Synthetic
    polynucleotide encoding FcR5aCys

<400> SEQUENCE: 59
atgaaaataa aaacaggtgc acgcatcctc gcattatccg cattaacgac gatgatgttt      60
tccgcctcgg ctctcgccaa aatcgaagaa gccatgggca tgcgtaccga agatctgccg     120
aaagcggagg tgtttctgga accgcagtgg aatcgcgtgc tggagaaaga ttctgtgacc     180
cttaaatgcc agggcgcgta tagcccggaa gataacagca cccagtggtt ccacaatgaa     240
agcctgattt ccagccaggc gagcagctac cttattgatg cggcgacggt ggatgatagc     300
ggcgaatatc gttgccagac cagcctgagc accctgagcg atccggtgca gctggaggtg     360
cacatcgggt ggcttctgtt acaggctcca cggtgggtgt tcaaagaggg ggatccgatt     420
catctgcggt gtcactcctg gaagaatacc gccctgcata agtgacctac cctgcaaaac     480

```
ggcaagggcc gcaagtattt ccaccacaac tccgacttct atattcccaa agcgacgctg      540
aaggacagcg gcagctattt ctgccgtggg ctggtgggca gcaaaaatgt gagcagcgag      600
accgtgaata ttaccattac ccaagggtgc cgcaacgata cctgcgga                  648
```

<210> SEQ ID NO 60
<211> LENGTH: 216
<212> TYPE: PRT
<213> ORGANISM: Artificial Sequence
<220> FEATURE:
<223> OTHER INFORMATION: Description of Artificial Sequence: Synthetic
    FcR9Cys polypeptide

<400> SEQUENCE: 60

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Ile Leu Glu Pro
        35                  40                  45

Gln Trp Asn Arg Val Leu Glu Lys Asp Ser Val Thr Leu Lys Cys Arg
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Val
            180                 185                 190

Gly Ser Lys Asn Val Ser Ser Glu Thr Val Asn Ile Thr Ile Thr Gln
        195                 200                 205

Gly Cys Arg Asn Asp Thr Cys Gly
    210                 215
```

<210> SEQ ID NO 61
<211> LENGTH: 648
<212> TYPE: DNA
<213> ORGANISM: Artificial Sequence
<220> FEATURE:
<223> OTHER INFORMATION: Description of Artificial Sequence: Synthetic
    polynucleotide encoding FcR9Cys

<400> SEQUENCE: 61

```
atgaaaataa aaacaggtgc acgcatcctc gcattatccg cattaacgac gatgatgttt      60
tccgcctcgg ctctcgccaa aatcgaagaa gccatgggca tgcgtaccga agatctgccg      120
aaagcggagg tgattctgga accgcagtgg aatcgcgtgc tggagaaaga ttctgtgacc      180
cttaaatgcc ggggcgcgta tagcccggaa gataacagca cccagtggtt ccacaatgaa      240
```

```
agcctgattt ccagccaggc gagcagctac cttattgatg cggcgacggt ggatgatagc      300
ggcgaatatc gttgccagac cagcctgagc accctgagcg atccggtgca gctggaggtg      360
cacatcgggt ggcttctgtt acaggctcca cggtgggagt tcaaagaggg ggatccgatt      420
catctgcggt gtcactcctg gaagaatacc gccctgcata agtgaccta cctgcaaaac       480 ggcaagggcc gcaagtattt ccaccacaac tccgacttct atattcccaa agcgacgctg      540
aaggacagcg gcagctattc ctgccgtggg ctggtgggca gcaaaaatgt gagcagcgag      600
accgtgaata ttaccattac ccaagggtgc cgcaacgata cctgcgga                  648
```

<210> SEQ ID NO 62
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62

```
ctagccatgg gcatgcgtac cggagatatg ccgaaagcgg ag                          42
```

<210> SEQ ID NO 63
<211> LENGTH: 216
<212> TYPE: PRT
<213> ORGANISM: Artificial Sequence
<220> FEATURE:
<223> OTHER INFORMATION: Description of Artificial Sequence: Synthetic FcR12 polypeptide

<400> SEQUENCE: 63

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Gly Asp Met Pro Lys Ala Glu Val Ile Leu Glu Pro
        35                  40                  45

Pro Trp Asn Arg Val Leu Glu Lys Asp Ser Val Thr Leu Lys Cys Arg
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Val
            180                 185                 190

Gly Arg Lys Asn Val Ser Ser Glu Thr Val Asn Ile Thr Ile Thr Gln
        195                 200                 205

Gly Gly His His His His His His
    210                 215

<210> SEQ ID NO 64
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide encoding FcR12

<400> SEQUENCE: 64

```
atgaaaataa aaacaggtgc acgcatcctc gcattatccg cattaacgac gatgatgttt      60
tccgcctcgg ctctcgccaa atcgaagaa gccatgggca tgcgtaccgg agatatgccg      120
aaagcggagg tgattctgga accgccgtgg aatcgcgtgc tggagaaaga ttcagtgacc      180
cttaaatgcc ggggcgcgta tagcccgaa gataacagca cccagtggtt ccacaatgaa      240
agcctgattt ccagccaggc gagcagctac cttattgatg cggcgacggt ggatgatagc      300
ggcgaatatc gttgccagac cagcctgagc accctgagcg atccggtgca gctggaggtg      360
cacatcgggt ggcttctgtt acaggctcca cggtgggagt caaagaggg ggatccgatt      420
catctgcggt gtcactcctg gaagaatacc gccctgcata aagtgaccta cctgcaaaac      480
ggcaagggcc gcaagtattt ccaccacaac tccgacttct atattcccaa agcgacgctg      540
aaggacagcg gcagctattc ctgccgtggg ctggtgggca gaaaaaatgt gagcagcgag      600
accgtgaata ttaccattac ccaaggggc catcatcatc atcatcat                    648
```

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65

```
cacaatgaaa gcctgattcc cagccaggcg                                        30
```

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66

```
gtagctgctc gcctggctgg gaatcaggct                                        30
```

<210> SEQ ID NO 67
<211> LENGTH: 216
<212> TYPE: PRT
<213> ORGANISM: Artificial Sequence
<220> FEATURE:
<223> OTHER INFORMATION: Description of Artificial Sequence: Synthetic
      FcR13 polypeptide

<400> SEQUENCE: 67

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Gly Asp Met Pro Lys Ala Glu Val Ile Leu Glu Pro
        35                  40                  45
```

```
Pro Trp Asn Arg Val Leu Glu Lys Asp Ser Val Thr Leu Lys Cys Arg
 50                  55                  60

Gly Ala Tyr Ser Pro Glu Asp Asn Ser Thr Gln Trp Phe His Asn Glu
 65                  70                  75                  80

Ser Leu Ile Pro Ser Gln Ala Ser Ser Tyr Leu Ile Asp Ala Ala Thr
                 85                  90                  95

Val Asp Asp Ser Gly Glu Tyr Arg Cys Gln Thr Ser Leu Ser Thr Leu
                100                 105                 110

Ser Asp Pro Val Gln Leu Glu Val His Ile Gly Trp Leu Leu Leu Gln
            115                 120                 125

Ala Pro Arg Trp Glu Phe Lys Glu Gly Asp Pro Ile His Leu Arg Cys
130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Val
            180                 185                 190

Gly Arg Lys Asn Val Ser Ser Glu Thr Val Asn Ile Thr Ile Thr Gln
            195                 200                 205

Gly Gly His His His His His His
    210                 215

<210> SEQ ID NO 68
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide encoding FcR13

<400> SEQUENCE: 68
atgaaaataa aaacaggtgc acgcatcctc gcattatccg cattaacgac gatgatgttt      60
tccgcctcgg ctctcgccaa aatcgaagaa gccatgggca tgcgtaccgg agatatgccg     120
aaagcggagg tgattctgga accgccgtgg aatcgcgtgc tggagaaaga ttcagtgacc     180
cttaaatgcc ggggcgcgta tagcccggaa gataacagca cccagtggtt ccacaatgaa     240
agcctgattc ccagccaggc gagcagctac cttattgatg cggcgacggt ggatgatagc     300
ggcgaatatc gttgccagac cagcctgagc accctgagcg atccggtgca gctggaggtg     360
cacatcgggt ggcttctgtt acaggctcca cggtgggagt tcaaagaggg ggatccgatt     420
catctgcggt gtcactcctg gaagaatacc gccctgcata agtgaccta cctgcaaaac     480 ggcaagggcc gcaagtattt ccaccacaac tccgacttct atattcccaa agcgacgctg     540
aaggacagcg gcagctattc ctgccgtggg ctggtgggca gaaaaaatgt gagcagcgag     600
accgtgaata ttaccattac ccaaggggggc catcatcatc atcatcat                 648

<210> SEQ ID NO 69
<211> LENGTH: 216
<212> TYPE: PRT
<213> ORGANISM: Artificial Sequence
<220> FEATURE:
<223> OTHER INFORMATION: Description of Artificial Sequence: Synthetic
      FcR14 polypeptide

<400> SEQUENCE: 69

Met Lys Ile Lys Thr Gly Ala Arg Ile Leu Ala Leu Ser Ala Leu Thr
```

```
                1               5                   10                  15
              Thr Met Met Phe Ser Ala Ser Ala Leu Ala Lys Ile Glu Glu Ala Met
                            20                  25                  30
              Gly Met Arg Thr Gly Asp Met Pro Lys Ala Glu Val Ile Leu Glu Pro
                            35                  40                  45
              Pro Trp Asn Arg Val Leu Glu Lys Asp Ser Val Thr Leu Lys Cys Arg
                            50                  55                  60
              Gly Ala Tyr Ser Pro Glu Asp Asn Ser Thr Gln Trp Phe His Asn Glu
              65                  70                  75                  80
              Ser Leu Ile Pro Ser Gln Ala Ser Ser Tyr Leu Ile Asp Ala Ala Thr
                            85                  90                  95
              Val Asp Asp Ser Gly Glu Tyr Arg Cys Gln Thr Ser Leu Ser Thr Leu
                            100                 105                 110
              Ser Asp Pro Val Gln Leu Glu Val His Ile Gly Trp Leu Leu Leu Gln
                            115                 120                 125
              Ala Pro Arg Trp Glu Phe Lys Glu Gly Asp Pro Ile His Leu Arg Cys
                            130                 135                 140
              His Ser Trp Lys Asn Thr Ala Leu His Lys Val Thr Tyr Leu Gln Asn
              145                 150                 155                 160
              Gly Lys Val Arg Lys Tyr Phe His His Asn Ser Asp Phe Tyr Ile Pro
                            165                 170                 175
              Lys Ala Thr Leu Lys Asp Ser Gly Ser Tyr Ser Cys Arg Gly Leu Val
                            180                 185                 190
              Gly Arg Lys Asn Val Ser Ser Glu Thr Val Asn Ile Thr Ile Thr Gln
                            195                 200                 205
              Gly Gly His His His His His His
                            210                 215

<210> SEQ ID NO 70
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide encoding FcR14

<400> SEQUENCE: 70
atgaaaataa aaacaggtgc acgcatcctc gcattatccg cattaacgac gatgatgttt      60
tccgcctcgg ctctcgccaa aatcgaagaa gccatgggca tgcgtaccgg agatatgccg     120
aaagcggagg tgattctgga accgccgtgg aatcgcgtgc tggagaaaga ttcagtgacc     180
cttaaatgcc ggggcgcgta tagcccggaa gataacagca cccagtggtt ccacaatgaa     240
agcctgattc ccagccaggc gagcagctac cttattgatg cggcgacggt ggatgatagc     300
ggcgaatatc gttgccagac cagcctgagc accctgagcg atccggtgca gctggaggtg     360
cacatcgggt ggcttctgtt acaggctcca cggtgggagt tcaaagaggg ggatccgatt     420
catctgcggt gtcactcctg gaagaatacc gccctgcata aagtgaccta cctgcaaaac     480
ggcaaggtcc gcaagtattt ccaccacaac tccgacttct atattcccaa agcgacgctg     540
aaggacagcg gcagctattc ctgccgtggg ctggtgggca gaaaaaatgt gagcagcgag     600
accgtgaata ttaccattac ccaagggggc catcatcatc atcatcat                  648

<210> SEQ ID NO 71
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 71
tgccggggcg cgcatagccc ggatgataac                                          30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ggtgctgtta tcatccgggc tatgcgcgcc                                          30

<210> SEQ ID NO 73
<211> LENGTH: 216
<212> TYPE: PRT
<213> ORGANISM: Artificial Sequence
<220> FEATURE:
<223> OTHER INFORMATION: Description of Artificial Sequence: Synthetic
      FcR16 polypeptide

<400> SEQUENCE: 73
```

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Gly Asp Met Pro Lys Ala Glu Val Ile Leu Glu Pro
        35                  40                  45

Pro Trp Asn Arg Val Leu Glu Lys Asp Ser Val Thr Leu Lys Cys Arg
    50                  55                  60

Gly Ala His Ser Pro Asp Asp Asn Ser Thr Gln Trp Phe His Asn Glu
65                  70                  75                  80

Ser Leu Ile Pro Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Val Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Val
            180                 185                 190

Gly Arg Lys Asn Val Ser Ser Glu Thr Val Asn Ile Thr Ile Thr Gln
        195                 200                 205

Gly Gly His His His His His His
    210                 215

```
<210> SEQ ID NO 74
<211> LENGTH: 648
<212> TYPE: DNA
<213> ORGANISM: Artificial Sequence
```

```
<220> FEATURE:
<223> OTHER INFORMATION: Description of Artificial Sequence: Synthetic
      polynucleotide encoding FcR16

<400> SEQUENCE: 74
atgaaaataa aaacaggtgc acgcatcctc gcattatccg cattaacgac gatgatgttt      60
tccgcctcgg ctctcgccaa aatcgaagaa gccatgggca tgcgtaccgg agatatgccg     120
aaagcggagg tgattctgga accgccgtgg aatcgcgtgc tggagaaaga ttcagtgacc     180
cttaaatgcc ggggcgcgca tagcccggat gataacagca cccagtggtt ccacaatgaa     240
agcctgattc ccagccaggc gagcagctac cttattgatg cggcgacggt ggatgatagc     300
ggcgaatatc gttgccagac cagcctgagc accctgagcg atccggtgca gctggaggtg     360
cacatcgggt ggcttctgtt acaggctcca cggtgggagt tcaaagaggg ggatccgatt     420
catctgcggt gtcactcctg gaagaatacc gccctgcata aagtgaccta cctgcaaaac     480
ggcaaggtcc gcaagtattt ccaccacaac tccgacttct atattcccaa agcgacgctg     540
aaggacagcg gcagctattc ctgccgtggg ctggtgggca gaaaaaatgt gagcagcgag     600
accgtgaata ttaccattac ccaaggggGC catcatcatc atcatcat                  648

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
attcccaaag cgacgctgga ggacagcggc                                       30

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
atagctgccg ctgtcctcca gcgtcgcttt                                       30

<210> SEQ ID NO 77
<211> LENGTH: 216
<212> TYPE: PRT
<213> ORGANISM: Artificial Sequence
<220> FEATURE:
<223> OTHER INFORMATION: Description of Artificial Sequence: Synthetic
      FcR19 polypeptide

<400> SEQUENCE: 77

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Met Arg Thr Gly Asp Met Pro Lys Ala Glu Val Ile Leu Glu Pro
            35                  40                  45

Pro Trp Asn Arg Val Leu Glu Lys Asp Ser Val Thr Leu Lys Cys Arg
        50                  55                  60

Gly Ala His Ser Pro Asp Asp Asn Ser Thr Gln Trp Phe His Asn Glu
65                  70                  75                  80
```

Ser Leu Ile Pro Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Ile Tyr Leu Gln Asn
145                 150                 155                 160

Gly Lys Val Arg Lys Tyr Phe His His Asn Ser Asp Phe His Ile Pro
                165                 170                 175

Lys Ala Thr Leu Glu Asp Ser Gly Ser Tyr Ser Cys Arg Gly Leu Val
            180                 185                 190

Gly Arg Lys Asn Val Ser Ser Glu Thr Val Asn Ile Thr Ile Thr Gln
        195                 200                 205

Gly Gly His His His His His His
    210                 215

<210> SEQ ID NO 78
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide encoding FcR19

<400> SEQUENCE: 78
atgaaaataa aaacaggtgc acgcatcctc gcattatccg cattaacgac gatgatgttt      60
tccgcctcgg ctctcgccaa aatcgaagaa gccatgggca tgcgtaccgg agatatgccg     120
aaagcggagg tgattctgga accgccgtgg aatcgcgtgc tggagaaaga ttcagtgacc     180
cttaaatgcc ggggcgcgca tagccctgat gataacagca cccagtggtt ccacaatgaa     240
agcctgattc ccagccaggc gagcagctac cttattgatg cggcgacggt ggatgatagc     300
ggcgaatatc gttgccagac cagcctgagc accctgagca tccggtgca gctggaggtg      360 cacatcgggt ggcttctgtt acaggctcca cggtgggagt tcaaagaggg ggatccgatt     420
catctgcggt gtcactcctg gaagaatacc gccctgcata aagtgatcta cctgcaaaac     480
ggcaaggtcc gcaagtattt ccaccacaac tccgacttcc atattcccaa agcgacgctg     540
gaggacagcg gcagctattc ctgccgtggg ctggtgggca gaaaaaatgt gagcagcgag     600
accgtgaata ttaccattac ccaagggggc catcatcatc atcatcat                 648

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
accgccctgc ataaagtgat ctacctgcaa                                      30

<210> SEQ ID NO 80
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 80
ttgcaggtag atcactttat gcagggcggt                                          30

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
caccacaact ccgacttcca tattcccaaa                                          30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cagcgtcgct ttgggaatat ggaagtcgga                                          30

<210> SEQ ID NO 83
<211> LENGTH: 216
<212> TYPE: PRT
<213> ORGANISM: Artificial Sequence
<220> FEATURE:
<223> OTHER INFORMATION: Description of Artificial Sequence: Synthetic
      FcR21 polypeptide

<400> SEQUENCE: 83

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Gly Asp Met Pro Lys Ala Glu Val Ile Leu Glu Pro
        35                  40                  45

Pro Trp Asn Arg Val Leu Glu Lys Asp Ser Val Thr Leu Lys Cys Arg
    50                  55                  60

Gly Ala His Ser Pro Asp Asp Asn Ser Thr Gln Trp Phe His Asn Glu
65                  70                  75                  80

Ser Leu Ile Pro Ser Gln Ala Ser Ser Tyr Leu Ile Asp Ala Ala Thr
                85                  90                  95

Val Glu Asp Ser Gly Glu Tyr Arg Cys Gln Thr Ser Leu Ser Thr Leu
            100                 105                 110

Ser Asp Pro Val Leu Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Ile Tyr Leu Gln Asn
145                 150                 155                 160

Gly Lys Val Arg Lys Tyr Phe His His Asn Ser Asp Phe His Ile Pro
                165                 170                 175

Lys Ala Thr Leu Glu Asp Ser Gly Ser Tyr Ser Cys Arg Gly Leu Val
```

```
            180                 185                 190
Gly Arg Lys Asn Val Ser Ser Glu Thr Val Asn Ile Thr Ile Thr Gln
        195                 200                 205

Gly Gly His His His His His His
    210                 215

<210> SEQ ID NO 84
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide encoding FcR21

<400> SEQUENCE: 84
atgaaaataa aaacaggtgc acgcatcctc gcattatccg cattaacgac gatgatgttt      60
tccgcctcgg ctctcgccaa aatcgaagaa gccatgggca tgcgtaccgg agatatgccg     120
aaagcggagg tgattctgga accgccgtgg aatcgcgtgc tggagaaaga ttcagtgacc     180
cttaaatgcc ggggcgcgca tagcccggat gataacagca cccagtggtt ccacaatgaa     240
agcctgattc ccagccaggc gagcagctac cttattgatg cggcgacggt ggaagatagc     300
ggcgaatatc gttgccagac cagcctgagc accctgagcg atccggtgct gctggaggtg     360
cacatcgggt ggcttctgtt acaggctcca cggtgggagt tcaaagaggg ggatccgatt     420
catctgcggt gtcactcctg gaagaatacc gccctgcata aagtgatcta cctgcaaaac     480
ggcaaggtcc gcaagtattt ccaccacaac tccgacttcc atattcccaa agcgacgctg     540
gaggacagcg gcagctattc ctgccgtggg ctggtgggca gaaaaaatgt gagcagcgag     600
accgtgaata ttaccattac ccaagggggc catcatcatc atcatcat                  648

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agcagctacc ttattgattc ggcgacggtg                                        30

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gctatcttcc accgtcgccg aatcaataag                                        30

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aaaaatgtga gcagcgaggc cgtggatatt                                        30
```

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 88
ggtaatggta atatccacgg cctcgctgct                                    30

<210> SEQ ID NO 89
<211> LENGTH: 216
<212> TYPE: PRT
<213> ORGANISM: Artificial Sequence
<220> FEATURE:
<223> OTHER INFORMATION: Description of Artificial Sequence: Synthetic
    FcR24 polypeptide

<400> SEQUENCE: 89

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Gly Asp Met Pro Lys Ala Glu Val Ile Leu Glu Pro
        35                  40                  45

Pro Trp Asn Arg Val Leu Glu Lys Asp Ser Val Thr Leu Lys Cys Arg
    50                  55                  60

Gly Ala His Ser Pro Asp Asn Ser Thr Gln Trp Phe His Asn Glu
65                  70                  75                  80

Ser Leu Ile Pro Ser Gln Ala Ser Ser Tyr Leu Ile Asp Ser Ala Thr
                85                  90                  95

Val Glu Asp Ser Gly Glu Tyr Arg Cys Gln Thr Ser Leu Ser Thr Leu
            100                 105                 110

Ser Asp Pro Val Leu Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Ile Tyr Leu Gln Asn
145                 150                 155                 160

Gly Lys Val Arg Lys Tyr Phe His His Asn Ser Asp Phe His Ile Pro
                165                 170                 175

Lys Ala Thr Leu Glu Asp Ser Gly Ser Tyr Ser Cys Arg Gly Leu Val
            180                 185                 190

Gly Arg Lys Asn Val Ser Ser Glu Ala Val Asp Ile Thr Ile Thr Gln
        195                 200                 205

Gly Gly His His His His His His
    210                 215

<210> SEQ ID NO 90
<211> LENGTH: 648
<212> TYPE: DNA
<213> ORGANISM: Artificial Sequence
<220> FEATURE:
<223> OTHER INFORMATION: Description of Artificial Sequence: Synthetic
    polynucleotide encoding FcR24

<400> SEQUENCE: 90
atgaaaataa aaacaggtgc acgcatcctc gcattatccg cattaacgac gatgatgttt    60

```
tccgcctcgg ctctcgccaa aatcgaagaa gccatgggca tgcgtaccgg agatatgccg    120
aaagcggagg tgattctgga accgccgtgg aatcgcgtgc tggagaaaga ttcagtgacc    180
cttaaatgcc ggggcgcgca tagcccggat gataacagca cccagtggtt ccacaatgaa    240
agcctgattc ccagccaggc gagcagctac cttattgatt cggcgacggt ggaagatagc    300
ggcgaatatc gttgccagac cagcctgagc accctgagcg atccggtgct gctggaggtg    360
cacatcgggt ggcttctgtt acaggctcca cggtgggagt tcaaagaggg ggatccgatt    420
catctgcggt gtcactcctg gaagaatacc gccctgcata aagtgatcta cctgcaaaac    480
ggcaaggtcc gcaagtattt ccaccacaac tccgacttcc atattcccaa agcgacgctg    540
gaggacagcg gcagctattc ctgccgtggg ctggtgggca gaaaaaatgt gagcagcgag    600
gccgtggata ttaccattac ccaagggggc catcatcatc atcatcat             648
```

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (14)..(15)
<223> OTHER INFORMATION: a, c, t, g, unknown or other

<400> SEQUENCE: 91
cctgcataaa gtgnnktacc tgcaaaacgg                                    30

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (16)..(17)
<223> OTHER INFORMATION: a, c, t, g, unknown or other

<400> SEQUENCE: 92
ccgttttgca ggtamnncac tttatgcagg                                    30

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (14)..(15)
<223> OTHER INFORMATION: a, c, t, g, unknown or other

<400> SEQUENCE: 93
caactccgac ttcnnkattc ccaaagcgac                                    30

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic

```
        oligonucleotide
<220> FEATURE:
<221> NAME/KEY: modified_base
<222> LOCATION: (16)..(17)
<223> OTHER INFORMATION: a, c, t, g, unknown or other

<400> SEQUENCE: 94
gtcgctttgg gaatmnngaa gtcggagttg                                    30

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(14)
<223> OTHER INFORMATION: a, c, t, g, unknown or other

<400> SEQUENCE: 95
ctgccgaaag cgnnkgtgtt tctggaaccg                                    30

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(15)
<223> OTHER INFORMATION: a, c, t, g, unknown or other

<400> SEQUENCE: 96
ttccagaaac acmnncgctt tcggcagatc                                    30

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(13)
<223> OTHER INFORMATION: a, c, t, g, unknown or other

<400> SEQUENCE: 97
aaccgcagtg gnnkcgcgtg ctggagaaag                                    30

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(11)
<223> OTHER INFORMATION: a, c, t, g, unknown or other

<400> SEQUENCE: 98
agcacgcgmn nccactgcgg ttccagaaac                                    30
```

```
<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(14)
<223> OTHER INFORMATION: a, c, t, g, unknown or other

<400> SEQUENCE: 99
gtgttcaaag agnnkgatcc gattcatctg                                        30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: a, c, t, g, unknown or other

<400> SEQUENCE: 100
aatcggatcm nnctctttga acacccaccg                                        30

<210> SEQ ID NO 101
<211> LENGTH: 22
<212> TYPE: PRT
<213> ORGANISM: Artificial Sequence
<220> FEATURE:
<223> OTHER INFORMATION: Description of Artificial Sequence: Synthetic
      PelB signal peptide

<400> SEQUENCE: 101

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 102
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
catgaaatac ctgctgtcga ccgctgctgc tggtctgctg ctcctcgctg cccagccggc       60
gatggc                                                                  66

<210> SEQ ID NO 103
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
catggccatc gccggctggg cagcgaggag cagcagacca gcagcagcgg tcgacagcag       60
gtattt                                                                  66
```

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tgtggtatgg ctgtgcagg                                                   19

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tcggcatggg gtcaggtg                                                    18

<210> SEQ ID NO 106
<211> LENGTH: 207
<212> TYPE: PRT
<213> ORGANISM: Artificial Sequence
<220> FEATURE:
<223> OTHER INFORMATION: Description of Artificial Sequence: Synthetic
      FcRCys polypeptide

<400> SEQUENCE: 106

Met Lys Tyr Leu Leu Ser Thr Ala Ala Ala Gly Leu Leu Leu Leu Ala
1               5                   10                  15

Ala Gln Pro Ala Met Ala Met Gly Met Arg Thr Glu Asp Leu Pro Lys
            20                  25                  30

Ala Val Val Phe Leu Glu Pro Gln Trp Tyr Arg Val Leu Glu Lys Asp
        35                  40                  45

Ser Val Thr Leu Lys Cys Gln Gly Ala Tyr Ser Pro Glu Asp Asn Ser
    50                  55                  60

Thr Gln Trp Phe His Asn Glu Ser Leu Ile Ser Ser Gln Ala Ser Ser
65                  70                  75                  80

Tyr Phe Ile Asp Ala Ala Thr Val Asp Asp Ser Gly Glu Tyr Arg Cys
                85                  90                  95

Gln Thr Asn Leu Ser Thr Leu Ser Asp Pro Val Gln Leu Glu Val His
            100                 105                 110

Ile Gly Trp Leu Leu Leu Gln Ala Pro Arg Trp Val Phe Lys Glu Glu
        115                 120                 125

Asp Pro Ile His Leu Arg Cys His Ser Trp Lys Asn Thr Ala Leu His
    130                 135                 140

Lys Val Thr Tyr Leu Gln Asn Gly Lys Gly Arg Lys Tyr Phe His His
145                 150                 155                 160

Asn Ser Asp Phe Tyr Ile Pro Lys Ala Thr Leu Lys Asp Ser Gly Ser
                165                 170                 175

Tyr Phe Cys Arg Gly Leu Val Gly Ser Lys Asn Val Ser Ser Glu Thr
            180                 185                 190

Val Asn Ile Thr Ile Thr Gln Gly Cys Arg Asn Asp Thr Cys Gly
        195                 200                 205

<210> SEQ ID NO 107

```
<211> LENGTH: 621
<212> TYPE: DNA
<213> ORGANISM: Artificial Sequence
<220> FEATURE:
<223> OTHER INFORMATION: Description of Artificial Sequence: Synthetic
      polynucleotide encoding FcRCys

<400> SEQUENCE: 107
atgaaatacc tgctgtcgac cgctgctgct ggtctgctgc tcctcgctgc ccagccggcg      60
atggccatgg gcatgcgtac cgaagatctg ccgaaagcgg tggtgtttct ggaaccgcag     120
tggtatcgcg tgctggagaa agattctgtg acccttaaat gccagggcgc gtatagcccg     180
gaagataaca gcacccagtg gttccacaat gaaagcctga tttccagcca ggcgagcagc     240
tactttattg atgcggcgac ggtggatgat agcggcgaat atcgttgcca gaccaacctg     300
agcaccctga gcgatccggt gcagctggag gtgcacatcg ggtggcttct gttacaggct     360
ccacggtggg tgttcaaaga ggaggatccg attcatctgc ggtgtcactc ctggaagaat     420
accgccctgc ataaagtgac ctacctgcaa aacggcaagg gccgcaagta tttccaccac     480
aactccgact tctatattcc caaagcgacg ctgaaggaca gcggcagcta tttctgccgt     540
gggctggtgg gcagcaaaaa tgtgagcagc gagaccgtga atattaccat tacccaaggg     600
tgccgcaacg atacctgcgg a                                              621
```

FC-BINDING PROTEIN, METHOD FOR PRODUCING SAID PROTEIN, ANTIBODY ADSORBENT USING SAID PROTEIN, AND METHOD FOR SEPARATING ANTIBODY USING SAID ADSORBENT

SEQUENCE LISTING

The instant application contains a Sequence Listing which has been submitted electronically in ASCII format and is hereby incorporated by reference in its entirety. Said ASCII copy, created on Feb. 15, 2017, is named P51560_SL.txt and is 80,830 bytes in size.

TECHNICAL FIELD

The present invention relates to an Fc-binding protein having affinity for immunoglobulin. More particularly, the present invention relates to an Fc-binding protein having higher stability to heat and acid than the wild type, a method for producing said protein, an antibody adsorbent obtained by immobilizing said protein on an insoluble support, and a method for separating antibody using said adsorbent.

BACKGROUND ART

Fc receptors are a group of molecules that bind to an Fc region of immunoglobulin molecules. Individual molecules recognize a single or the same group of immunoglobulin isotype by a recognition domain belonging to the immunoglobulin superfamily, by a recognition domain on the Fc receptor. This determines which accessory cells are driven in an immune response. Fc receptors can be further categorized into several subtypes, including Fcγ receptors that are receptors to immunoglobulin G (IgG), Fcε receptors that bind to the Fc region of IgE, and Fcα receptors that bind to the Fc region of IgA. In addition, each receptor is further sub-categorized, and FcγRI, FcγRIIa, FcγRIIb, FcγRIIIa and FcγRIIIb have been reported as Fcγ receptors (Non-Patent Literature 1).

Among these Fcγ receptors, FcγRIIIa are present on the cell surface of natural killer cells (NK cells) and macrophages, and are important receptors involved in an antibody-dependent cell-mediated cytotoxicity (ADCC) which is an important part of the human immune system. Affinity between FcγRIIIa and human IgG has been reported to demonstrate a coupling constant ($K_a$) that indicates binding strength, of $10^7$ $M^{-1}$ or less (Non-Patent Literature 2). The amino acid sequence of human FcγRIIIa has been published in public databases such as UniProt (Accession number: P08637). In addition, functional domains of human FcγRIIIa, signal peptide sequences for spanning of the cell membrane, and the positions of cell transmembrane regions have also been similarly published. FIG. 1 shows a schematic diagram of the structure of human FcγRIIIa. Furthermore, the numbers in the diagram indicate amino acid numbers, and those numbers correspond to the amino acid numbers described in SEQ ID NO: 1. Namely, the amino acid sequence from methionine (Met) at position 1 to alanine (Ala) at position 16 constitutes the signal sequence (S), the amino acid sequence from glycine (Gly) at position 17 to glutamine (Gln) at position 208 constitutes the extracellular region (EC), the amino acid sequence from valine (Val) at position 209 to valine (Val) at position 229 constitutes the cell transmembrane region (TM), and the amino acid sequence from lysine (Lys) at position 230 to lysine (Lys) at position 254 constitutes the intracellular region (C). Furthermore, although FcγRIIIa binds particularly strongly to IgG1 and IgG3 among the subclasses of human IgG ranging from IgG1 to IgG4, it is known to bind weakly to IgG2 and IgG4.

In addition, pharmaceuticals (antibody drugs) have recently come to be used that contain antibodies for treating cancer, immune diseases, etc. The antibodies used in these antibody drugs are produced by culturing cells obtained by genetic engineering techniques that are capable of expressing that antibody (such as Chinese hamster ovary (CHO) cells), followed by purifying the resulting antibody to a high purity using techniques such as column chromatography. However, recent researches have demonstrated that the aforementioned antibodies are determined to form an assembly of various molecules as a result of being subjected to modification such as oxidation, reduction, isomerization or glycosylation, thereby resulting in concerns over the effects of these modifications on efficacy and safety.

Peptide mapping, analysis by two-dimensional electrophoresis and LC-MS analysis including release of glycan chains have been used to analyze the molecular structure of antibodies used in antibody drugs (Non-Patent Literature 3). However, each of these methods has an extremely complex procedure. An example of a simpler method for analyzing the molecular structure of antibodies is chromatographic analysis. More specifically, aggregates and degradation products can be separated and quantified by separating antibodies based on molecular weight using gel filtration chromatography. In addition, antibodies can also be separated by ion exchange chromatography based on differences in charge of antibody molecules. However, in the case of the aforementioned chromatographic analyses, the resulting analysis results were limited since slight structural changes in antibody molecules were unable to be identified.

On the other hand, among the various chromatographic techniques, affinity chromatography makes it possible to analyze antibody structure based on affinity between an antibody and an affinity ligand immobilized on an insoluble support. Consequently, slight structural changes in antibody molecules can be identified (Patent Literature 1 and Non-Patent Literature 4). However, separating antibodies on an industrial scale using the methods described in Patent Literature 1 and Non-Patent Literature 4 is in fact difficult and improvement is desired.

Moreover, among the human IgG used in antibody drugs, antibody-dependent cell-mediated cytotoxicity (ADCC) activity is known to change due to differences in the N-type glycan chain linked to the asparagine residue at position 279 of the Fc region, and ADCC activity has been reported to improve in antibody that has undergone deletion of fucose, a type of glycan chain, in particular (Non-Patent Literature 5).

The degree of ADCC activity of the antibody has important significance in antibody drugs. However, since antibody drugs are normally produced with genetic modification techniques using animal cells as hosts and glycosylation cannot be controlled within the host, it is difficult to express antibodies having a constant level of ADCC activity. In addition, considerable amounts of time and labor are required to separate antibodies from the expressed antibodies based on ADCC activity.

CITATION LIST

Patent Literature

Patent Literature 1: WO 2013/120929

Non-Patent Literature

Non-Patent Literature 1: Takai, T., Jpn. J. Clin. Immunol., 28, 318-326, 2005
Non-Patent Literature 2: J. Galon, et al, Eur. J. Immunol., 27, 1928-1932, 1997
Non-Patent Literature 3: Journal of Chromatography A, 720, 217-225, 1996
Non-Patent Literature 4: mAbs, 5(4), 576-586, 2013
Non-Patent Literature 5: Shinkawa, T., J. Biol. Chem., 278, 3466-3473, 2003

SUMMARY OF INVENTION

Technical Problem

An object of the present invention is to provide an Fc-binding protein having improved stability to heat and acid in particular, a method for producing said protein, and an antibody adsorbent that uses said protein.

In addition, another object of the present invention is to provide a method for separating antibodies using a support having an affinity ligand immobilized thereon, wherein the antibodies can be separated easily and highly efficiently based on differences in the molecular structure thereof.

In addition, still another object of the present invention is to provide a method for separating antibodies based on the degree of antibody-dependent cell-mediated cytotoxicity activity.

Solution to Problem

As a result of conducting extensive studies to achieve the aforementioned object, the inventors of the present invention specified an amino acid residue involved in improving stability in human FcγRIIIa, and found that variants, in which said amino acid residue is substituted with other amino acid residues, have superior stability to heat and acid, thereby leading to completion of the present invention.

In addition, as a result of conducting extensive studies to achieve the aforementioned another object, the inventors of the present invention found that antibody separation resolution is improved by adding a certain concentration of chloride ion or sulfate ion to the equilibration solution of a column packed with an insoluble support having an affinity ligand immobilized thereon, thereby leading to completion of the present invention.

In addition, as a result of conducting extensive studies to achieve the aforementioned still another object, the inventors of the present invention found that, by using an adsorbent obtained by immobilizing an Fc-binding protein to an insoluble support, antibodies can be separated based on the degree of antibody-dependent cell-mediated cytotoxicity (ADCC) activity, thereby leading to completion of the present invention.

Namely, the present application includes the aspects described in (A) to (T) indicated below.

(A) An Fc-binding protein, comprising the amino acid residues from position 33 to position 208 of the amino acid sequence according to SEQ ID NO: 37, wherein at least any one of the amino acid substitutions of the following (1) to (84) is introduced into the amino acid residues from position 33 to position 208:

(1) phenylalanine at position 45 of SEQ ID NO: 37 is substituted with isoleucine or leucine,
(2) glutamic acid at position 55 of SEQ ID NO: 37 is substituted with glycine,
(3) glutamine at position 64 of SEQ ID NO: 37 is substituted with arginine,
(4) tyrosine at position 67 of SEQ ID NO: 37 is substituted with serine,
(5) phenylalanine at position 77 of SEQ ID NO: 37 is substituted with tyrosine,
(6) aspartic acid at position 93 of SEQ ID NO: 37 is substituted with glycine,
(7) aspartic acid at position 98 of SEQ ID NO: 37 is substituted with glutamic acid,
(8) glutamine at position 106 of SEQ ID NO: 37 is substituted with arginine,
(9) glutamine at position 128 of SEQ ID NO: 37 is substituted with leucine,
(10) valine at position 133 of SEQ ID NO: 37 is substituted with glutamic acid,
(11) lysine at position 135 of SEQ ID NO: 37 is substituted with asparagine or glutamic acid,
(12) threonine at position 156 of SEQ ID NO: 37 is substituted with isoleucine,
(13) leucine at position 158 of SEQ ID NO: 37 is substituted with glutamine,
(14) phenylalanine at position 187 of SEQ ID NO: 37 is substituted with serine,
(15) leucine at position 191 of SEQ ID NO: 37 is substituted with arginine,
(16) asparagine at position 196 of SEQ ID NO: 37 is substituted with serine,
(17) isoleucine at position 204 of SEQ ID NO: 37 is substituted with valine,
(18) methionine at position 34 of SEQ ID NO: 37 is substituted with isoleucine, lysine or threonine,
(19) glutamic acid at position 37 of SEQ ID NO: 37 is substituted with glycine or lysine,
(20) leucine at position 39 of SEQ ID NO: 37 is substituted with methionine or arginine,
(21) glutamine at position 49 of SEQ ID NO: 37 is substituted with proline,
(22) lysine at position 62 of SEQ ID NO: 37 is substituted with isoleucine or glutamic acid,
(23) glutamine at position 64 of SEQ ID NO: 37 is substituted with tryptophan,
(24) tyrosine at position 67 of SEQ ID NO: 37 is substituted with histidine or asparagine,
(25) glutamic acid at position 70 of SEQ ID NO: 37 is substituted with glycine or aspartic acid,
(26) asparagine at position 72 of SEQ ID NO: 37 is substituted with serine or isoleucine,
(27) phenylalanine at position 77 of SEQ ID NO: 37 is substituted with leucine,
(28) glutamic acid at position 80 of SEQ ID NO: 37 is substituted with glycine,
(29) serine at position 81 of SEQ ID NO: 37 is substituted with arginine,
(30) isoleucine at position 83 of SEQ ID NO: 37 is substituted with leucine,
(31) serine at position 84 of SEQ ID NO: 37 is substituted with proline,
(32) serine at position 85 of SEQ ID NO: 37 is substituted with asparagine,

(33) alanine at position 87 of SEQ ID NO: 37 is substituted with threonine,
(34) tyrosine at position 90 of SEQ ID NO: 37 is substituted with phenylalanine,
(35) phenylalanine at position 91 of SEQ ID NO: 37 is substituted with arginine,
(36) aspartic acid at position 93 of SEQ ID NO: 37 is substituted with valine or glutamic acid,
(37) alanine at position 94 of SEQ ID NO: 37 is substituted with glutamic acid,
(38) valine at position 97 of SEQ ID NO: 37 is substituted with methionine or glutamic acid,
(39) aspartic acid at position 98 of SEQ ID NO: 37 is substituted with alanine,
(40) glutamic acid at position 102 of SEQ ID NO: 37 is substituted with aspartic acid,
(41) glutamine at position 106 of SEQ ID NO: 37 is substituted with leucine,
(42) leucine at position 109 of SEQ ID NO: 37 is substituted with glutamine,
(43) glutamine at position 117 of SEQ ID NO: 37 is substituted with leucine,
(44) glutamic acid at position 119 of SEQ ID NO: 37 is substituted with valine,
(45) histidine at position 121 of SEQ ID NO: 37 is substituted with arginine,
(46) proline at position 130 of SEQ ID NO: 37 is substituted with leucine,
(47) lysine at position 135 of SEQ ID NO: 37 is substituted with tyrosine,
(48) glutamic acid at position 136 of SEQ ID NO: 37 is substituted with valine,
(49) histidine at position 141 of SEQ ID NO: 37 is substituted with glutamine,
(50) serine at position 146 of SEQ ID NO: 37 is substituted with threonine,
(51) lysine at position 154 of SEQ ID NO: 37 is substituted with arginine,
(52) glutamine at position 159 of SEQ ID NO: 37 is substituted with histidine,
(53) glycine at position 163 of SEQ ID NO: 37 is substituted with valine,
(54) lysine at position 165 of SEQ ID NO: 37 is substituted with methionine,
(55) phenylalanine at position 167 of SEQ ID NO: 37 is substituted with tyrosine,
(56) histidine at position 169 of SEQ ID NO: 37 is substituted with tyrosine,
(57) tyrosine at position 174 of SEQ ID NO: 37 is substituted with phenylalanine,
(58) lysine at position 177 of SEQ ID NO: 37 is substituted with arginine,
(59) serine at position 185 of SEQ ID NO: 37 is substituted with glycine,
(60) serine at position 194 of SEQ ID NO: 37 is substituted with arginine,
(61) asparagine at position 196 of SEQ ID NO: 37 is substituted with lysine,
(62) threonine at position 201 of SEQ ID NO: 37 is substituted with alanine,
(63) asparagine at position 203 of SEQ ID NO: 37 is substituted with isoleucine or lysine,
(64) threonine at position 207 of SEQ ID NO: 37 is substituted with alanine,
(65) alanine at position 94 of SEQ ID NO: 37 is substituted with serine,
(66) aspartic acid at position 98 of SEQ ID NO: 37 is substituted with glutamic acid,
(67) glutamine at position 117 of SEQ ID NO: 37 is substituted with arginine,
(68) tyrosine at position 174 of SEQ ID NO: 37 is substituted with histidine,
(69) lysine at position 181 of SEQ ID NO: 37 is substituted with glutamic acid,
(70) asparagine at position 203 of SEQ ID NO: 37 is substituted with aspartic acid or tyrosine,
(71) lysine at position 56 of SEQ ID NO: 37 is substituted with glutamine,
(72) lysine at position 62 of SEQ ID NO: 37 is substituted with asparagine,
(73) alanine at position 66 of SEQ ID NO: 37 is substituted with threonine,
(74) asparagine at position 72 of SEQ ID NO: 37 is substituted with tyrosine,
(75) histidine at position 78 of SEQ ID NO: 37 is substituted with leucine,
(76) serine at position 81 of SEQ ID NO: 37 is substituted with glycine,
(77) tyrosine at position 90 of SEQ ID NO: 37 is substituted with histidine,
(78) aspartic acid at position 138 of SEQ ID NO: 37 is substituted with glutamic acid,
(79) histidine at position 153 of SEQ ID NO: 37 is substituted with glutamine,
(80) threonine at position 156 of SEQ ID NO: 37 is substituted with alanine, arginine, leucine, lysine, phenylalanine, serine, valine or methionine,
(81) tyrosine at position 157 of SEQ ID NO: 37 is substituted with phenylalanine,
(82) tyrosine at position 174 of SEQ ID NO: 37 is substituted with leucine, cysteine, isoleucine, lysine, tryptophan or valine,
(83) isoleucine at position 206 of SEQ ID NO: 37 is substituted with valine, and
(84) threonine at position 207 of SEQ ID NO: 37 is substituted with isoleucine.

(B) The Fc-binding protein described in (A), comprising the amino acid residues from position 33 to position 208 in the amino acid sequence according to any of SEQ ID NO: 39, SEQ ID NO: 43, SEQ ID NO: 47, SEQ ID NO: 51, SEQ ID NO: 55, SEQ ID NO: 63, SEQ ID NO: 67, SEQ ID NO: 69, SEQ ID NO: 73, SEQ ID NO: 77, SEQ ID NO: 83 and SEQ ID NO: 89.

(C) The Fc-binding protein described in (B), consisting of the amino acid sequence according to any of SEQ ID NO: 39, SEQ ID NO: 43, SEQ ID NO: 47, SEQ ID NO: 51, SEQ ID NO: 55, SEQ ID NO: 63, SEQ ID NO: 67, SEQ ID NO: 69, SEQ ID NO: 73, SEQ ID NO: 77, SEQ ID NO: 83 and SEQ ID NO: 89.

(D) The Fc-binding protein described in (A), wherein at least one amino acid substitution of the following (85) to (88) is introduced:
(85) leucine at position 82 of SEQ ID NO: 37 is substituted with histidine or arginine,
(86) glycine at position 163 of SEQ ID NO: 37 is substituted with aspartic acid,
(87) tyrosine at position 174 of SEQ ID NO: 37 is substituted with histidine, and
(88) valine at position 192 of SEQ ID NO: 37 is substituted with phenylalanine.

(E) An adsorbent obtained by immobilizing the Fc-binding protein described in any of (A) to (D) on an insoluble support.

(F) A method for separating antibodies, comprising: a step for equilibrating a column by adding an equilibration solution to a column packed with the adsorbent described in (E), a step for adding a solution containing antibody to the equilibrated column and adsorbing the antibody to the support, and a step for eluting antibody adsorbed to the support using an eluent.

(G) The separation method described in (F), wherein the equilibration solution contains chloride ion or sulfate ion at 30 mM or more.

(H) A method for separating antibodies based on the degree of antibody-dependent cell-mediated cytotoxicity, comprising using the adsorbent described in (E).

(I) An antibody obtained by the separation method described in any of (F) to (H).

(J) A method for identifying a difference in glycan chain structure between antibodies, comprising separating antibodies by using the adsorbent described in (E).

(K) A method for separating glycan chains using the adsorbent described in (E).

(L) A glycan chain obtained by the separation method described in (K).

(M) A polynucleotide encoding the Fc-binding protein described in any of (A) to (D).

(N) An expression vector containing the polynucleotide described in (M).

(O) A transformant obtained by transforming a host with the expression vector described in (N).

(P) The transformant described in (O), wherein the host is *Escherichia coli*.

(Q) A method for producing an Fc-binding protein, comprising expressing an Fc-binding protein by culturing the transformant described in (O) or (P); and recovering the expressed Fc-binding protein from the culture.

(R) A method for separating antibodies, comprising: a step for equilibrating a column by adding an equilibration solution to a column packed with an insoluble support having an Fc-binding protein immobilized thereon, a step for adding a solution containing antibody to the equilibrated column and adsorbing the antibody onto the support, and a step for eluting antibody adsorbed to the support using an eluent; wherein, the equilibration solution contains chloride ion or sulfate ion at 30 mM or more.

(S) A method for separating antibodies based on the degree of antibody-dependent cell-mediated cytotoxicity activity using an adsorbent obtained by immobilizing an Fc-binding protein on an insoluble support.

(T) The method described in (R) or (S), wherein the Fc-binding protein is human FcγRIIIa.

The following provides a detailed explanation of the present invention.

The Fc-binding protein of the present invention is a protein that has a binding ability to the Fc region of an antibody, wherein the Fc-binding protein at least contains amino acid residues from glycine at position 17 to glutamine at position 192 of the extracellular region (EC region of FIG. 1) of human FcγRIIIa comprised of the amino acid sequence according to SEQ ID NO: 1, and has an amino acid substitution at a specific position in the amino acid residues from position 17 to position 192. Thus, the Fc-binding protein of the present invention may contain all or a portion of the signal peptide region (S region of FIG. 1) on the N-terminal side of the extracellular region, or may contain all or a portion of the transmembrane region (TM region of FIG. 1) and intracellular region (region C of FIG. 1) on the C-terminal side of the extracellular region. More specifically, amino acid substitutions at the aforementioned specific positions are any of the substitutions of Val27Glu (in this nomenclature, valine at position 27 of SEQ ID NO: 1 (position 43 of SEQ ID NO; 37) is substituted with glutamic acid, and to apply similarly hereinafter), Tyr35Asn, Phe75Leu, Asn92Ser, Glu121Gly, Phe29Ile, Phe29Leu, Glu39Gly, Gln48Arg, Tyr51Ser, Phe61Tyr, Asp77Gly, Asp82Glu, Gln90Arg, Gln112Leu, Val117Glu, Lys119Asn, Lys119Glu, Thr140Ile, Leu142Gln, Phe171Ser, Leu175Arg, Asn180Ser, Ile188Val, Met18Ile, Met18Lys, Met18Thr, Glu21Gly, Glu21Lys, Leu23Met, Leu23Arg, Gln33Pro, Lys46Ile, Lys46Glu, Gln48Trp, Tyr51His, Tyr51Asn, Glu54Gly, Glu54Asp, Asn56Ser, Asn56Ile, Phe61Leu, Glu64Gly, Ser65Arg, Ile67Leu, Ser68Pro, Ser69Asn, Ala71Thr, Tyr74Phe, Phe75Arg, Asp77Val, Asp77Glu, Ala78Glu, Val81Met, Val81Glu, Asp82Ala, Glu86Asp, Gln90Leu, Leu93Gln, Gln101Leu, Glu103Val, His105Arg, Pro114Leu, Lys119Tyr, Glu120Val, His125Gln, Ser130Thr, Lys138Arg, Gln143His, Gly147Val, Lys149Met, Phe151Tyr, His153Tyr, Tyr158Phe, Lys161Arg, Ser169Gly, Ser178Arg, Asn180Lys, Thr185Ala, Asn187Ile, Asn187Lys, Thr191Ala, Ala78Ser, Asp82Glu, Gln101Arg, Tyr158His, Lys165Glu, Asn187Asp, Asn187Tyr, Lys40Gln, Lys46Asn, Ala50Thr, Asn56Tyr, His62Leu, Ser65Gly, Tyr74His, Asp122Glu, His137Gln, Thr140Ala, Thr140Arg, Thr140Leu, Thr140Lys, Thr140Phe, Thr140Ser, Thr140Val, Thr140Met, Tyr141Phe, Tyr158Leu, Tyr158Cys, Tyr158Ile, Tyr158Lys, Tyr158Trp, Tyr158Val, Ile190Val and Thr191Ile. Furthermore, although variants of wild-type FcγRIIIa are known that have one or more of any of the amino acid substitutions of Leu66His, Leu66Arg, Gly147Asp, Tyr158His and Val176Phe, these amino acid substitutions may also be contained in addition to the amino acid substitutions at the aforementioned specific positions.

When producing the Fc-binding protein of the present invention by carrying out amino acid substitution, the amino acid residues at specific positions may be substituted with amino acids other than the aforementioned amino acids provided antibody binding activity is retained. An example thereof is a conservative substitution in which a substitution is carried out between amino acids in which the physical properties and chemical properties, or either the physical properties or chemical properties, of both amino acids are similar. Conservative substitution is known among persons with ordinary skill in the art to maintain protein function between proteins that have been substituted and proteins that have not been substituted not only with respect to Fc-binding proteins, but also with respect to proteins in general. Examples of conservative substitution include substitutions between glycine and alanine, aspartic acid and glutamic acid, serine and proline, or glutamic acid and alanine (Protein Structure and Function, Medical Science International, 9, 2005).

In the Fc-binding protein of the present invention, there are no particular limitations on the number of amino acids substituted. Examples thereof include the Fc-binding proteins indicated in the following (a) to (1). These Fc-binding proteins are preferable from the viewpoint of having improved stability to heat, acid or base.

(a) Fc-binding protein containing the amino acid residues from position 33 to position 208 of the amino acid sequence according to SEQ ID NO: 37, wherein phenylalanine at position 45 is substituted with isoleucine, and valine at position 133 is substituted with glutamic acid in the amino acid residues from position 33 to position 208 (Fc-binding protein comprising the amino acid sequence from position 33 to position 208 of the amino acid sequence according to SEQ ID NO: 39).

(b) Fc-binding protein containing the amino acid residues from position 33 to position 208 of the amino acid sequence according to SEQ ID NO: 37, wherein phenylalanine at position 45 is substituted with isoleucine, valine at position 133 is substituted with glutamic acid, and phenylalanine at position 187 is substituted with serine in the amino acid residues from position 33 to position 208 (Fc-binding protein containing the amino acid sequence from position 33 to position 208 of the amino acid sequence according to SEQ ID NO: 43).

(c) Fc-binding protein containing the amino acid residues from position 33 to position 208 of the amino acid sequence according to SEQ ID NO: 37, wherein phenylalanine at position 45 is substituted with isoleucine, glutamine at position 64 is substituted with arginine, valine at position 133 is substituted with glutamic acid, and phenylalanine at position 187 is substituted with serine in the amino acid residues from position 33 to position 208 (Fc-binding protein containing the amino acid sequence from position 33 to position 208 of the amino acid sequence according to SEQ ID NO: 47).

(d) Fc-binding protein containing the amino acid residues from position 33 to position 208 of the amino acid sequence according to SEQ ID NO: 37, wherein phenylalanine at position 45 is substituted with isoleucine, glutamine at position 64 is substituted with arginine, tyrosine at position 67 is substituted with serine, valine at position 133 is substituted with glutamic acid, and phenylalanine at position 187 is substituted with serine in the amino acid residues from position 33 to position 208 (Fc-binding protein containing the amino acid sequence from position 33 to position 208 of the amino acid sequence according to SEQ ID NO: 51).

(e) Fc-binding protein containing the amino acid residues from position 33 to position 208 of the amino acid sequence according to SEQ ID NO: 37, wherein phenylalanine at position 45 is substituted with isoleucine, glutamine at position 64 is substituted with arginine, tyrosine at position 67 is substituted with serine, glutamine at position 106 is substituted with arginine, valine at position 133 is substituted with glutamic acid, and phenylalanine at position 187 is substituted with serine in the amino acid residues from position 33 to position 208 (Fc-binding protein containing the amino acid sequence from position 33 to position 208 of the amino acid sequence according to SEQ ID NO: 55).

(f) Fc-binding protein containing the amino acid residues from position 33 to position 208 of the amino acid sequence according to SEQ ID NO: 37, wherein glutamic acid at position 37 is substituted with glycine, leucine at position 39 is substituted with methionine, phenylalanine at position 45 is substituted with isoleucine, glutamine at position 64 is substituted with arginine, valine at position 133 is substituted with glutamic acid, phenylalanine at position 187 is substituted with serine, and serine at position 194 is substituted with arginine in the amino acid residues from position 33 to position 208 (Fc-binding protein containing the amino acid sequence from position 33 to position 208 of the amino acid sequence according to SEQ ID NO: 63).

(g) Fc-binding protein containing the amino acid residues from position 33 to position 208 of the amino acid sequence according to SEQ ID NO: 37, wherein glutamic acid at position 37 is substituted with glycine, leucine at position 39 is substituted with methionine, phenylalanine at position 45 is substituted with isoleucine, glutamine at position 64 is substituted with arginine, serine at position 84 is substituted with proline, valine at position 133 is substituted with glutamic acid, phenylalanine at position 187 is substituted with serine, and serine at position 194 is substituted with arginine in the amino acid residues from position 33 to position 208 (Fc-binding protein containing the amino acid sequence from position 33 to position 208 of the amino acid sequence according to SEQ ID NO: 67).

(h) Fc-binding protein containing the amino acid residues from position 33 to position 208 of the amino acid sequence according to SEQ ID NO: 37, wherein glutamic acid at position 37 is substituted with glycine, leucine at position 39 is substituted with methionine, phenylalanine at position 45 is substituted with isoleucine, glutamine at position 64 is substituted with arginine, serine at position 84 is substituted with proline, valine at position 133 is substituted with glutamic acid, glycine at position 163 is substituted with valine, phenylalanine at position 187 is substituted with serine, and serine at position 194 is substituted with arginine in the amino acid residues from position 33 to position 208 (Fc-binding protein containing the amino acid sequence from position 33 to position 208 of the amino acid sequence according to SEQ ID NO: 69).

(i) Fc-binding protein containing the amino acid residues from position 33 to position 208 of the amino acid sequence according to SEQ ID NO: 37, wherein glutamic acid at position 37 is substituted with glycine, leucine at position 39 is substituted with methionine, phenylalanine at position 45 is substituted with isoleucine, glutamine at position 64 is substituted with arginine, tyrosine at position 67 is substituted with histidine, glutamic acid at position 70 is substituted with aspartic acid, serine at position 84 is substituted with proline, valine at position 133 is substituted with glutamic acid, glycine at position 163 is substituted with valine, phenylalanine at position 187 is substituted with serine, and serine at position 194 is substituted with arginine in the amino acid residues from position 33 to position 208 (Fc-binding protein containing the amino acid sequence from position 33 to position 208 of the amino acid sequence according to SEQ ID NO: 73).

(j) Fc-binding protein containing the amino acid residues from position 33 to position 208 of the amino acid sequence according to SEQ ID NO: 37, wherein glutamic acid at position 37 is substituted with glycine, leucine at position 39 is substituted with methionine, phenylalanine at position 45 is substituted with isoleucine, glutamine at position 64 is substituted with arginine, tyrosine at position 67 is substituted with histidine, glutamic acid at position 70 is substituted with aspartic acid, serine at position 84 is substituted with proline, valine at position 133 is substituted with glutamic acid, threonine at position 156 is substituted with isoleucine, glycine at position 163 is substituted with valine, tyrosine at position 174 is substituted with histidine, lysine at position 181 is substituted with glutamic acid, phenylalanine at position 187 is substituted with serine, and serine at position 194 is substituted with arginine in the amino acid residues from position 33 to position 208 (Fc-binding protein containing the amino acid sequence from position 33 to position 208 of the amino acid sequence according to SEQ ID NO: 77).

(k) Fc-binding protein containing the amino acid residues from position 33 to position 208 of the amino acid sequence according to SEQ ID NO: 37, wherein glutamic acid at position 37 is substituted with glycine, leucine at position 39 is substituted with methionine, phenylalanine at position 45 is substituted with isoleucine, glutamine at position 64 is substituted with arginine, tyrosine at position 67 is substituted with histidine, glutamic acid at position 70 is substituted with aspartic acid, serine at position 84 is substituted with proline, aspartic acid at position 98 is substituted with glutamic acid, glutamine at position 117 is substituted with leucine, valine at position 133 is substituted with glutamic acid, threonine at position 156 is substituted with isoleucine, glycine at position 163 is substituted with valine, tyrosine at position 174 is substituted with histidine, lysine at position 181 is substituted with glutamic acid, phenylalanine at position 187 is substituted with serine, and serine at position 194 is substituted with arginine in the amino acid residues from position 33 to position 208 (Fc-binding protein containing the amino acid sequence from position 33 to position 208 of the amino acid sequence according to SEQ ID NO: 83).

(l) Fc-binding protein containing the amino acid residues from position 33 to position 208 of the amino acid sequence according to SEQ ID NO: 37, wherein glutamic acid at position 37 is substituted with glycine, leucine at position 39 is substituted with methionine, phenylalanine at position 45 is substituted with isoleucine, glutamine at position 64 is substituted with arginine, tyrosine at position 67 is substituted with histidine, glutamic acid at position 70 is substituted with aspartic acid, serine at position 84 is substituted with proline, alanine at position 94 is substituted with serine, aspartic acid at position 98 is substituted with glutamic acid, glutamine at position 117 is substituted with leucine, valine at position 133 is substituted with glutamic acid, threonine at position 156 is substituted with isoleucine, glycine at position 163 is substituted with valine, tyrosine at position 174 is substituted with histidine, lysine at position 181 is substituted with glutamic acid, phenylalanine at position 187 is substituted with serine, serine at position 194 is substituted with arginine, threonine at position 201 is substituted with alanine, and asparagine at position 203 is substituted with aspartic acid in the amino acid residues from position 33 to position 208 (Fc-binding protein containing the amino acid sequence from position 33 to position 208 of the amino acid sequence according to SEQ ID NO: 89).

The Fc-binding protein of the present invention may further have an oligopeptide linked to the N-terminal side or C-terminal side thereof, which is useful for separating from a solution in the presence of an impurity. Examples of the aforementioned oligopeptide include polyhistidine, polylysine, polyarginine, polyglutamic acid and polyaspartic acid. In addition, the Fc-binding protein of the present invention may further have a cysteine containing oligopeptide linked to the N-terminal side or C-terminal side thereof, which is useful for immobilizing the Fc-binding protein on a solid phase such as a chromatographic support. There are no particular limitations on the length of an oligopeptide linked to the N-terminal side or C-terminal side of the Fc-binding protein provided it does not impair the IgG binding ability or stability of the Fc-binding protein of the present invention. When adding the aforementioned oligopeptide to the Fc-binding protein of the present invention, a polynucleotide encoding the oligopeptide may be produced followed by adding it to the N-terminal side or C-terminal side of the Fc-binding protein using a genetic engineering method commonly known among persons with ordinary skill in the art, or the chemically synthesized oligopeptide may be added by chemically bonding to the N-terminal side or C-terminal side of the Fc-binding protein of the present invention. Moreover, a signal peptide for promoting efficient expression in a host may also be linked to the N-terminal side of the Fc-binding protein of the present invention. Examples of the aforementioned signal peptide in the case of using *Escherichia coli* for the host include signal peptides that secrete protein into periplasm in the manner of PelB (SEQ ID NO: 101), DsbA, MalE (region from position 1 to position 26 of the amino acid sequence according to UniProt No. P0AEX9) or TorT (Japanese Unexamined Patent Publication No. 2011-097898).

The Fc-binding protein of the present invention may or may not have a glycan chain. Animal cells, yeast or insect cells and the like are used as hosts in order to obtain Fc-binding protein having a glycan chain. Moreover, the Fc-binding protein may also be modified with an artificially synthesized glycan chain. In addition, a host such as *Escherichia coli* that does not induce the addition of a glycan chain is used for the host in order to obtain Fc-binding protein not having a glycan chain. Moreover, an Fc-binding protein not having a glycan chain can also be obtained by carrying out a procedure that removes the glycan chain from an Fc-binding protein having a glycan chain.

Examples of methods for producing the polynucleotide of the present invention include the following:

(I) a method, wherein the amino acid sequence of the Fc-binding protein of the present invention is converted to a nucleotide sequence, and a polynucleotide containing said nucleotide sequence is artificially synthesized, and (II) a method, wherein polynucleotides containing the entire or partial sequence of an Fc-binding protein is artificially and directly prepared, or is prepared by using a DNA amplification method such as PCR from cDNA of the Fc-binding protein, followed by linking the prepared polynucleotides using a suitable method.

In the method described in (I) above, when converting the nucleotide sequence from the amino acid sequence, it is preferable to carry out conversion in consideration of codon usage frequencies in the host to be transformed. For example, in the case of using *Escherichia coli* for the host, since the usage frequencies of AGA/AGG/CGG/CGA in the case of arginine (Arg), ATA in the case of isoleucine (Ile), CTA in the case of leucine (Leu), GGA in the case of glycine (Gly) and CCC in the case of proline (Pro) are each low (so-called rare codons), conversion is carried out while avoiding these codons. Codon usage frequency can be analyzed by using a public database (such as the Codon Usage Database found on the website of the Kazusa DNA Research Institute).

The error-prone PCR method can be used in the case of introducing a mutation into the polynucleotide of the present invention. There are no particular limitations on the reaction conditions during error-prone PCR provided they allow the introduction of a desired mutation into a polynucleotide encoding Fc-binding protein, as an example thereof, a mutation can be introduced into a polynucleotide by carrying out PCR using different concentrations of four types of substrates in the form of deoxynucleotides (dATP, dTTP, dCTP and dGTP) and adding PCR reaction solution so that the concentration of $MnCl_2$ is from 0.01 mM to 10 mM (and preferably, 0.1 mM to 1 mM). In addition, examples of mutation introduction methods other than error-prone PCR consist of contacting a chemical agent serving as a mutagen with a polynucleotide containing the entire or partial sequence of an Fc-binding protein and allowing to act thereon, irradiating with ultraviolet light, and introducing a mutation into the polynucleotide. A mutagenic chemical agent normally used by persons with ordinary skill in the art is used for the drug used as a mutagen in these methods, examples of which include hydroxylamine, N-methyl-N'-nitro-N-nitrosoguanidine, nitrous acid, sulfurous acid and hydrazine.

There are no particular limitations on the host in which the Fc-binding protein of the present invention is expressed, and examples thereof include animals cells (such as CHO cells, HEK cells, Hela cells or COS cells), yeast (such as *Saccharomyces cerevisiae, Pichia pastoris, Hansenula polymorpha, Schizosaccharomyces japonicus, Schizosaccharomyces octosporus* or *Schizosaccharomyces pombe*), insect cells (such as Sf9 or Sf21), *Escherichia coli* (such as strain JM109, strain BS21(DE3) or strain W3110) and *Bacillus subtilis*. Furthermore, the use of animal cells or *Escherichia coli* as host is preferable in terms of productivity, and the use of *Escherichia coli* for the host is more preferable.

In the case of transforming a host using the polynucleotide of the present invention, although the polynucleotide of the present invention may be used as is, it is more preferable to use the polynucleotide of the present invention inserted at a suitable location in an expression vector (such as a bacteriophage, cosmid or plasmid commonly used to transform prokaryotic and eukaryotic cells). Furthermore, there are no particular limitations on the expression vector provided it is stable within the host to be transformed and is able to replicate, and in the case of using *Escherichia coli* for the host, examples of expression vectors include pET plasmid vector, pUC plasmid vector, pTrc plasmid vector, pCDF plasmid vector and pBBR plasmid vector. In addition, the aforementioned suitable location refers to a location that does not destroy the replication function of the expression vector, desired antibiotic markers or transmissibility. When inserting the polynucleotide of the present invention into the aforementioned expression vector, it is preferably inserted while linked to a promoter or other functional polynucleotide required for expression. Examples of promoters in the case of using *Escherichia coli* for the host include trp promoter, tac promoter, trc promoter, lac promoter, T7 promoter, recA promoter, lpp promoter as well as λ phase promoters in the form of λPL promoter and λPR promoter, while examples thereof in the case of using animals cells for the host include SV40 promoter, CMV promoter and CAG promoter.

A method ordinarily used by persons with ordinary skill in the art is used to transform a host using an expression vector inserted with the polynucleotide of the present invention produced according to the aforementioned method (to be referred to as the "expression vector of the present invention"). For example, in the case of selecting a microorganism belonging to the genus *Escherichia* (such as *Escherichia coli* strain JM109, *Escherichia coli* strain BL21 (DE3) or *Escherichia coli* strain W3110) for the host, the host is transformed according to a known method described in the literature (such as Molecule Cloning, Cold Spring Harbor Laboratory, 256, 1992). Furthermore, electroporation or lipofection is used in the case animal cells are used for the host. A transformant capable of expressing the Fc-binding protein of the present invention (to be referred to as the "transformant of the present invention") can be acquired by screening transformants obtained according to the previously described methods using a suitable method.

In order to prepare the expression vector of the present invention from the transformant of the present invention, the expression vector of the present invention is extracted from the transformant of the present invention using a method suitable for the host used in transformation.

For example, in the case of using *Escherichia coli* for the host of the transformant of the present invention, the transformant is prepared from a culture obtained by culturing the transformant using alkaline extraction or a commercially available extraction kit such as the QIAprep Spin Miniprep Kit (Qiagen).

The Fc-binding protein of the present invention can be produced by culturing the transformant of the present invention and recovering the Fc-binding protein of the present invention from the resulting culture. Furthermore, a culture as referred to in the present description includes not only cells per se of the cultured transformant of the present invention, but also the medium used in culturing. A transformant used in the protein production method of the present invention is cultured in medium suitable for culturing the target host, and in the case the host is *Escherichia coli*, a preferable example of a medium is Luria-Bertani (LB) medium supplemented with required nutrients. Furthermore, a drug corresponding to a drug resistance gene contained in the vector is preferably added to the medium prior to culturing in order to selectively propagate the transformant of the present invention according to the presence or absence of introduction of the expression vector of the present invention. For example, in the case the vector contains a kanamycin resistance gene, kanamycin is added to the medium. In addition, suitable nutrients may also be added to the medium in addition to carbon, nitrogen and inorganic salt sources, and one or more types of reducing agents selected from the group consisting of glutathione, cysteine, cystamine, thioglycolate and dithiothreitol may also be contained as desired. Moreover, a reagent such as glycine that promotes secretion of protein into the culture broth from the aforementioned transformant may also be added, and more specifically, in the case the host is *Escherichia coli*, glycine is preferably added to the medium at 2% (w/v) or less. Although culturing temperature in the case of using *Escherichia coli* for the host is typically 10° C. to 40° C., preferably 20° C. to 37° C. and even more preferably about 25° C., culturing temperature is selected according to the properties of the protein to be expressed. The pH of the medium in the case of using *Escherichia coli* for the host is pH 6.8 to pH 7.4 and preferably around pH 7.0. In addition, in the case an inducible promoter is contained in the vector of the present invention, it is preferably induced under conditions that allow the Fc-binding protein of the present invention to be favorably expressed. An example of inducer is isopropyl-β-D-thiogalactopyranoside (IPTG). In the case the host is *Escherichia coli*, expression of Fc-binding protein can be induced by measuring turbidity of the culture broth (optical absorbance at 600 nm) and continuing culturing after adding a suitable amount of IPTG when turbidity has reached about 0.5 to 1.0. Although the added concentration of IPTG is suitably selected from within the range of 0.005 mM to 1.0 mM, a range of 0.01 mM to 0.5 mM is preferable. Conditions commonly known in the art are used for the various conditions relating to induction by IPTG.

When recovering the Fc-binding protein of the present invention from a culture obtained by culturing the transformant of the present invention, the Fc-binding protein of the present invention is recovered by separating and purifying from the culture using a method suitable for transformation of the Fc-binding protein of the present invention in the transformant of the present invention. For example, in the case of expressing in a culture supernatant, bacterial cells are separated by a centrifugal separation procedure followed by purifying the Fc-binding protein of the present invention from the resulting culture supernatant. In addition, in the case of expressing intracellularly (including periplasm), after harvesting the bacterial cells by a centrifugal separation procedure, the Fc-binding protein of the present invention is extracted by adding an enzymatic treatment agent or surfactant or disrupting the bacterial cells using ultrasonic waves or a French press and then purifying the Fc-binding protein. A method commonly known in the art is used to purifying the Fc-binding protein of the present invention and an example thereof is separation and purification by liquid chromatography. Examples of liquid chromatography include ion exchange chromatography, hydrophobic interaction chromatography, gel filtration chromatography and affinity chromatography, and the Fc-binding protein of the present invention can be prepared at high purity by carrying out a purification procedure that combines these different types of chromatography.

Examples of methods used to measure the binding activity of the resulting Fc-binding protein of the present invention to IgG include measuring binding activity to IgG by enzyme-linked immunosorbent assay (ELISA) and surface plasmon resonance. The IgG used when measuring binding activity is preferably human IgG, and human IgG1 and IgG3 are particularly preferable.

The adsorbent of the present invention can be produced by binding the Fc-binding protein of the present invention to an insoluble support. There are no particular limitations on the aforementioned insoluble support, and examples thereof include supports using a polysaccharide as the raw material thereof in the manner of agarose, alginate, carrageenan, chitin, cellulose, dextrin, dextran or starch, supports using a synthetic polymer as the raw material thereof in the manner of polyvinyl alcohol, polymethacrylate, poly(2-hydroxyethylmethacrylate), polyurethane, polyacrylic acid, polystyrene, polyacrylamide, polymethacrylamide or vinyl polymer, and supports using ceramics as the raw material thereof in the manner of zirconia, zeolite, silica or coating silica. Among these, supports using a polysaccharide as raw material and supports using a synthetic polymer as raw material are preferable as insoluble supports. Examples of the aforementioned preferable supports include polymethacrylate gel introduced with hydroxyl groups such as TOYOPEARL (Tosoh), agarose gel such as Sepharose (GE Healthcare) and cellulose gel such as Cellufine (JNC). There are no particular limitations on the shape of the insoluble support, and may be granular or non-granular or porous or non-porous.

The Fc-binding protein is immobilized on the insoluble support by imparting an active group such as an N-hydroxysuccinimide-activated ester group, epoxy group, carboxyl group, maleimide group, haloacetyl group, tresyl group, formyl group or haloacetoamide group and covalently bonding human Fc-binding protein and the insoluble support through the active group to immobilized on the insoluble support. A commercially available support may be used as is for the support imparted with an active group, or the active group may be introduced onto the support surface under suitable reaction conditions. Examples of commercially available supports imparted with active groups include TOYOPEARL AF-Epoxy-650M, TOYOPEARL AF-Tresyl-650M (both available from Tosoh), HiTrap NHS-Activated HP Columns, NHS-Activated Sepharose 4 Fast Flow and Epoxy-Activated Sepharose 6B (all available from GE Healthcare), and SulfoLink Coupling Resin (available from Thermo Fisher Scientific).

On the other hand, an example of a method for introducing an active group onto the support surface consists of reacting a compound having two or more active sites for a hydroxyl group, epoxy group, carboxyl group or amino group and the like present on the support surface. Examples of compounds that introduce an epoxy group to a hydroxyl group or amino group on the support surface include epichlorhydrin, ethanediol diglycidyl ether, butanediol diglycidyl ether and hexanediol diglycidyl ether. Examples of compounds that introduce a carboxyl group onto the support surface after having introduced by using the aforementioned compounds to introduce an epoxy group onto the support surface include 2-mercaptoacetic acid, 3-mercaptopropionic acid, 4-mercaptobutyric acid, 6-mercaptobutyric acid, glycine, 3-aminopropionic acid, 4-aminobutyric acid and 6-aminohexanoic acid.

Examples of compounds that introduce a maleimide group to a hydroxyl group, epoxy group, carboxyl group or amino group present on the support surface include N-(ε-maleimidocaproic acid) hydrazide, N-(ε-maleimidopropionic acid) hydrazide, 4-[4-N-maleimidophenyl]acetic acid hydrazide, 2-aminomaleimide, 3-aminomaleimide, 4-aminomaleimide, 6-aminomaleimide, 1-(4-aminophenyl) maleimide, 1-(3-aminophenyl) maleimide, 4-(maleimido) phenylisocyanate, 2-maleimidoacetic acid, 3-maleimidopropionic acid, 4-maleimidobutyric acid, 6-maleimidohexanoic acid, (N-[α-maleimidoacetoxy] succinimide ester), (m-maleimidobenzoyl)N-hydroxysuccinimide ester, (succinimidyl-4-[maleimidomethyl]cyclohexane-1-carbonyl-[6-aminohexanoic acid]), (succinimidyl-4-[maleimidomethyl] cyclohexane-1-carboxylic acid), (p-maleimidobenzoyl)N-hydroxysuccinimide ester, (m-maleimidobenzoyl)N-hydroxysuccinimide ester, and N-succinimidyl 3-maleimidopropionate.

Examples of compounds that introduce a haloacetyl group to a hydroxyl group or amino group present on the support surface include chloroacetic acid, bromoacetic acid, iodoacetic acid, chloroacetyl chloride, bromoacetyl chloride, bromoacetyl bromide, chloroacetic anhydride, bromoacetic anhydride, iodoacetic anhydride, 2-(iodoacetoamide)acetic acid-N-hydroxysuccinimide ester, 3-(bromoacetoamide) propionic acid-N-hydroxysuccinimide ester and 4-(iodoacetyl)aminobenzoic acid-N-hydroxysuccinimide ester. Furthermore, another example of a method consists of reacting a ω-alkenyl alkane glycidyl ether with a hydroxyl group or amino group present on the support surface followed by activating the support by halogenating the ω-alkenyl site with a halogenating agent. Examples of ω-alkenyl alkane glycidyl ethers include allyl glycidyl ether, 3-butenyl glycidyl ether and 4-pentenyl glycidyl ether, while examples of halogenating agents include N-chlorosuccinimide, N-bromosuccinimide and N-iodosuccinimide.

Another example of a method for introducing an active group onto the support surface consists of introducing an activating group to a carboxyl group present on the support surface using a condensing agent and an additive. Examples of condensing agents include 1-ethyl-3-(3-dimethylaminopropyl) carbodiimide (EDC), dicyclohexyl carbodiamide and carbonyldiimidazole. In addition, examples of additives include N-hydroxysuccinimide (NHS), 4-nitrophenol and 1-hydroxybenzotriazole.

In addition, examples of compounds that introduce an active group onto the support surface other than those previously described include tresyl chloride (which forms a tresyl group as an activating group) and vinyl bromide (which forms a vinyl group as an activating group).

Examples of buffer solutions used when immobilizing the Fc-binding protein of the present invention on an insoluble support include acetate buffer, phosphate buffer, MES buffer, HEPES buffer, Tris buffer and borate buffer. The reaction temperature during immobilization is suitably set within the temperature range of 5° C. to 50° C. in consideration of the reactivity of the active group and stability of the Fc-binding protein of the present invention, and is preferably within the range of 10° C. to 35° C.

The separation method of the present invention is a method for separating antibodies that comprises a step for equilibrating a column packed with an insoluble support having an Fc-binding protein immobilized thereon by adding an equilibration solution thereto, a step for adding a solution containing antibody to the equilibrated column and adsorbing the antibody to the support, and a step for eluting the antibody adsorbed to the carried using an eluent, wherein the equilibration solution contains chloride ion or sulfate ion at 30 mM or more. According to the present invention, the resolution of the antibody component when calculated as Rs can be improved by a factor of 1.1 to 1.8. Thus, slight differences in antibody molecular structure unable to be detected in the past can now be detected, thereby making it possible to improve the accuracy of analyses. Furthermore, although the concentration of chloride ion or sulfate ion contained in the aforementioned equilibration solution is 30 mM or more, it is preferably 30 mM to 1500 mM, more preferably 30 mM to 1000 mM, even more preferably 30 mM to 500 mM and still more preferably 50 mM to 500 mM.

The aforementioned antibody adsorbed using the aforementioned equilibration solution is eluted using an eluent that reduces affinity between the aforementioned antibody and the Fc-binding protein. An example of such an elution method is a gradient elution method that uses a weakly acidic buffer solution of pH 5.0 to pH 6.9 containing chloride ion or sulfate ion at 30 mM or more for the equilibration solution, and using an acidic buffer solution of pH 2.5 to pH 4.5 for the eluent. The buffering agents are suitably selected from buffering agents commonly known as buffering agents based on the pH of the buffer solution to be produced, and examples thereof include phosphoric acid, acetic acid, formic acid, 2-morpholinoethanesulfonic acid (MES), 3-morpholinopropanesulfonic acid (MOPS), citric acid, succinic acid, glycine and piperazine.

The separation method of the present invention is able to separate antibodies provided the antibodies have affinity for Fc-binding protein and at least contain a glycosylated antibody Fc region. For example, examples of antibodies used in antibody drugs include commonly used chimeric antibodies, humanized antibodies, human antibodies and amino acid substitution products thereof. In addition, structurally modified antibodies, such as bispecific antibodies, fusion antibodies consisting of a glycosylated antibody Fc region and other protein, or conjugates consisting of a glycosylated antibody Fc region and a drug (antibody-drug conjugates, ADC) can also be separated with the separation method of the present invention.

In addition, the separation method of the present invention is able to separate antibodies based on the degree of ADCC activity of adsorbed antibody by adding a buffer solution containing antibody to a column packed with an adsorbent obtained by immobilizing an Fc-binding protein on an insoluble support using a liquid transfer means such as a pump, and adding a suitable eluent to the column after having specifically adsorbed the antibody to the adsorbent. Furthermore, the column is preferably equilibrated using a suitable buffer solution prior to adding the buffer solution containing antibody to the column since this enables the antibody to be separated at higher purity. Examples of buffer solutions include buffer solutions such as phosphate buffer having an inorganic salt as a component thereof. Furthermore, the pH of the buffer solution is from pH 3 to pH 10 and preferably from pH 5 to pH 8. Interaction between the antibody and ligand (Fc-binding protein) is weakened in order to elute antibody adsorbed to the adsorbent based on the degree of ADCC activity, and specific examples of methods used to weaken that interaction include changing pH with a buffer solution, using a counter peptide, changing the temperature and changing salt concentration. Specific examples of eluents for eluting antibody adsorbed to the adsorbent based on the degree of ADCC activity include buffer solutions that are more acidic than the solution used when adsorbing antibody to the adsorbent. Examples of this type of buffer solution include citrate buffer solutions, glycine-HCl buffer solutions and acetate buffer solutions capable of buffering in the acidic range. The pH of the buffer solution is set within a range that does not impair antibody function, and is preferably from pH 2.5 to pH 6.0, more preferably from pH 3.0 to pH 5.0, and even more preferably from pH 3.3 to pH 4.0.

In order to separate glycosylated antibodies using the adsorbent of the present invention by immobilizing the Fc-binding protein of the present invention on an insoluble support, the glycosylated antibody is eluted by, for example, adding a buffer solution containing glycosylated antibody to a column packed with the adsorbent of the present invention using a liquid transfer means such as a pump, and adding a suitable eluent to the column after having specifically adsorbed the glycosylated antibody to the adsorbent of the present invention. Furthermore, the column is preferably equilibrated using a suitable buffer solution prior to adding the buffer solution containing the glycosylated antibody to the column since the glycosylated antibody can be separated at higher purity. Examples of the buffer solution include a buffer solution as phosphate buffer having an inorganic salt as a component thereof. Furthermore, the pH of the buffer solution is from pH 3 to pH 10 and preferably from pH 5 to pH 8. Interaction between the glycosylated antibody and ligand (Fc-binding protein) is weakened in order to elute the glycosylated antibody adsorbed to the adsorbent of the present invention, and specific examples of methods used to weaken that interaction include changing pH with a buffer solution, using a counter peptide, changing the temperature and changing salt concentration. Specific examples of eluents for eluting glycosylated antibody adsorbed to the adsorbent of the present invention include buffer solutions that are more acidic than the solution used when adsorbing the glycosylated antibody to the adsorbent of the present invention. Examples of this type of buffer solution include citrate buffer solutions, glycine-HCl buffer solutions and acetate buffer solutions capable of buffering in the acidic range. The pH of the buffer solution is set within a range that does not impair antibody function, and is preferably from pH 2.5 to pH 6.0, more preferably from pH 3.0 to pH 5.0, and even more preferably from pH 3.3 to pH 4.0.

Furthermore, when separating a glycosylated antibody from a solution containing the glycosylated antibody using the adsorbent of the present invention, the eluting position (eluted fraction) of the antibody differs according to differences in the glycan chain structure of the antibody. Thus, differences in the glycan chain structures of antibodies can be identified by separating antibodies using the adsorbent of the present invention. There are no particular limitations on glycan chain structures able to be identified, and examples thereof include glycan chains added when expressing antibody using cells derived from animals in the manner of CHO cells or yeasts in the manner of *Pichia* species yeast or *Saccharomyces* species yeast as hosts, glycan chains of human antibodies, and glycan chains linked to antibodies using chemical synthesis methods. In addition, since the adsorbent of the present invention is able to separate antibodies based on differences in the glycan chain structure of those antibodies, it can also be used to separate glycan chains per se.

Furthermore, although the adsorbent of the present invention has been previously described as being able to separate antibodies, separate antibodies based on the degree of ADCC activity, and identify differences in the glycan chain structure of antibodies, it can also be used to similarly identify differences in glycan chain structure even in the case of using an Fc receptor other than FcγRIIIa (such as FcγRI, FcγRIIa, FcγRIIb, FcγRIIIa, FcγRIIIb or FcRn) for the Fc-binding protein used for the adsorbent.

Advantageous Effects of Invention

The Fc-binding protein of the present invention is a protein wherein an amino acid residue at a specific position in the extracellular region of human FcγRIIIa is substituted with another amino acid residue. The Fc-binding protein of the present invention has improved stability to heat and acid in comparison with wild-type human FcγRIIIa. Consequently, the Fc-binding protein of the present invention is useful as a ligand of an adsorbent for separating immunoglobulins.

In addition, the separation method of the present invention is able to easily and accurately separate antibodies or molecules containing an antibody Fc region based on pharmacological efficacy by using chromatography. Thus, according to the present invention, production process management and quality control of antibody drugs can be carried out more accurately.

In addition, the separation method of the present invention is able to separate antibodies based on the degree of antibody-dependent cell-mediated toxicity (ADCC) activity by using an adsorbent obtained by immobilizing an Fc-binding protein (such as non-glycosylated human FcγRIIIa) on an insoluble support.

BRIEF DESCRIPTION OF THE DRAWINGS

FIG. 4 is a drawing indicating a list of glycan chain structures linked to antibodies. N1 to N6 in the drawing correspond to N1 to N6 of Table 10, while M1, M2 and D1 correspond to M1, M2 and D1 of Table 11.

EXAMPLES

Figure 1:
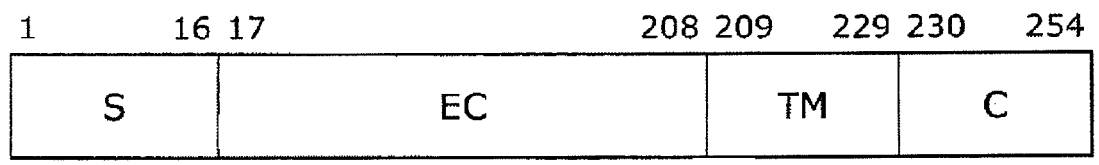
FIG. 1 is a schematic diagram of human FcγRIIIa. The numbers in the drawing indicate the numbers of amino acids as according to SEQ ID NO: 1. S in the drawing indicates a signal sequence, EC indicates an extracellular region, TM indicates a transmembrane region and C indicates an intracellular region.

Although the following indicates examples for providing a more detailed explanation of the present invention, the present invention is not limited to the examples.

Example 1 Construction of Fc-Binding Protein Expression Vector (1) A nucleotide sequence in which the codons were converted from human codons to *Escherichia coli* codons was designed using the DNAworks Method (Nucleic Acids Res., 30, e43, 2002) based on the amino acid sequence from glycine (Gly) at position 17 to glutamine (Gln) at position 192 of the amino acid sequence of human FcγRIIIa according to SEQ ID NO: 1. The designed nucleotide sequence is shown in SEQ ID NO: 2.

(2) In order to construct a polynucleotide containing the sequence according to SEQ ID NO: 2, an oligonucleotide composed of the sequences according to SEQ ID NO: 3 to SEQ ID NO: 20 was synthesized, and the two-step PCR indicated below was carried out using the aforementioned oligonucleotide.

(2-1) In the first stage of PCR, a reaction solution having the composition shown in Table 1 was prepared, and after subjecting the reaction solution to heat treatment for 5 minutes at 98° C., a reaction, in which 1 cycle consisted of a first step carried out for 10 seconds at 98° C., a second step carried out for 5 seconds at 62° C. and a third step carried out for 90 seconds at 72° C., was repeated for 10 cycles to synthesize a polynucleotide designated as FcRp1. Furthermore, the DNA Mix indicated in Table 1 refers to a solution obtained by sampling fixed amounts of each of the 18 types of oligonucleotides composed of the sequences according to SEQ ID NO: 3 to SEQ ID NO: 20 followed by mixing.

TABLE 1

| Composition | Concentration/Volume |
| --- | --- |
| DNA Mix (SEQ ID NOs: 3 to 20) | 2.5 mM each |
| 5x PrimeSTAR buffer (Takara Bio) | 10 µL |
| 2.5 mM dNTPs | 4 µL |
| 2.5 U/µL PrimeSTAR HS (Takara Bio) | 0.5 µL |
| H$_2$O | Up to 50 µL |

(2-2) In the second stage of PCR, the FcRp1 synthesized in (2-1) was used as a template to carry out PCR using oligonucleotides composed of the sequences according to SEQ ID NO: 21 (5'-TAGCCATGGGCATGCGTAC-CGAAGATCTGCCGAAAGC-3') and SEQ ID NO: 22 (5'-CCCAAGCTTAATGATGATGATGATGATGGCCCCTT GGGTAATGGTAATATTCACGGTCTCGCTGC-3') as PCR primers. More specifically, after preparing a reaction solution having the composition shown in Table 2 and subjecting the reaction solution to heat treatment for 5 minutes at 98° C., a reaction, in which 1 cycle consisted of a first step carried out for 10 seconds at 98° C., a second step carried out for 5 seconds at 62° C. and a third step carried out for 90 seconds at 72° C., was repeated for 30 cycles.

TABLE 2

| Composition | Concentration/Volume |
| --- | --- |
| Template DNA | 2 μL |
| Forward primer | 0.4 μM |
| Reverse primer | 0.4 μM |
| 5x PrimeSTAR buffer (Takara Bio) | 10 μL |
| 2.5 mM dNTPs | 4 μL |
| 2.5 U/μL PrimeSTAR HS (Takara Bio) | 0.5 μL |
| H₂O | Up to 50 μL |

(3) After purifying the polynucleotide obtained in (2) and digesting with restriction enzymes NcoI and HindIII, the resulting polynucleotide was ligated to expression vector pETMalE preliminarily digested with restriction enzymes NcoI and HindIII (Japanese Unexamined Patent Publication No. 2011-206046) followed by transforming *Escherichia coli* strain BL21(DE3) using the ligation product.

(4) After culturing the resulting transformant in LB medium containing 50 μg/mL of kanamycin, expression vector pET-eFcR was extracted using the QIAPREP® Spin Miniprep Kit (QIAGEN®).

(5) A polynucleotide encoding human FcγRIIIa and its surrounding regions present in the expression vector pET-eFcR constructed in (4) was subjected to a cycle sequence reaction using the Big Dye Terminator Cycle Sequencing FS Read Reaction Kit (LIFE TECHNOLOGIES®) based on the chain termination method followed by analysis of the nucleotide sequence thereof with a fully-automated DNA sequencer in the form of the ABI PRISM® 3700 DNA Analyzer (LIFE TECHNOLOGIES®). Furthermore, during this analysis, oligonucleotides composed of the sequences according to SEQ ID NO: 23 (5'-TAATACGACTCAC-TATAGGG-3') and SEQ ID NO: 24 (5'-TATGCTAGTTAT-TGCTCAG-3') were used as sequence primers.

The amino acid sequence of the polypeptide expressed with expression vector pET-eFcR is shown in SEQ ID NO: 25, and the sequence of the polynucleotide encoding that polypeptide is shown in SEQ ID NO: 26. Furthermore, in SEQ ID NO: 25, the sequence from methionine (Met) at position 1 to alanine (Ala) at position 26 constitutes an MalE signal peptide, the sequence from lysine (Lys) at position 27 to methionine (Met) at position 32 constitutes a linker sequence, the sequence from glycine (Gly) at position 33 to glutamine (Gln) at position 208 constitutes the extracellular region of human FcγRIIIa (region from position 17 to position 192 of SEQ ID NO: 1), the sequence from glycine (Gly) at position 209 to glycine (Gly) at position 210 constitutes a linker sequence, and the sequence from Histidine (His) at position 211 to histidine (His) at position 216 constitutes a tag sequence.

Example 2 Introduction of Mutation into Fc-Binding Protein and Construction of Library A mutation was randomly introduced into the polynucleotide moiety encoding Fc-binding protein present in the Fc-binding protein expression vector pET-eFcR constructed in Example 1 by error-prone PCR.

(1) Error-prone PCR was carried out using the pET-eFcR constructed in Example 1 as template. Error-prone PCR was carried out by preparing a reaction solution having the composition shown in Table 3 followed by subjecting the reaction solution to heat treatment for 2 minutes at 95° C., carrying out the reaction, in which 1 cycle consisted of a first step carried out for 30 seconds at 95° C., a second step carried out for 30 seconds at 60° C. and a third step carried out for 90 seconds at 72° C., for 35 cycles, and finally subjecting the reaction solution to heat treatment for 7 minutes at 72° C. A mutation was favorably introduced into a polynucleotide encoding Fc-binding protein by the aforementioned error-prone PCR, and the average mutation rate thereof was 1.26%.

TABLE 3

| Composition | Concentration/Volume |
| --- | --- |
| Template DNA (pET-eFcR3) | 0.12 ng/μL |
| 10 μM PCR primer (SEQ ID NO: 21) | 4 μL |
| 10 μM PCR primer (SEQ ID NO: 22) | 4 μL |
| 2.5 mM MgCl₂ | 12 μL |
| 10 mM dATP | 2 μL |
| 10 mM dGTP | 2 μL |
| 10 mM dCTP | 10 μL |
| 10 mM dTTP | 10 μL |
| 10 mM MnCl₂ | 4 μL |
| 10x Ex Taq Buffer (Takara Bio) | x1 |
| GoTaq polymerase (Promega) | 1 μL |
| H₂O | Up to 100 μL |

(2) After purifying the PCR product obtained in (1) and digesting with restriction enzymes NcoI and HindIII, the resulting digested product was ligated to expression vector pETMalE preliminarily digested with restriction enzymes NcoI and HindIII (Japanese Unexamined Patent Publication No. 2011-206046).

(3) Following completion of the ligation reaction, the reaction solution was introduced into *Escherichia coli* strain BL21(DE3) by electroporation, and after culturing on LB plate medium containing 50 μg/mL of kanamycin (18 hours at 37° C.), the colonies that formed on the plate were used as a random mutant library.

Example 3 Screening of Heat-Stabilized Fc-Binding Protein (1) The random mutant library (of transformants) produced in Example 2 was inoculated into 200 μL of 2YT liquid medium (peptone: 16 g/L, yeast extract: 10 g/L, sodium chloride: 5 g/L) containing 50 μg/mL of kanamycin followed by shake culturing overnight at 30° C. using a 96-well deep well plate.

(2) After culturing, 5 μL of the culture broth were subcultured in 500 μL of 2YT liquid medium containing 0.05 mM isopropyl-β-D-thiogalactopyranoside (IPTG), 0.3% glycine and 50 μg/mL of kanamycin, followed by additionally shake culturing overnight at 20° C. using a 96-well deep well plate.

(3) After culturing, the resulting culture supernatant obtained by centrifugation was diluted two-fold with 20 mM Tris-HCl buffer (pH 7.4) containing 150 mM sodium chloride. The diluted solution was subjected to heat treatment for 10 minutes at 45° C.

(4) The antibody binding activity of the Fc-binding protein when subjected to the heat treatment of (3) and the antibody binding activity of the Fc-binding protein when not subjected to the heat treatment of (3) were each measured according to the ELISA procedure indicated below, and residual activity was calculated by dividing the antibody binding activity when the Fc-binding protein was subjected to heat treatment by the antibody binding activity when the Fc-binding protein was not subjected to heat treatment.

(4-1) Human antibody in the form of a gamma-globulin preparation (Chemo-Sero-Therapeutic Research Institute) was immobilized (18 hours at 4° C.) in the wells of a 96-well microplate at 1 μg/well, and following completion of immobilization, the reaction was blocked with 20 mM Tris-HCl buffer (pH 7.4) containing 2% (w/v) skim milk (BD) and 150 mM sodium chloride.

(4-2) After washing the microplate with washing buffer (20 mM Tris-HCl buffer (pH 7.4) containing 0.05% (w/v) Tween 20 and 150 mM NaCl, a solution containing the Fc-binding protein to be evaluated for antibody binding activity was added, and the Fc-binding protein was allowed to react with the immobilized gamma-globulin (1 hour at 30° C.).

(4-3) Following completion of the reaction, the microplate was washed with the aforementioned washing buffer followed by the addition of Anti-6His antibody (Bethyl Laboratories), diluted to 100 ng/mL, at 100 μL/well.

(4-4) After reacting for 1 hour at 30° C. and washing with the aforementioned washing buffer, TMB Peroxidase Substrate (KPL) was added at 50 μL/well. Coloring was interrupted by adding 1 M phosphoric acid at 50 μL/well, and optical absorbance at 450 nm was measured with a microplate reader (Tecan Trading).

(5) Approximately 2700 strains of transformants were evaluated using the method of (4), and those transformants that expressed Fc-binding protein having improved heat stability in comparison with the wild-type Fc-binding protein (without of amino acid substitutions) were selected. The selected transformants were then cultured and expression vectors were prepared using the QIAprep Spin Miniprep Kit (Qiagen).

(6) The nucleotide sequences of the polynucleotide region encoding the Fc-binding protein inserted into the resulting expression vectors were analyzed using the same method as that described in section (5) of Example 1 to identify the positions of amino acid mutations.

The positions of amino acid substitutions and residual activity (%) after heat treatment for the Fc-binding proteins expressed by the transformants selected in (5) and the wild-type (without amino acid substitution) Fc-binding protein are collectively shown in Table 4. Those Fc-binding proteins containing the amino acid residues from glycine at position 17 to glutamine at position 192 in the amino acid sequence according to SEQ ID NO: 1 and having at least one of any of the amino acid substitutions of Met18Arg (in this nomenclature, methionine at position 18 of SEQ ID NO: 1 is substituted with arginine, and to apply similarly hereinafter), Val27Glu, Phe29Leu, Phe29Ser, Leu30Gln, Tyr35Asn, Tyr35Asp, Tyr35Ser, Tyr35His, Lys46Ile, Lys46Thr, Gln48His, Gln48Leu, Ala50His, Tyr51Asp, Tyr51His, Glu54Asp, Glu54Gly, Asn56Thr, Gln59Arg, Phe61Tyr, Glu64Asp, Ser65Arg, Ala71Asp, Phe75Leu, Phe75Ser, Phe75Tyr, Asp77Asn, Ala78Ser, Asp82Glu, Asp82Val, Gln90Arg, Asn92Ser, Leu93Arg, Leu93Met, Thr95Ala, Thr95Ser, Leu110Gln, Arg115Gln, Trp116Leu, Phe118Tyr, Lys119Glu, Glu120Val, Glu121Asp, Glu121Gly, Phe151Ser, Phe151Tyr, Ser155Thr, Thr163Ser, Ser167Gly, Ser169Gly, Phe171Tyr, Asn180Lys, Asn180Ser, Asn180Ile, Thr185Ser and Gln192Lys in the amino acid residues from position 17 to position 192 can be said to have improved heat stability in comparison with the wild-type Fc-binding protein.

TABLE 4

| Amino Acid Substitution | Residual Activity (%) |
|---|---|
| Lys46Ile | 33.6 |
| Gln59Arg | 59.6 |
| Phe61Tyr | 48.2 |
| Glu64Asp | 45.1 |
| Phe75Ser | 47.3 |
| Asp82Glu | 43.1 |
| Asn92Ser | 55.5 |
| Leu93Met | 42.9 |
| Glu121Asp | 46.2 |
| Thr163Ser | 33.2 |
| Asn180Ser | 43.6 |
| Asn180Ile | 50.6 |
| Thr185Ser | 39.3 |
| Met18Arg, Glu64Asp | 53.3 |
| Val27Glu, Tyr35Asn | 96.0 |
| Phe29Leu, Asn56Thr | 38.5 |
| Phe29Ser, Thr95Ala | 58.7 |
| Phe29Leu, Phe118Tyr | 56.6 |
| Leu30Gln, Tyr35Asn | 88.1 |
| Tyr35His, Glu54Asp | 67.1 |
| Tyr35His, Ser155Thr | 65.8 |
| Tyr35Asn, Ser169Gly | 44.8 |
| Lys46Thr, Asn92Ser | 57.6 |
| Ala50His, Thr95Ser | 65.3 |
| Tyr51His, Thr95Ser | 56.5 |
| Asp77Asn, Ala78Ser | 51.7 |
| Gln90Arg, Asn92Ser | 58.8 |
| Phe151Ser, Asn180Lys | 33.0 |
| Phe29Ser, Gln90Arg, Thr163Ser | 46.1 |
| Phe29Leu, Trp116Leu, Phe118Tyr | 81.0 |
| Tyr35Asn, Gln48Leu, Leu110Gln | 74.6 |
| Tyr35Ser, Phe151Tyr, Ser167Gly | 45.0 |
| Tyr35Asn, Glu120Val, Gln192Lys | 75.1 |
| Gln48Leu, Phe75Tyr, Arg115Gln | 38.9 |
| Tyr51Asp, Phe75Leu, Glu121Gly | 94.8 |
| Ala71Asp, Phe75Leu, Glu121Gly | 93.9 |
| Tyr35Asp, Glu54Gly, Asp82Val, Lys119Glu | 63.0 |
| Gln48His, Ser65Arg, Leu93Arg, Phe171Tyr | 44.7 |
| Wild Type | 31.3 |

Among the Fc-binding proteins having amino acid substitutions shown in Table 4, the Fc-binding protein having the highest residual activity and containing the amino acid substitutions of Val27Glu and Tyr35Asn was designated as FcR2, and the expression vector containing the polynucleotide encoding FcR2 was designated as pET-FcR2. The amino acid sequence of FcR2 is shown in SEQ ID NO: 27, while the nucleotide sequence encoding FcR2 is shown in SEQ ID NO: 28. Furthermore, in SEQ ID NO: 27, the sequence from methionine (Met) at position 1 to alanine (Ala) at position 26 constitutes an MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR2 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 27, the glutamic acid of Val27Glu is present at position 43, while the asparagine of Tyr35Asn is present at position 51.

Example 4 Construction of Fc-Binding Proteins Having Amino Acid Substitutions

Stability was attempted to be further improved by integrating those amino acid substitutions determined in Example 3 to be involved in improvement of heat stability of Fc-binding protein. Integration of amino acid substitutions was mainly carried out using PCR and the three types of Fc-binding proteins indicated in (a) to (c) below were produced.

(a) FcR3 obtained by additional amino acid substitution of Phe75Leu in FcR2

(b) FeR4 obtained by additional amino acid substitution of Phe75Leu and Glu121Gly in FcR2

(c) FcR5a obtained by additional amino acid substitution of Asn92Ser in FcR4

The following provides a detailed explanation of the methods used to produce each of the Fc-binding proteins.

(a) FcR3

Val27Glu, Tyr35Asn and Phe75Leu were selected from among the amino acid substitutions clearly determined to be involved in improvement of heat stability in Example 3, and FcR3 was produced in which these substitutions were integrated into wild-type Fc-binding protein. More specifically, FcR3 was produced by introducing a mutation that results in the occurrence of Phe75Leu into a polynucleotide encoding FcR2.

(a-1) PCR was carried out using the pET-FcR2 obtained in Example 3 as template. Oligonucleotides composed of the sequences according to SEQ ID NO: 24 and SEQ ID NO: 29 (5'-AGCCAGGCGAGCAGCTACCTTATTGATGCG-3') were used for the primers in this PCR. After preparing a reaction solution having the composition shown in Table 5, PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 7 minutes at 72° C. The amplified PCR product was subjected to agarose gel electrophoresis and then purified from the gel using the QIAquick Gel Extraction Kit (Qiagen). The purified PCR product was designated as m3F.

TABLE 5

| Composition | Concentration/Volume |
| --- | --- |
| Template DNA | 2 μL |
| 10 μM Forward primer | 1 μL |
| 10 μM Reverse primer | 1 μL |
| 5x PrimeSTAR Buffer (Takara Bio) | 4 μL |
| 2.5 mM dNTPs | 2 μL |
| 2.5 U/μL PrimeSTAR HS (Takara Bio) | 0.5 μL |
| H₂O | Up to 20 μL |

(a-2) PCR was carried out in the same manner as (a-1) with the exception of using the pET-FcR2 obtained in Example 3 as template, and using oligonucleotides composed of the sequences according to SEQ ID NO: 23 and SEQ ID NO: 30 (5'-CCACCGTCGCCGCATCAATAAGG-TAGCTGC-3') as PCR primers. The purified PCR product was designated as m3R.

(a-3) The two PCR products (m3F and m3R) obtained in (a-1) and (a-2) were mixed and a reaction solution having the composition shown in Table 6 was prepared. PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 5 cycles to obtain a PCR product designated as m3p in which m3F and m3R were linked.

TABLE 6

| Composition | Concentration/Volume |
| --- | --- |
| PCR product | Equimolar amounts each |
| 2.5 U/μL PrimeSTAR HS (Takara Bio) | 0.5 μL |
| 5x PrimeSTAR Buffer (Takara Bio) | 4 μL |
| 2.5 mM dNTPs | 2 μL |
| H₂O | Up to 20 μL |

(a-4) PCR was carried out using the PCR product m3p obtained in (a-3) as template and using oligonucleotides composed of the sequences according to SEQ ID NO: 23 and SEQ ID NO: 24 as PCR primers. After preparing a reaction solution having the composition shown in Table 7, PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 30 cycles. As a result, a polynucleotide was constructed that encoded FcR3 having an amino acid substitution introduced at one position in FcR2.

TABLE 7

| Composition | Concentration/Volume |
| --- | --- |
| PCR Product | 2 μL |
| 10 μM Forward primer | 2 μL |
| 10 μM Reverse primer | 2 μL |
| 5x PrimeSTAR Buffer (Takara Bio) | 10 μL |
| 2.5 mM dNTPs | 4 μL |
| 2.5 U/μL PrimeSTAR HS (Takara Bio) | 1 μL |
| H₂O | Up to 50 μL |

(a-5) The polynucleotide obtained in (a-4) was purified followed by digesting with restriction enzymes NcoI and HindIII, ligating to expression vector pETMalE preliminarily digested with restriction enzymes NcoI and HindIII (Japanese Unexamined Patent Publication No. 2011-206046), and using this expression vector to transform Escherichia coli strain BL21(DE3).

(a-6) The resulting transformant was cultured in LB medium containing 50 μg/mL of kanamycin. As a result of extracting plasmid from the harvested bacterial cells (transformant), plasmid pET-FcR3 was obtained that contained a polynucleotide encoding a polypeptide having amino acid substitutions at three positions relative to wild-type Fc-binding protein in the form of FcR3.

(a-7) The nucleotide sequence of pET-FcR3 was analyzed using the same method as in section (5) of Example 1.

The amino acid sequence of FcR3 containing a signal sequence and polyhistidine tag is shown in SEQ ID NO: 31, and the sequence of the polynucleotide encoding the aforementioned FcR3 is shown in SEQ ID NO: 32. Furthermore, in SEQ ID NO: 31, the sequence from methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR3 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 31, the glutamic acid of Val27Glu is present at position 43, the asparagine of Tyr35Asn is present at position 51, and leucine of Phe75Leu is present at position 91.

(b) FcR4

Val27Glu, Tyr35Asn, Phe75Leu and Glu121Gly were selected from among the amino acid substitutions clearly determined to be involved in improvement of heat stability of Fc-binding protein in Example 3, and FcR4 was produced in which these substitutions were integrated into wild-type Fc-binding protein. More specifically, FcR4 was produced by introducing mutations that result in the occurrence of Phe75Leu and Glu121Gly into a polynucleotide encoding FcR2.

(b-1) The PCR product m3R was obtained using the same method as (a-2). In addition, a PCR product m4R was obtained by carrying out PCR using the same method as (a-1) by using a plasmid expressing Fc-binding protein containing the amino acid substitutions of Ala71Asp, Phe75Leu and Glu121Gly (Table 4) obtained in Example 3 as template, and using oligonucleotides composed of the sequences according to SEQ ID NO: 24 and SEQ ID NO: 29 as PCR primers.

(b-2) After mixing the two PCR products (m3R and m4R) obtained according to (b-1), PCR was carried out using the same method as (a-3) to link m3R and m4R. The resulting PCR product was designated as mop.

(b-3) PCR was carried out using the same method as (a-4) by using the PCR product mop obtained in (b-2) as template, and using oligonucleotides composed of the sequences according to SEQ ID NO: 23 and SEQ ID NO: 24 as PCR primers. As a result, a polynucleotide was constructed that encoded FcR4.

(b-4) The polynucleotide obtained in (b-3) was purified followed by digesting with restriction enzymes NcoI and HindIII, ligating to expression vector pETMalE preliminarily digested with restriction enzymes NcoI and HindIII (Japanese Unexamined Patent Publication No. 2011-206046), and using this expression vector to transform *Escherichia coli* strain BL21(DE3).

(b-5) The resulting transformant was cultured in LB medium containing 50 μg/mL of kanamycin. As a result of extracting plasmid from the harvested bacterial cells (transformant), plasmid pET-FcR4 was obtained that contained a polynucleotide encoding a polypeptide having amino acid substitutions at four positions relative to wild-type Fc-binding protein in the form of FcR4.

(b-6) The nucleotide sequence of pET-FcR4 was analyzed using the same method as in section (5) of Example 1.

The amino acid sequence of FcR4 containing a signal sequence and polyhistidine tag is shown in SEQ ID NO: 33, and the sequence of the polynucleotide encoding the aforementioned FcR4 is shown in SEQ ID NO: 34. Furthermore, in SEQ ID NO: 33, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR4 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 33, the glutamic acid of Val27Glu is present at position 43, the asparagine of Tyr35Asn is present at position 51, the leucine of Phe75Leu is present at position 91, and the glycine of Glu121Gly is present at position 137.

(c) FcR5a

Val27Glu, Tyr35Asn, Phe75Leu, Asn92Ser and Glu121Gly were selected from among the amino acid substitutions clearly determined to be involved in improvement of stability of Fc-binding protein in Example 3, and FcR5a was produced in which these substitutions were integrated into wild-type Fc-binding protein. More specifically, FcR5a was produced by introducing a mutation that results in the occurrence of Asn92Ser into a polynucleotide encoding FcR4 produced in (b).

(c-1) PCR was carried out using the same method as (a-1) with the exception of using pET-FcR4 constructed in (b) as template, and using oligonucleotides composed of the sequences according to SEQ ID NO: 22 and SEQ ID NO: 35 (5'-GAATATCGTTGCCAGACCAGCCTGAGCACC-3') as PCR primers. The purified PCR product was designated as m5aF.

(c-2) PCR was then carried out using the same method as (a-1) with the exception of using pET-FcR4 constructed in (b) as template and using oligonucleotides composed of the sequences according to SEQ ID NO: 21 and SEQ ID NO: 36 (5'-GATCGCTCAGGGTGCTCAGGCTGGTCTGGC-3') as PCR primers. The purified PCR product was designated as m5aR.

(c-3) After mixing the two PCR products (m5aF and m5aR) obtained (c-1) and (c-2), PCR was carried out using the same method as (a-3) to link m5aF and m5aR. The resulting PCR product was designated as m5ap.

(c-4) PCR was carried out using the same method as (a-4) by using the PCR product m5ap obtained in (c-3) as template, and using oligonucleotides composed of the sequences according to SEQ ID NO: 21 and SEQ ID NO: 22 as PCR primers. As a result, a polynucleotide was constructed that encoded FcR5a.

(c-5) The polynucleotide obtained in (c-4) was purified followed by digesting with restriction enzymes NcoI and HindIII, ligating to expression vector pETMalE preliminarily digested with restriction enzymes NcoI and HindIII (Japanese Unexamined Patent Publication No. 2011-206046), and using this expression vector to transform *Escherichia coli* strain BL21(DE3).

(c-6) The resulting transformant was cultured in LB medium containing 50 μg/mL of kanamycin. As a result of extracting plasmid from the harvested bacterial cells (transformant), plasmid pET-FcR5a was obtained that contained a polynucleotide encoding a polypeptide having amino acid substitutions at five positions relative to wild-type Fc-binding protein in the form of FcR5a.

(c-7) The nucleotide sequence of pET-FcR5a was analyzed using the same method as in section (5) of Example 1.

The amino acid sequence of FcR5a containing a signal sequence and polyhistidine tag is shown in SEQ ID NO: 37, and the sequence of the polynucleotide encoding the aforementioned FcR5a is shown in SEQ ID NO: 38. Furthermore, in SEQ ID NO: 37, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR5a (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 37, the glutamic acid of Val27Glu is present at position 43, the asparagine of Tyr35Asn is present at position 51, the leucine of Phe75Leu is present at position 91, the serine of Asn92Ser is present at position 108, and the glycine of Glu121Gly is present at position 137.

Example 5 Introduction of Mutation into FcR5a and Construction of Library

A mutation was randomly introduced into the polynucleotide moiety encoding the FcR5a constructed in section (c) of Example 4 by error-prone PCR.

(1) Error-prone PCR was carried out using the expression vector pET-FcR5a constructed in section (c) of Example 4 as template. With the exception of using pET-FcR5a as template, error-prone PCR was carried out by preparing a reaction solution having the composition shown in Table 3 followed by subjecting the reaction solution to heat treatment for 2 minutes at 95° C., carrying out the reaction, in which 1 cycle consisted of a first step carried out for 30 seconds at 95° C., a second step carried out for 30 seconds at 60° C. and a third step carried out for 90 seconds at 72° C., for 35 cycles, and finally subjecting the reaction solution to heat treatment for 7 minutes at 72° C. A mutation was favorably introduced into a polynucleotide encoding Fc-binding protein by this reaction.

(2) After purifying the PCR product obtained in (1) and digesting with restriction enzymes NcoI and HindIII, the resulting PCR product was ligated to expression vector pETMalE preliminarily digested with restriction enzymes NcoI and HindIII (Japanese Unexamined Patent Publication No. 2011-206046).

(3) Following completion of the ligation reaction, the reaction solution was introduced into *Escherichia coli* strain BL21(DE3) by electroporation, and after culturing on LB plate medium containing 50 μg/mL of kanamycin, the colonies that formed on the plate were used as a random mutant library.

Example 6 Screening of Heat-Stabilized Fc-Binding Protein (1) The random mutant library produced in Example 5 was cultured according to the method described in sections (1) and (2) of Example 3 to express Fc-binding protein.

(2) After culturing, the resulting culture supernatant containing Fc-binding protein obtained by centrifugation was diluted 20-fold with pure water, and further diluted 20-fold with 0.1 M sodium carbonate buffer (pH 10.0). Subsequently, the diluted solution was subjected to heat treatment for 15 minutes at 40° C. and the pH was returned to the vicinity of neutrality with 1 M Tris-HCl buffer (pH 7.0).

(3) The antibody binding activity of the Fc-binding protein when subjected to the heat treatment of (2) and the antibody binding activity of the Fc-binding protein when not subjected to the heat treatment of (2) were measured according to the ELISA procedure described in section (4) of Example 3, and residual activity was calculated by dividing the antibody binding activity when the Fc-binding protein was subjected to heat treatment by the antibody binding activity when the Fc-binding protein was not subjected to heat treatment.

(4) Approximately 2700 strains of transformants were evaluated using the method of (3), and those transformants that expressed Fc-binding protein having improved heat stability in comparison with FcR5a were selected. The selected transformants were then cultured in 2YT liquid medium containing 50 μg/mL of kanamycin and expression vectors were prepared using the QIAprep Spin Miniprep Kit (Qiagen).

(5) The nucleotide sequences of the polynucleotide region encoding the Fc-binding protein inserted into the resulting expression vectors were analyzed using the same method as that described in section (5) of Example 1 to identify the positions of amino acid mutations.

The positions of amino acid substitutions and residual activity (%) after heat treatment for the Fc-binding proteins expressed by the transformants selected in (4) relative to FcR5a are collectively shown in Table 8. Those Fc-binding proteins containing the amino acid residues from glycine at position 33 to glutamine at position 208 in the amino acid sequence according to SEQ ID NO: 37 and having at least one of any of the amino acid substitutions of Phe29Ile (in this nomenclature, phenylalanine at position 29 of SEQ ID NO: 1 (position 45 of SEQ ID NO: 37) is substituted with isoleucine, and to apply similarly hereinafter), Phe29Leu, Glu39Gly, Gln48Arg, Tyr51Ser, Phe61Tyr, Asp77Gly, Asp82Glu, Gln90Arg, Gln112Leu, Val117Glu, Lys119Asn, Lys119Glu, Thr140Ile, Leu142Gln, Phe171Ser, Leu175Arg, Asn180Ser and Ile188Val in the amino acid residues from position 33 to position 208 can be said to have improved heat stability in comparison with FcR5a.

TABLE 8

| Amino Acid Substitution | Residual Activity (%) |
|---|---|
| Gln48Arg | 48.7 |
| Asp82Glu | 49.0 |
| Gln112Leu | 56.8 |
| Val117Glu | 52.6 |
| Lys119Asn | 58.6 |
| Leu142Gln | 72.9 |
| Phe171Ser | 58.1 |
| Asn180Ser | 43.9 |
| Ile188Val | 46.5 |
| Phe29Ile, Val117Glu | 57.8 |
| Tyr51Ser, Gln90Arg | 49.6 |
| Phe61Tyr, Lys119Glu, Leu175Arg | 62.1 |
| Phe29Leu, Glu39Gly, Asp77Gly, Thr140Ile | 48.5 |
| FcR5a | 43.4 |

Among the Fc-binding proteins having amino acid substitutions from FcR5a shown in Table 8, the Fc-binding protein containing the amino acid substitutions Phe29Ile and Val117Glu was designated as FcR7a, and the expression vector containing the polynucleotide encoding FcR7a was designated as pET-FcR7a. The amino acid sequence of FcR7a is shown in SEQ ID NO: 39, while the sequence of the nucleotide encoding FcR7a is shown in SEQ ID NO: 40. Furthermore, in SEQ ID NO: 39, the sequence from the methionine (Met) at position 1 to alanine (Ala) at position 26 constitutes an MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR7a (corresponding to the region from position 17 to position 192 of SEQ ID NO: 1), the sequence from position glycine (Gly) at 209 to glycine (Gly) at position 210 constitutes a linker sequence, and the sequence from histidine (His) at position 211 to histidine (His) at position 216 constitutes a tag sequence. In addition, in SEQ ID NO: 39, the isoleucine of Phe29Ile is present at position 45, and the glutamic acid of Val117Glu is present at position 133.

Example 7 Production of Improved Fc-Binding Proteins

Stability was attempted to be further improved by integrating those amino acid substitutions determined in Example 6 to be involved in improvement of heat stability of Fc-binding protein into FcR7a. Integration of amino acid substitutions was mainly carried out using PCR and the four types of Fc-binding proteins indicated in (a) to (d) below were produced.

(a) FcR8 obtained by additional amino acid substitution of Phe171Ser in FcR7a (b) FeR9 obtained by additional amino acid substitution of Gln48Arg in FcR8

(c) FcR10 obtained by additional amino acid substitution of Gln48Arg and Tyr51Ser in FcR8

(d) FcR11 obtained by additional amino acid substitution of Gln90Arg in FcR10

The following provides a detailed explanation of the methods used to produce each of the improved Fc-binding proteins.

(a) FcR8

Phe29Ile, Val117Glu and Phe171Ser were selected from among the amino acid substitutions clearly determined to be involved in improvement of heat stability in Example 6, and FcR8 was produced in which these substitutions were integrated into FcR5a (section (c), Example 4). More specifically, FcR8 was produced by introducing a mutation that results in the occurrence of Phe171Ser into a polynucleotide encoding FcR7a.

(a-1) PCR was carried out using the pET-FcR7a acquired in Example 6 as template. Oligonucleotides composed of the sequences according to SEQ ID NO: 23 and SEQ ID NO: 41 (5'-ACCAGCCCACGGCAGGAATAGCTGCCGCTG-3') were used for the primers in this PCR. After preparing a reaction solution having the composition shown in Table 5, PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 5 minutes at 72° C. The amplified PCR product was subjected to agarose gel electrophoresis and then purified from the gel using the QIAquick Gel Extraction Kit (Qiagen). The purified PCR product was designated as m8F.

(a-2) PCR was carried out in the same manner as (a-1) with the exception of using the pET-FcR7a acquired in Example 6 as template, and using oligonucleotides composed of the sequences according to SEQ ID NO: 42 (5'-GACAGCGGCAGCTATTCCTGCCGTGGGCTG-3') and SEQ ID NO: 24 as PCR primers. The purified PCR product was designated as m8R.

(a-3) The two PCR products (m8F and m8R) obtained in (a-1) and (a-2) were mixed and a reaction solution having the composition shown in Table 6 was prepared. PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 5 cycles to obtain a PCR product designated as m8p in which m8F and m8R were linked.

(a-4) PCR was carried out using the PCR product m8p obtained in (a-3) as template and using oligonucleotides composed of the sequences according to SEQ ID NO: 23 and SEQ ID NO: 24 as PCR primers. After preparing a reaction solution having the composition shown in Table 7, PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 30 cycles. As a result, a polynucleotide was constructed that encoded FcR8 having an amino acid substitution introduced at one position in FcR7a.

(a-5) The polynucleotide obtained in (a-4) was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(a-6) The resulting transformant was cultured in LB medium containing 50 μg/mL of kanamycin. As a result of extracting plasmid from the harvested bacterial cells (transformant), plasmid pET-FcR8 was obtained that contained a polynucleotide encoding a polypeptide having amino acid substitutions at three positions relative to FcR5a (eight positions relative to wild-type Fc-binding protein) in the form of FcR8.

(a-7) The nucleotide sequence of pET-FcR8 was analyzed using the same method as in section (5) of Example 1.

The amino acid sequence of FcR8 containing a signal sequence and polyhistidine tag is shown in SEQ ID NO: 43, and the sequence of the polynucleotide encoding the aforementioned FcR8 is shown in SEQ ID NO: 44. Furthermore, in SEQ ID NO: 43, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR8 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 43, the isoleucine of Phe29Ile is present at position 45 the glutamic acid of Val117Glu is present at position 133, and the serine of Phe171Ser is present at position 187.

(b) RcR9

Phe29Ile, Gln48Arg, Val117Glu and Phe171Ser were selected from among the amino acid substitutions clearly determined to be involved in improvement of heat stability in Example 6, and FcR9 was produced in which these substitutions were integrated into FcR5a (section (c), Example 4). More specifically, FcR9 was constructed by introducing a mutation that results in the occurrence of Gln48Arg into a polynucleotide encoding FcR8.

(b-1) PCR was carried out in the same manner as (a-1) with the exception using the pET-RcR8 constructed in (a) as template, and using oligonucleotides composed of the sequences according to SEQ ID NO: 24 and SEQ ID NO: 45 (5'-GTGACCCTTAAATGCCGGGGCGCGTATAGC-3') as PCR primers. The purified PCR product was designated as m9F.

(b-2) PCR was carried out using the same method as (a-1) with the exception of using the pET-FcR8 constructed in (a) as template, and using oligonucleotides composed of the sequences according to SEQ ID NO: 23 and SEQ ID NO: 46

(5'-CCGGGCTATACGCGCCCCGGCATTTAAGGG-3') as PCR primers. The purified PCR product was designated as m9R.

(b-3) The two PCR products (m9F and m9R) obtained in (b-1) and (b-2) were mixed, and PCR was carried out using the same method as (a-3) to link m9F and m9R. The resulting PCR product was designated as m9p.

(b-4) PCR was carried out using the same method as (a-4) using the PCR product m9p obtained in (b-3) as template and using oligonucleotides composed of the sequences according to SEQ ID NO: 21 and SEQ ID NO: 22 as PCR primers. As a result, a polynucleotide was constructed that encoded FcR9.

(b-5) After purifying the polynucleotide obtained in (b-4), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(b-6) The resulting transformant was cultured in LB medium containing 50 µg/mL of kanamycin. As a result of extracting plasmid from the harvested bacterial cells (transformant), plasmid pET-FcR9 was obtained that contained a polynucleotide encoding a polypeptide having amino acid substitutions at four positions relative to FcR5a (nine positions relative to wild-type Fc-binding protein) in the form of FcR9.

(b-7) The nucleotide sequence of pET-FcR9 was analyzed using the same method as in section (5) of Example 1.

The amino acid sequence of FcR9 containing a signal sequence and polyhistidine tag is shown in SEQ ID NO: 47, and the sequence of the polynucleotide encoding the aforementioned FcR9 is shown in SEQ ID NO: 48. Furthermore, in SEQ ID NO: 47, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR9 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 47, the isoleucine of Phe29Ile is present at position 45, the arginine of Gln48Arg is present at position 64, the glutamic acid of Val117Glu is present at position 133, and the serine of Phe171Ser is present at position 187.

(c) FcR10

Phe29Ile, Gln48Arg, Tyr51Ser, Val117Glu and Phe171Ser were selected from among the amino acid substitutions clearly determined to be involved in improvement of heat stability in Example 6, and FcR10 was produced in which these substitutions were integrated into FcR5a (section (c), Example 4). More specifically, FcR10 was produced by introducing mutations that result in the occurrence of Gln48Arg and Tyr51Ser into a polynucleotide encoding FcR8.

(c-1) PCR was carried out in the same manner as (a-1) with the exception using the pET-RcR8 constructed in (a) as template, and using oligonucleotides composed of the sequences according to SEQ ID NO: 22 and SEQ ID NO: 49 (5'-TGCCGGGGCGCGTCTAGCCCGGAAGATAAC-3') as PCR primers. The purified PCR product was designated as m10F.

(c-2) PCR was carried out using the same method as (a-1) with the exception of using the pET-FcR8 constructed in (a) as template, and using oligonucleotides composed of the sequences according to SEQ ID NO: 21 and SEQ ID NO: 50 (5'-GCTAGACGCGCCCCGGCATTTAAGGGTCAC-3') as PCR primers. The purified PCR product was designated as m10R.

(c-3) The two PCR products (m10F and m10R) obtained in (c-1) and (c-2) were mixed, and PCR was carried out using the same method as (a-3) to link m10F and m10R. The resulting PCR product was designated as m10p.

(c-4) PCR was carried out using the same method as (a-4) using the PCR product m10p obtained in (c-3) as template and using oligonucleotides composed of the sequences according to SEQ ID NO: 21 and SEQ ID NO: 22 as PCR primers. As a result, a polynucleotide was constructed that encoded FcR10.

(c-5) After purifying the polynucleotide obtained in (c-4), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(c-6) The resulting transformant was cultured in LB medium containing 50 µg/mL of kanamycin. As a result of extracting plasmid from the harvested bacterial cells (transformant), plasmid pET-FcR10 was obtained that contained a polynucleotide encoding a polypeptide having amino acid substitutions at five positions relative to FcR5a (ten positions relative to wild-type Fc-binding protein) in the form of FcR10.

(c-7) The nucleotide sequence of pET-FcR10 was analyzed using the same method as in section (5) of Example 1.

The amino acid sequence of FcR10 containing a signal sequence and polyhistidine tag is shown in SEQ ID NO: 51, and the sequence of the polynucleotide encoding the aforementioned FcR10 is shown in SEQ ID NO: 52. Furthermore, in SEQ ID NO: 51, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR10 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 51, the isoleucine of Phe29Ile is present at position 45, the arginine of Gln48Arg is present at position 64, the serine of Tyr51Ser is present at position 67, the glutamic acid of Val117Glu is present at position 133, and the serine of Phe171Ser is present at position 187.

(d) FcR11

Phe29Ile, Gln48Arg, Tyr51Ser, Gln90Arg, Val117Glu and Phe171Ser were selected from among the amino acid substitutions clearly determined to be involved in improvement of heat stability in Example 6, and FcR11 was produced in which these substitutions were integrated into FcR5a (section (c), Example 4). More specifically, FcR11 was produced by introducing a mutation that results in the occurrence of Gln90Arg into a polynucleotide encoding FcR10.

(d-1) PCR was carried out in the same manner as (a-1) with the exception using the pET-RcR10 constructed in (c) as template, and using oligonucleotides composed of the sequences according to SEQ ID NO: 22 and SEQ ID NO: 53 (5'-GGCGAATATCGTTGCCGGACCAGCCTGAGC-3') as PCR primers. The purified PCR product was designated as m11F.

(d-2) PCR was carried out using the same method as (a-1) with the exception of using the pET-FcR10 constructed in (c) as template, and using oligonucleotides composed of the sequences according to SEQ ID NO: 21 and SEQ ID NO: 54 (5'-GGTGCTCAGGCTGGTCCGGCAACGATATTC-3') as PCR primers. The purified PCR product was designated as m11R.

(d-3) The two PCR products (m11F and m11R) obtained in (d-1) and (d-2) were mixed, and PCR was carried out using the same method as (a-3) to link m11F and m11R. The resulting PCR product was designated as m11p.

(d-4) PCR was carried out using the same method as (a-4) using the PCR product m11p obtained in (d-3) as template and using oligonucleotides composed of the sequences according to SEQ ID NO: 21 and SEQ ID NO: 22 as PCR primers. As a result, a polynucleotide was constructed that encoded FcR11.

(d-5) After purifying the polynucleotide obtained in (d-4), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform Escherichia coli strain BL21(DE3).

(d-6) The resulting transformant was cultured in LB medium containing 50 μg/mL of kanamycin. As a result of extracting plasmid from the harvested bacterial cells (transformant), plasmid pET-FcR11 was obtained that contained a polynucleotide encoding a polypeptide having amino acid substitutions at six positions relative to FcR5a (11 positions relative to wild-type Fc-binding protein) in the form of FcR11.

(d-7) The nucleotide sequence of pET-FcR11 was analyzed using the same method as in section (5) of Example 1.

The amino acid sequence of FcR11 containing a signal sequence and polyhistidine tag is shown in SEQ ID NO: 55, and the sequence of the polynucleotide encoding the aforementioned FcR11 is shown in SEQ ID NO: 56. Furthermore, in SEQ ID NO: 55, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR11 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 55, the isoleucine of Phe29Ile is present at position 45, the arginine of Gln48Arg is present at position 64, the serine of Tyr51Ser is present at position 67, the arginine of Gln90Arg is present at position 106, the glutamic acid of Val117Glu is present at position 133, and the serine of Phe171Ser is present at position 187.

Example 8 Evaluation of Acid Stability of Fc-Binding Protein (1) Transformants expressing the wild-type Fc-binding protein produced in Example 1, the Fc-binding protein selected in Example 6 (FcR7a) and the Fc-binding proteins produced in Example 7 (FcR8, FcR9, FcR10 and FcR11) were each inoculated into 3 mL of 2YT liquid medium containing 50 μg/mL of kanamycin followed by shake culturing aerobically overnight at 37° C.

(2) 200 μL of the pre-culture broth were inoculated into 20 mL of 2YT liquid medium (peptone: 16 g/L, yeast extract: 10 g/L, sodium chloride: 5 g/L) containing 50 μg/mL of kanamycin followed by shake culturing aerobically at 37° C.

(3) After culturing for 1.5 hours, the culturing temperature was changed to 20° C. followed by shake culturing for 30 minutes. IPTG was then added to a final concentration of 0.01 mM followed by continuing shake culturing aerobically overnight at 20° C.

(4) Following completion of culturing, the bacterial cells were harvested by centrifugation to prepare a protein extract using the BugBuster Protein Extraction Kit (Takara Bio).

(5) The antibody binding activities of the wild-type Fc-binding protein, FcR7a, FcR8, FcR9, FcR10 and FcR11 in the protein extract prepared in (4) were measured using the ELISA method described in section (4) of Example 3. At this time, concentrations were measured by preparing a calibration curve using a commercially available FcγRIIIa extracellular region (R&D Technologies, 4325-FC-050).

(6) After diluting each of the Fc-binding proteins to a concentration of 30 μg/mL with pure water, 100 μL of the aforementioned diluted solutions and 200 μL of 0.1 M glycine-HCl buffer solution (pH 3.0) were mixed and allowed to stand undisturbed for 2 hours at 30° C.

(7) Antibody binding activity of the proteins after undergoing acid treatment with glycine-HCl buffer solution (pH 3.0) and antibody binding activity of the proteins when not subjected to the aforementioned acid treatment were measured by the ELISA method described in section (4) of Example 3. Subsequently, residual activity was calculated by dividing antibody binding activity in the case of having undergone acid treatment by antibody binding activity in the case of having not undergone acid treatment.

The results are shown in Table 9. The Fc-binding proteins evaluated here (FcR7a, FcR8, FcR9, FcR10 and FcR11) demonstrated higher residual activity in comparison with wild-type Fc-binding protein. On the basis thereof, acid stability of these improved Fc-binding proteins was confirmed to have improved in comparison with the wild type.

TABLE 9

|  | Fc-Binding Protein | | Residual |
| --- | --- | --- | --- |
|  | Name | SEQ ID NO: | Activity (%) |
| Example 6 | FcR7a | 39 | 74.9 |
| Example 7(a) | FcR8 | 43 | 71.8 |
| Example 7(b) | FcR9 | 47 | 81.5 |
| Example 7(c) | FcR10 | 51 | 71.1 |
| Example 7(d) | FcR11 | 55 | 71.2 |
| Example 1 | Wild type | 25 | 19.3 |

Example 9 Construction of FcR5a Having Cysteine Tag (FcR5aCys)

(1) PCR was carried out using the pET-FcR5a constructed in section (c) of Example 4 as template. Oligonucleotides composed of the sequences according to SEQ ID NO: 21 and SEQ ID NO: 57 (5'-CCCAAGCTTATCCGCAGGTATCGT-TGCGGCACCC TTGGGTAATGGTAATATTCACG-GTCTCGCTGC-3') were used as primers in this PCR. After preparing a reaction solution having the composition shown in Table 2, PCR was carried out by subjecting the reaction solution to heat treatment for 5 minutes at 98° C. and repeating a reaction, in which 1 cycle consisted of a first step carried out for 10 seconds at 98° C., a second step carried out for 5 seconds at 55° C. and a third step carried out for 1 minute at 72° C., for 30 cycles.

(2) After purifying the polynucleotide obtained in (1) and digesting with restriction enzymes NcoI and HindIII, the polynucleotide was ligated to expression vector pETMalE preliminarily digested with restriction enzymes NcoI and HindIII (Japanese Unexamined Patent Publication No. 2011-206046) followed by using this ligation product to transform *Escherichia coli* strain BL21(DE3).

(3) After culturing the resulting transformant in LB medium containing 50 μg/mL of kanamycin, expression vector pET-FcR5aCys was extracted using the QIAprep Spin Miniprep Kit (Qiagen).

(4) The nucleotide sequence of pET-FcR5aCys was analyzed using the same method as section (5) of Example 1. The amino acid sequence of the polypeptide expressed with expression vector pET-FcR5aCys is shown in SEQ ID NO: 58, and the sequence of the polynucleotide encoding that polypeptide is shown in SEQ ID NO: 59. Furthermore, in SEQ ID NO: 58, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR5a (corresponding to the region from position 17 to position 192 of SEQ ID NO: 1), and the sequence from glycine (Gly) at position 209 to glycine (Gly) at position 216 constitutes a cysteine tag sequence.

Example 10 Construction of FcR9 Having Cysteine Tag (FcR9Cys)

(1) PCR was carried out using the same method as section (1) of Example 9 with the exception of using the pET-FcR9 constructed in section (b) of Example 7 as template, and using oligonucleotides composed of the sequences according to SEQ ID NO: 21 and SEQ ID NO: 57 as PCR primers.

(2) *Escherichia coli* strain BL21(DE3) was transformed using the same method as section (2) of Example 9.

(3) After culturing the resulting transformant using the same method as section (3) of Example 9, expression vector pET-FcR9Cys was extracted using the QIAprep Spin Miniprep Kit (Qiagen).

(4) The nucleotide sequence of pET-FcR9Cys was analyzed using the same method as section (5) of Example 1.

The amino acid sequence of the polypeptide expressed with expression vector pET-FcR9Cys is shown in SEQ ID NO: 60, and the sequence of the polynucleotide encoding that polypeptide is shown in SEQ ID NO: 61. Furthermore, in SEQ ID NO: 60, the sequence from methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR9 (corresponding to the region from position 17 to position 192 of SEQ ID NO: 1), and the sequence from glycine (Gly) at position 209 to glycine (Gly) at position 216 constitutes a cysteine tag sequence.

Example 11 Preparation of FcR5aCys (1) The transformant expressing FcR5aCys constructed in Example 9 was inoculated into 400 mL of 2YT medium (peptone: 16 g/L, yeast extract: 10 g/L, sodium chloride: 5 g/L) containing 50 μg/mL of kanamycin contained in a 2 L baffled flask followed by pre-culturing by shake culturing aerobically overnight at 37° C.

(2) 180 mL of the culture broth of (1) were inoculated into 1.8 L of liquid medium containing 10 g/L of glucose, 20 g/L of yeast extract, 3 g/L of trisodium phosphate dodecahydrate, 9 g/L of disodium hydrogen phosphate dodecahydrate, 1 g/L of ammonium chloride and 50 mg/L of kanamycin sulfate followed by final culturing using a 3 L fermenter (Biott). Final culturing was begun by setting to conditions consisting of a temperature of 30° C., pH of 6.9 to 7.1, ventilation rate of 1 VVM, and dissolved oxygen concentration of 30% of saturated concentration. The pH was controlled by using acid in the form of 50% phosphoric acid and base in the form of 14% aqueous ammonia, dissolved oxygen was controlled by changing the stirring speed, and the stirring speed was set to a lower limit of 500 rpm and upper limit of 1000 rpm. Following the start of culturing, feed medium (248.9 g/L of glucose, 83.3 g/L of yeast extract and 7.2 g/L of magnesium sulfate heptahydrate) was added while controlling according to the level of dissolved oxygen (DO) at the point glucose concentration was no longer able to be measured.

(3) The culturing temperature was lowered to 25° C. by using the time when optical absorbance at 600 nm (OD600) reached about 150 as an indicator of the number of bacterial cells, and after confirming that the culturing temperature had reached the set temperature, IPTG was added to a final concentration of 0.5 mM followed by continuing culturing at 25° C.

(4) Culturing was discontinued about 48 hours after the start of culturing, and the culture broth was centrifuged for 20 minutes at 4° C. and 8000 rpm to harvest the bacterial cells.

(5) The harvested cells were suspended in 20 mM Tris-HCl buffer (pH 7.0) at 5 mL/1 g (cells) followed by disrupting the cells using an ultrasonic generator (Insonator 201M (trade name), Kubota) at 4° C. for about 10 minutes at an output of about 150 W. The disrupted cell suspension was centrifuged twice for 20 minutes at 4° C. and 8000 rpm followed by collection of the supernatant.

(6) The supernatant obtained in (5) was applied to a VL32×250 column (Merck Millipore) packed with 140 mL of ToyoPearl CM-650M (Tosoh) preliminarily equilibrated with 20 mM Tris-HCl buffer (pH 7.0) at a flow rate of 5 mL/min. After washing with the buffer solution used for equilibration, the column was eluted with 20 mM Tris-HCl buffer (pH 7.0) containing 0.5 M sodium chloride.

(7) The eluate obtained in (6) was applied to an XK26/20 column (GE Healthcare) packed with 90 mL of IgG Sepharose (GE Healthcare) preliminarily equilibrated with 20 mM Tris-HCl buffer (pH 7.4) containing 150 mM sodium chloride. After washing with the buffer solution used for equilibration, the column was eluted with 0.1 M glycine-HCl buffer (pH 3.0). Furthermore, the pH of the eluate was returned to the vicinity of neutrality by adding 1 M Tris-HCl buffer (pH 8.0) at one-fourth the amount of eluate.

About 20 mg of highly pure FcR5aCys was obtained as a result of the aforementioned purification.

Example 12 Preparation of FcR5a-Immobilized Gel and Antibody Separation (1) After activating hydroxyl groups on the surface of 2 mL of a hydrophilic vinyl polymer for use as a separating agent (ToyoPearl, Tosoh) with iodoacetyl groups, a gel having FcR5a immobilized thereon was obtained by reacting 4 mg of the FcR5aCys prepared in Example 11.

(2) 0.5 mL of the FcR5a-immobilized gel prepared in (1) was packed into a stainless steel column measuring 4.6 mm in diameter×75 mm.

(3) The column packed with the FcR5a-immobilized gel was connected to AKTA Explorer (GE Healthcare) and equilibrated with 20 mM acetate buffer solution (pH 4.6).

(4) 0.4 mL of monoclonal antibodies (Rituxan, Zenyaku Kogyo) diluted to 0.5 mg/mL with 20 mM acetate buffer solution (pH 4.6) were applied to the column at a flow rate of 0.2 mL/min.

(5) After washing the column with equilibration buffer for 25 minutes while maintaining the flow rate at 0.2 mL/min, adsorbed monoclonal antibodies were eluted at a pH gradient generated with 20 mM glycine-HCl buffer (pH 3.0) (gradient at which 100% of the 20 mM glycine-HCl buffer (pH 3.0) elutes in 25 minutes).

Figure 2:
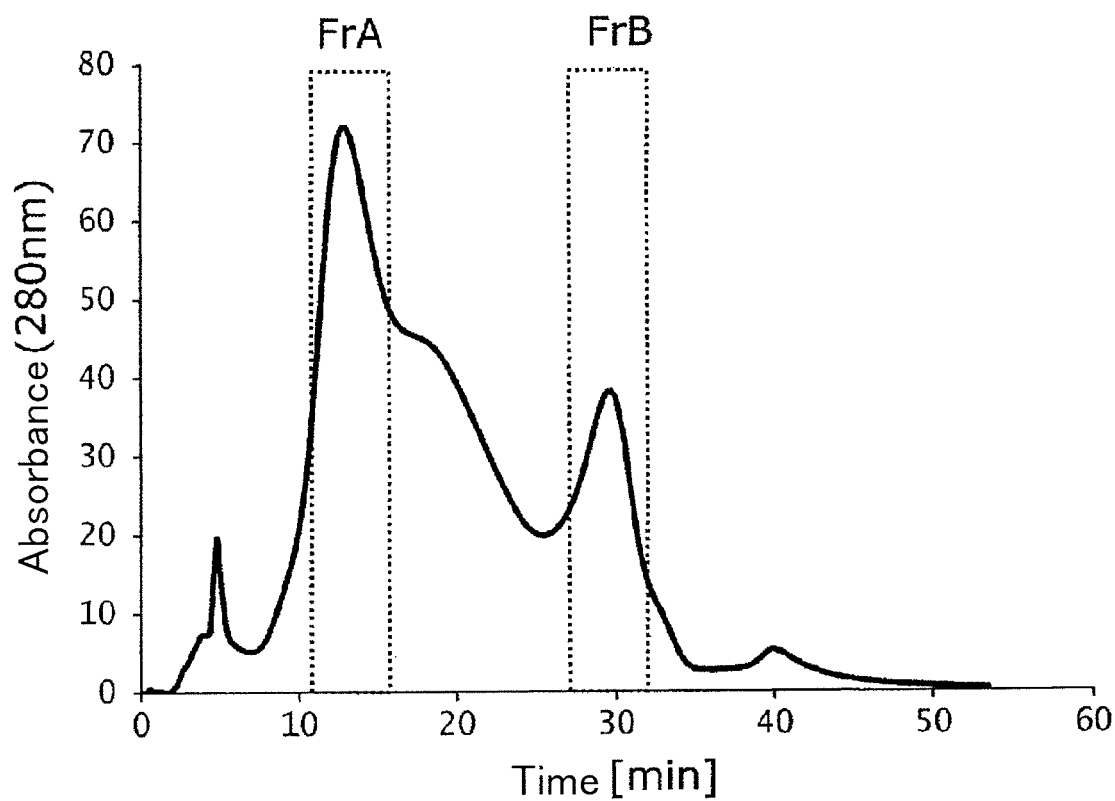
FIG. 2 is a drawing indicating the elution pattern of an antibody using FcR5a-immobilized gel. FrA and FrB in the drawing indicate the positions of Fraction A and Fraction B, respectively.

The results (elution pattern) are shown in FIG. 2. As a result of interacting with FcR5a, the monoclonal antibodies were separated into multiple peaks instead of a single peak in the manner of gel filtration chromatography.

Example 13 Measurement of Antibody-Dependent Cell-Medicated Cytotoxicity (ADCC) Activity of Antibodies Separated with FcR5a-Immobilized Gel (1) The monoclonal antibodies that eluted under the conditions described in Example 12 were separated and fractionated into Fraction A (FrA) and Fraction B (FrB) in the elution pattern indicated in FIG. 2.

(2) The buffer solution was exchanged with phosphate buffered saline (PBS) (pH 7.4) while concentrating the fractionated FrA and FrB with an ultrafiltration membrane (Merck Millipore).

(3) The concentrations of antibodies contained in the FrA and FrB subjected to concentration and buffer exchange and monoclonal antibodies prior to separation were measured at an optical absorbance of 280 nm.

(4) The ADCC activities of antibodies contained in FrA and FrB were measured according to the method indicated below.

(4-1) An 8-step dilution series was prepared at dilution factor of ⅓ from 3 μg/mL of the antibodies contained in FrA and FrB and the monoclonal antibodies prior to separation using ADCC assay buffer prepared by mixing 1.4 mL of low IgG serum and 33.6 mL of RPMI1640 medium.

(4-2) Raji cells were prepared to a concentration of about $5 \times 10^5$ cells/mL with ADCC assay buffer and added to a 96-well plate (3917, Corning) at 25 μL/well.

(4-3) The Fraction A, Fraction B and monoclonal antibodies prior to separation prepared in (4-1) along with a blank (ADCC assay buffer) were added to the wells containing Raji cells at 25 μL/well.

(4-4) Effector cells (Promega) were prepared at a concentration of about $3.0 \times 10^5$ cells/mL with ADCC assay buffer and added to the wells containing Raji cells and antibodies at 25 μL/well. Subsequently, the plate was allowed to stand undisturbed for 6 hours in a $CO_2$ incubator (5% $CO_2$, 37° C.)

(4-5) After allowing the 96-well plate to stand undisturbed for 5 minutes to 30 minutes at room temperature, Luciferase Assay Reagent (Promega) was added at 75 μL/well. After allowing to react for 30 minutes at room temperature, luminescence was measured with the GloMax Multi Detection System (Promega).

Figure 3:
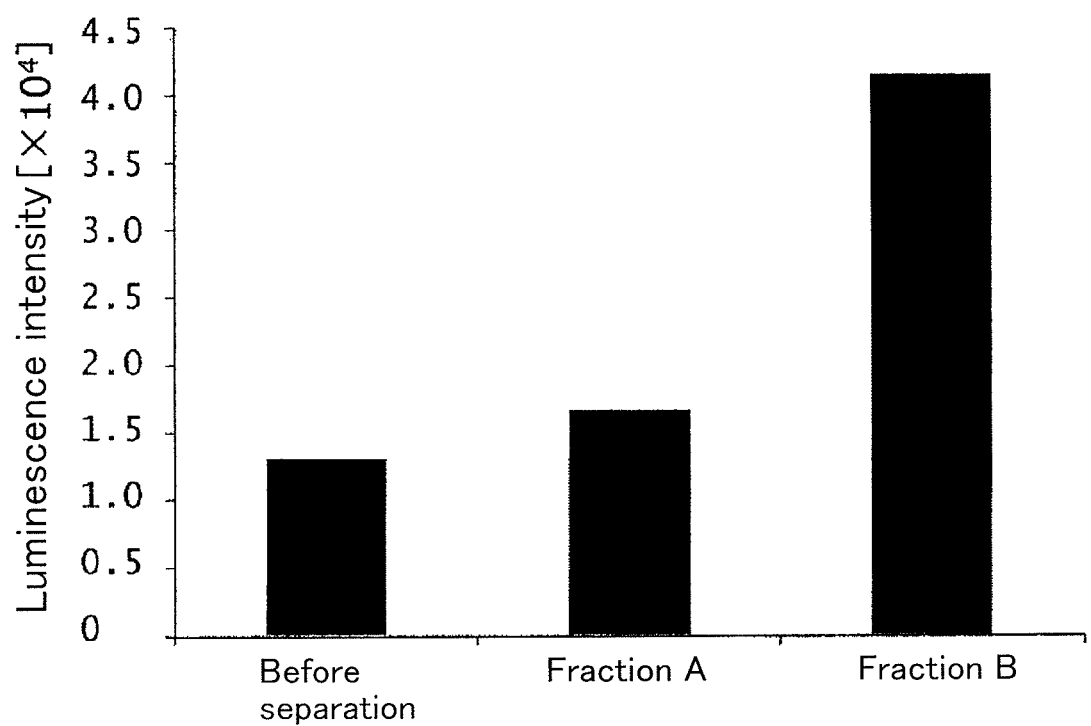
FIG. 3 is a drawing indicating the results of measuring the ADCC activity of antibody separated with FcR5a-immobilized gel.

The results of comparing the luminescence intensities of the FrA and FrB, fractionated under the elution conditions described in Example 12, and the monoclonal antibodies prior to separation are shown in FIG. 3. Furthermore, the results of FIG. 3 indicate values obtained by subtracting the luminescence intensity of the blank from the measured luminescence intensity, and higher luminescence intensity indicates greater ADCC activity.

ADCC activity of FrA can be said to be roughly equal to that of the monoclonal antibodies prior to separation since FrA demonstrated luminescence intensity nearly equal thereto. On the other hand, FrB demonstrated ADCC activity that was superior to the monoclonal antibodies prior to separation by a factor of about 3.2 and superior to FrA by a factor of about 2.5. In other words, FrB was determined to demonstrate a higher level of ADCC activity in comparison with the monoclonal antibodies prior to separation and FrA.

Example 14 Glycan Chain Analysis of Antibodies Separated with FcR5a-Immobilized Gel (1) After denaturing the FrA and FrB fractionated in section (1) of Example 13 along with the monoclonal antibodies prior to separation by heat-treating for 10 minutes at 100° C., the antibodies were sequentially treated with pronase and a mixture of glycoamidase A and pepsin to acquire glycan chain fractions after going through a purification procedure by gel filtration.

(2) After concentrating and drying the glycan chains obtained in (1) with an evaporator, the antibodies were sequentially acted on by 2-aminopyridine and then borane dimethylamine in the presence of acetic acid solvent to obtain fluorescently labeled glycan chains followed by purification by gel filtration.

(3) The fluorescently labeled glycan chains obtained in (2) were separated into a neutral glycan chain fraction and mono-sialylated glycan chain fraction with an anion exchange column (TSKgel DEAE-SPW, diameter 7.5 mm×7.5 cm, Tosoh).

(4) The neutral glycan chain fraction and mono-sialylated glycan chain fraction obtained in (3) were isolated into individual glycan chains using an ODS column. After acquiring information on the molecular weights of the glycan chains isolated by MALDI-TOF-MS analysis, the glycan chains were assigned structures by comparing with the retention times of ODS column chromatography.

The assigned glycan chain structures (N1 to N6, M1, M2 and D1) are shown in FIG. 4, the composite ratios of the neutral glycan chains are shown in Table 10, and the composite ratios of mono-silylated and di-silylated glycan chains are shown in Table 11. Antibodies having the glycan chain structure N4+N4' or N6 were increased in FrB in comparison with the pre-separation antibodies and FrA. On the other hand, antibodies having the structure N1, N2+N3', N3 or N5 were decreased in FrB in comparison with the pre-separation antibodies and FrA. Namely, antibodies having N4+N4' and N6 glycan chains were identified to bind strongly to FcR5a, while antibodies having N1, N2+N3', N3 and N5 glycan chains were identified to exhibit weak binding to FcR5a. In addition, antibodies having M1, M2 or D1 glycan chains were increased in FrB in comparison with the pre-separation antibodies and FrA. Namely, antibodies having M1, M2 and D1 glycan chains were identified to bind strongly to FcR5a.

TABLE 10

| Structure No. in FIG. 4 | Pre-Separation Antibodies (composite ratio, %) | FrA (composite ratio, %) | FrB (composite ratio, %) |
|---|---|---|---|
| N1 | 1.5 | 1.2 | Not detected |
| N2 + N3' | 5.4 | 5.9 | 3.0 |
| N3 | 45.0 | 64.2 | 16.4 |
| N4 + N4' | 32.6 | 15.4 | 57.6 |
| N5 | 6.6 | 9.9 | 3.6 |
| N6 | 5.4 | 1.7 | 12.7 |

N3' is the epimerized glycan chain of N3.
N4' is the epimerized glycan chain of N4.

TABLE 11

| Structure No. in FIG. 4 | Pre-separation antibodies (composite ratio: %) | FrA (composite ratio, %) | FrB (composite ratio, %) |
|---|---|---|---|
| M1 | 0.5 | 0.2 | 0.9 |
| M2 | 1.5 | 0.3 | 2.9 |
| D1 | 0.6 | Not detected | 1.6 |

When a comparison is made between the above results and the results of Example 13, antibodies having a glycan chain structure associated with an increase in FrB in comparison with pre-separated antibodies and FrA were identified to demonstrate a high level of ADCC activity.

Namely, FcR5A-immobilized gel was determined to enable identification of differences in antibody glycan chain structures while also making it possible to separate antibodies having a high level of ADCC activity based on that identification.

Example 15 Preparation of FcR9-Immobilized Gel and Antibody Separation (1) Culturing was carried out in the same manner as sections (1) to (4) of Example 11 using the transformant expressing FcR9Cys constructed in Example 10.

(2) About 10 mg of highly pure FcR9Cys was obtained by purifying using the same method as Example 11.

(3) FcR9Cys-immobilized gel was obtained using the same method as section (1) of Example 12 followed by packing 0.5 mL of the gel into a stainless steel column measuring 4.0 mm in diameter×40 mm.

(4) The column packed with the FcR9-immobilized gel was connected to a high-performance chromatograph and equilibrated with 20 mM acetate buffer solution (pH 4.5).

(5) 0.15 mL of monoclonal antibodies (Rituxan, Zenyaku Kogyo) diluted to 4.0 mg/mL with phosphate-buffered saline (PBS) (pH 7.4) were applied to the column at a flow rate 0.3 mL/min.

(6) After washing the column with equilibration buffer for 2 minutes while maintaining the flow rate at 0.3 mL/min, adsorbed monoclonal antibodies were eluted at a pH gradient generated with 10 mM glycine-HCl buffer (pH 3.0) (gradient at which 100% of the 10 mM glycine-HCl buffer (pH 3.0) elutes in 38 minutes).

Figure 5:
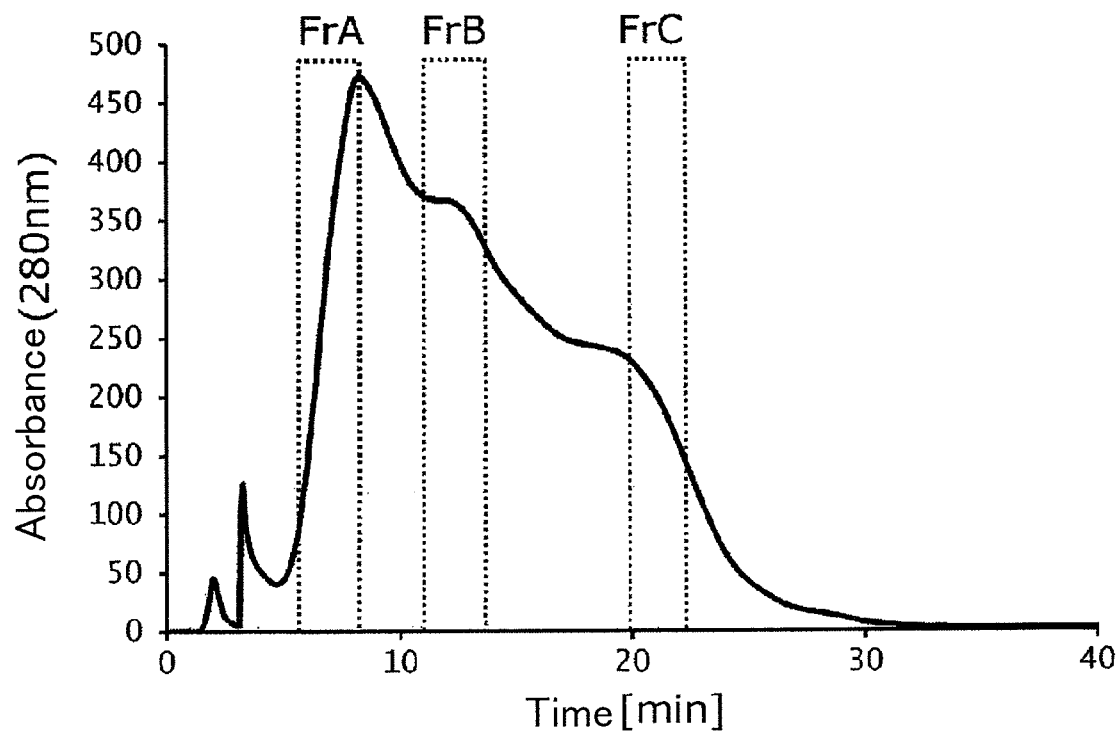
FIG. 5 is a drawing indicating the elution pattern of an antibody using FcR9-immobilized gel. FrA, FrB and FrC in the drawing indicate the positions of Fraction A, Fraction B and Fraction C, respectively.

The results (elution pattern) are shown in FIG. 5. As a result of interacting with FcR9, the monoclonal antibodies were separated into multiple peaks instead of a single peak in the manner of gel filtration chromatography.

Example 16 Measurement of ADCC Activity of Antibodies Separated with FcR9-Immobilized Gel (1) The monoclonal antibodies that eluted under the conditions described in Example 15 were separated and fractionated into Fraction A (FrA), Fraction B (FrB) and Fraction C (FrC) in the elution pattern indicated in FIG. 5.

(2) The concentrations of antibodies contained in FrA, FrB and FrC and monoclonal antibodies prior to separation were measured at an optical absorbance of 280 nm, and ADCC activities were measured using the same method as section (4) of Example 13.

Figure 6:
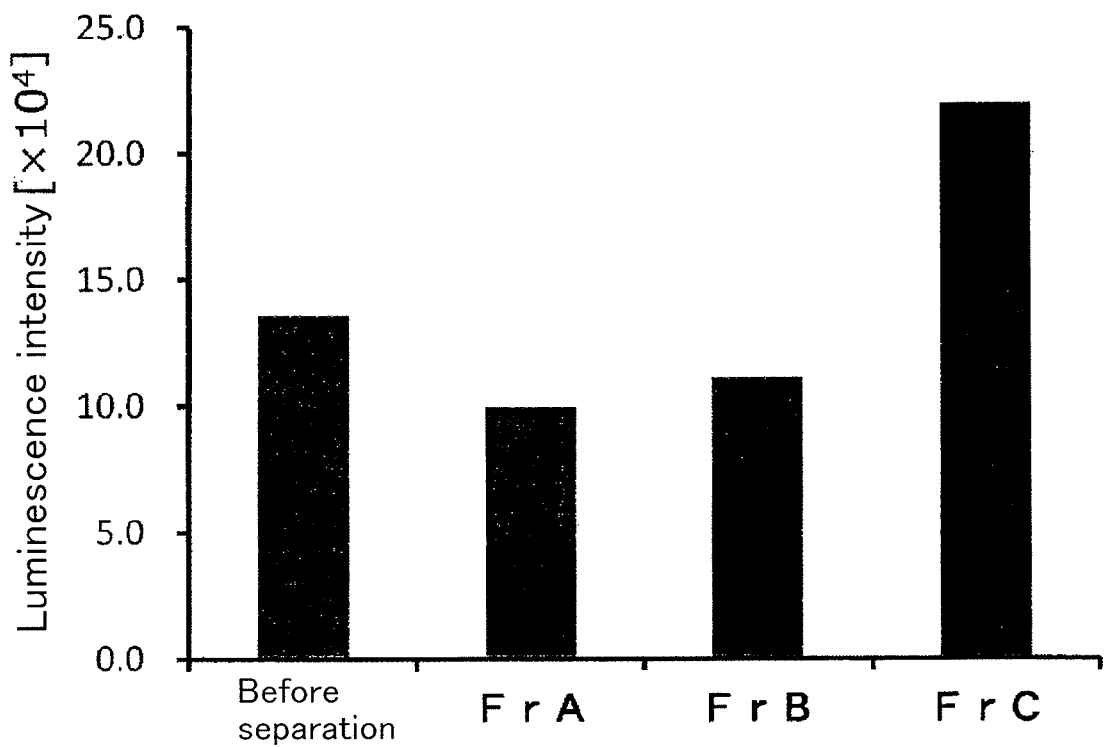
FIG. 6 is a drawing indicating the results of measuring the ADCC activity of antibody separated with FcR9-immobilized gel.

The results are shown in FIG. 6. Furthermore, the results of FIG. 6 indicate values obtained by subtracting the luminescence intensity of the blank from the measured luminescence intensity, and higher luminescence intensity indicates greater ADCC activity.

The ADCC activity of FrA and FrB can be said to be somewhat lower than the pre-separation monoclonal antibodies. On the other hand, FrC demonstrated ADCC activity that was superior to that of the pre-separation monoclonal antibodies by a factor of about 1.6. In other words, the late-eluting FrC was determined to demonstrate a higher level of ADCC activity in comparison with the early-eluting FrA and FrB as well as the pre-separation monoclonal antibodies. In addition, since gel having the Fc-binding protein of the present invention immobilized thereon is capable of identifying differences in antibody glycan chain structure according to Example 14, antibodies that strongly bind to FcR9 included in FrC are suggested to have a glycan chain structure having a high level of ADCC activity.

Example 17 Introduction of Mutation into FcR9 and Construction of Library

A mutation was randomly introduced into the polynucleotide moiety encoding the FcR9 constructed in section (b) of Example 7 by error-prone PCR.

(1) Error-prone PCR was carried out using the pET-FcR9 constructed in section (b) of Example 7 as template. In addition to using pET-FcR9 as template and using oligonucleotides composed of the sequences according to SEQ ID NO: 23 and SEQ ID NO: 24 as primers, error-prone PCR was carried out by preparing a reaction solution having the same composition as that shown in Table 3, followed by subjecting the reaction solution to heat treatment for 2 minutes at 95° C., carrying out the reaction, in which 1 cycle consisted of a first step carried out for 30 seconds at 95° C., a second step carried out for 30 seconds at 50° C. and a third step carried out for 90 seconds at 72° C., for 35 cycles, and finally subjecting the reaction solution to heat treatment for 7 minutes at 72° C. A mutation was favorably introduced into a polynucleotide encoding Fc-binding protein by this reaction.

(2) After purifying the PCR product obtained in (1) and digesting with restriction enzymes NcoI and HindIII, the resulting digested product was ligated to expression vector pETMalE preliminarily digested with the same restriction enzymes (Japanese Unexamined Patent Publication No. 2011-206046).

(3) Following completion of the ligation reaction, the reaction solution was introduced into *Escherichia coli* strain BL21(DE3) by electroporation, and after culturing on LB plate medium containing 50 μg/mL of kanamycin, the colonies that formed on the plate were used as a random mutant library.

Example 18 Screening of Alkaline-Stabilized Fc-Binding Protein (1) The random mutant library produced in Example 17 was cultured according to the method described in sections (1) and (2) of Example 3 to express Fc-binding protein.

(2) After culturing, culture supernatant containing Fc-binding protein obtained by centrifugation was diluted 10-fold with pure water and subjected to alkaline treatment by mixing with an equal amount of 60 mM aqueous sodium hydroxide solution and allowing to stand undisturbed for 1.5 hours at 30° C. Subsequently, the pH was returned to the vicinity of neutrality with four volumes of 1 M Tris-HCl buffer (pH 7.0).

(3) The antibody binding activity of the Fc-binding protein when subjected to the alkaline treatment described in (2) and the antibody binding activity of the Fc-binding protein when not subjected to the alkaline treatment described in (2) were each measured according to the ELISA procedure described in section (4) of Example 3, and residual activity was calculated by dividing the antibody binding activity when the Fc-binding protein was subjected to alkaline treatment by the antibody binding activity when the Fc-binding protein was not subjected to alkaline treatment.

(4) Approximately 2700 strains of transformants were evaluated using the method of (3), and those transformants that expressed Fc-binding protein having improved stability in comparison with FcR9 were selected. The selected transformants were then cultured in 2YT liquid medium containing 50 μg/mL of kanamycin, and expression vectors were prepared using the QIAprep Spin Miniprep Kit (Qiagen).

(5) The nucleotide sequences of the polynucleotide region encoding the Fc-binding protein inserted into the resulting expression vectors were analyzed according to the method described in section (5) of Example 1 to identify the positions of amino acid mutations.

The positions of amino acid substitutions with respect to FcR9 and residual activity (%) after alkaline treatment of the Fc-binding proteins expressed by the transformants selected in (4) are collectively shown in Table 12. Those Fc-binding proteins containing the amino acid residues from glycine at position 33 to glutamine at position 208 in the amino acid sequence according to SEQ ID NO: 37 and having at least one of any of the amino acid substitutions of Met18Ile (in this nomenclature, methionine at position 18 of SEQ ID NO: 1 (position 37 of SEQ ID NO; 37) is substituted with isoleucine, and to apply similarly hereinafter), Glu21Lys, Glu21Gly, Leu23Met, Gln33Pro, Lys46Glu, Phe61Tyr, Glu64Gly, Ser65Arg, Ser68Pro, Asp77Val, Asp77Glu, Val81Met, Asp82Ala, Gln101Leu, Glu103Val, His105Arg, Glu120Val, Ser178Arg and Asn180Lys in the amino acid residues from position 33 to position 208 can be said to have improved alkaline stability in comparison with FcR9.

TABLE 12

| Amino Acid Substitution | Residual Activity (%) |
| --- | --- |
| Glu21Lys | 74.4 |
| Glu21Gly | 91.2 |
| Leu23Met | 83.3 |
| Ser65Arg | 73.2 |
| Ser68Pro | 92.9 |
| Asp77Val | 75.9 |
| Val81Met | 71.2 |
| Glu103Val | 75.5 |
| Glu120Val | 75.4 |
| Ser178Arg | 93.5 |
| Asn180Lys | 94.8 |
| Gln33Pro, Ser178Arg | 97.2 |
| Lys46Glu, Phe61Tyr | 89.9 |
| Met18Ile, Glu120Val | 98.7 |
| Asp82Ala, Gln101Leu | 71.0 |
| Glu64Gly, Asp77Glu, His105Arg | 87.4 |
| FcR9 | 66.4 |

Example 19 Construction of Improved Fc Binding Proteins

Stability was attempted to be further improved by integrating those amino acid substitutions determined in Example 18 to be involved in improvement of alkaline stability of Fc-binding protein into FcR9. Integration of amino acid substitutions was mainly carried out using PCR and the two types of Fc-binding proteins indicated in (a) and (b) below were produced.

(a) FcR12 obtained by additional amino acid substitution of Glu21Gly, Leu23Met and Ser178Arg in FcR9

(b) FeR13 obtained by additional amino acid substitution of Glu21Gly, Leu23Met, Ser68Pro and Ser178Arg in FcR9

The following provides a detailed explanation of the methods used to produce each of the improved Fc-binding proteins.

(a) FcR12

Glu21Gly, Leu23Met and Ser178Arg were selected from among the amino acid substitutions clearly determined to be involved in improvement of alkaline stability in Example 18, and FcR12 was produced in which these substitutions were integrated into FcR9 (section (b), Example 7). More specifically, FcR12 was produced by introducing mutations that result in the occurrence of Glu21Gly and Leu23Met into a polynucleotide containing the mutation of Ser178Arg obtained in Example 18.

(a-1) PCR was carried out using the polynucleotide obtained in Example 18 that encodes Fc-binding protein containing the mutation of Ser178Arg in FcR9. Oligonucleotides composed of the sequences according to SEQ ID NO: 24 and SEQ ID NO: 62 (5'-CTAGCCATGGGCATGCG-TACCGGAGATATGCCGAAAGCGGAG-3') were used for the primers in this PCR. With the exception of the template and primers, after preparing a reaction solution having the composition shown in Table 7, PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 5 minutes at 72° C. The amplified PCR product was subjected to agarose gel electrophoresis and then purified from the gel using the QIAquick Gel Extraction Kit (Qiagen). The purified PCR product was designated as m12p.

(a-2) The m12p obtained in (a-1) was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform Escherichia coli strain BL21 (DE3).

(a-3) The resulting transformant was cultured in LB medium containing 50 µg/mL of kanamycin. As a result of extracting plasmid from the harvested bacterial cells (transformant), plasmid pET-FcR12 was obtained that contained a polynucleotide encoding a polypeptide having amino acid substitutions at three positions relative to FcR9 (12 positions relative to wild-type Fc-binding protein) in the form of FcR12.

(a-4) The nucleotide sequence of pET-FcR12 was analyzed using the same method as in section (5) of Example 1.

The amino acid sequence of FcR12 containing a signal sequence and polyhistidine tag is shown in SEQ ID NO: 63, and the sequence of the polynucleotide encoding the aforementioned FcR12 is shown in SEQ ID NO: 64. Furthermore, in SEQ ID NO: 63, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR12 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 63, the glycine of Glu21Gly is present at position 37, the methionine of Leu23Met is present at position 39, the glutamic acid of Val27Glu is present at position 43, the isoleucine of Phe29Ile is present at position 45, the asparagine of Tyr35Asn is present at position 51, the arginine of Gln48Arg is present at position 64, the leucine of Phe75Leu is present at position 91, the serine of Asn92Ser is present at position 108, the glutamic acid of Val117Glu is present at position 133, the glycine of Glu121Gly is present at position 137, the serine of Phe171Ser is present at position 187, and the arginine of Ser178Arg is present at position 194.

(b) FcR13

Glu21Gly, Leu23Met, Ser68Pro and Ser178Arg were selected from among the amino acid substitutions clearly determined to be involved in improvement of alkaline stability in Example 18, and FcR13 was produced in which these substitutions were integrated into FcR9 (section (b), Example 7). More specifically, FcR13 was produced by introducing a mutation that results in the occurrence of Ser68Pro into a polynucleotide encoding FcR12.

(b-1) In addition to using the pET-Fc12 constructed in (a) as template and using oligonucleotides composed of the sequences according to SEQ ID NO: 24 and SEQ ID NO: 65 (5'-CACAATGAAAGCCTGATTCCCAGCCAGGCG-3') as PCR primers, after preparing a reaction solution having the composition shown in Table 5, PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 5 minutes at 72° C. The amplified PCR product was subjected to agarose gel electrophoresis and then purified from the gel using the QIAquick Gel Extraction Kit (Qiagen). The purified PCR product was designated as m13F.

(b-2) PCR was carried out using the same method as (b-1) with the exception of using the pET-FcR12 constructed in (a) as template, and using oligonucleotides composed of the sequences according to SEQ ID NO: 62 and SEQ ID NO: 66 (5'-GTAGCTGCTCGCCTGGCTGGGAATCAGGCT-3') as PCR primers. The purified PCR product was designated as m13R.

(b-3) The two PCR products (m13F and m13R) obtained in (b-1) and (b-2) were mixed and a reaction solution having the composition shown in Table 6 was prepared. PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 5 cycles, and finally subjecting to heat treatment for 5 minutes at 72° C. to link m13F and m13R. The resulting PCR product was designated as m13p.

(b-4) PCR was carried out using the PCR product m13p obtained in (b-3) as template and using oligonucleotides composed of the sequences according to SEQ ID NO: 23 and SEQ ID NO: 24 as PCR primers. After preparing a reaction solution having the composition shown in Table 7, PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 30 cycles. As a result, a polynucleotide was constructed that encoded FcR13 having an amino acid substitution introduced at one position in FcR12.

(b-5) The polynucleotide obtained in (b-4) was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(b-6) The resulting transformant was cultured in LB medium containing 50 µg/mL of kanamycin. As a result of extracting plasmid from the harvested bacterial cells (transformant), plasmid pET-FcR13 was obtained that contained a polynucleotide encoding a polypeptide having amino acid substitutions at four positions relative to FcR9 (13 positions relative to wild-type Fc-binding protein) in the form of FcR13.

(b-7) The nucleotide sequence of pET-FcR13 was analyzed using the same method as in section (5) of Example 1.

The amino acid sequence of FcR13 containing a signal sequence and polyhistidine tag is shown in SEQ ID NO: 67, and the sequence of the polynucleotide encoding the aforementioned FcR13 is shown in SEQ ID NO: 68. Furthermore, in SEQ ID NO: 67, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR13 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 67, the glycine of Glu21Gly is present at position 37, the methionine of Leu23Met is present at position 39, the glutamic acid of Val27Glu is present at position 43, the isoleucine of Phe29Ile is present at position 45, the asparagine of Tyr35Asn is present at position 51, the arginine of Gln48Arg is present at position 64, the proline of Ser68Pro is present at position 84, the leucine of Phe75Leu is present at position 91, the serine of Asn92Ser is present at position 108, the glutamic acid of Val117Glu is present at position 133, the glycine of Glu121Gly is present at position 137, the serine of Phe171Ser is present at position 187, and the arginine of Ser178Arg is present at position 194.

Example 20 Evaluation of Alkaline Stability of Fc-Binding Proteins (1) Transformants expressing the Fc-binding protein produced in section (c) of Example 4 (FcR5a), the Fc-binding protein produced in section (b) of Example 7 (FcR9), and the Fc-binding proteins produced in Example 19 (FcR12, FcR13) were cultured according to the method described in sections (1) to (4) of Example 8 followed by extraction of the proteins to prepare FcR5a, FcR9, FcR12 and FcR13.

(2) Antibody binding activity of the FcR5A, FcR9, FcR12 and FcR13 present in the protein extracts prepared in (1) was measured using the ELISA method described in section (4) of Example 3. At this time, concentrations were measured by preparing a calibration curve using purified and quantified FcR9.

(3) After diluting each of the Fc-binding proteins to a concentration of 30 µg/mL with pure water, 50 µL of the aforementioned diluted solutions and 50 µL of 40 mM aqueous sodium hydroxide solution were mixed to subject to alkaline treatment by allowing to stand undisturbed for 2 hours at 30° C. Subsequently, the solutions were neutralized by adding four volumes of 1 M Tris-HCl buffer (pH 7.0) followed by measuring antibody binding activity of the Fc-binding proteins according to the ELISA method described in section (4) of Example 3.

(4) Alkaline stability was evaluated by calculating residual activity by dividing antibody binding activity in the case of having undergone alkaline treatment by antibody binding activity in the case of having not undergone alkaline treatment.

The results are shown in Table 13. Since the FcR12 and FcR13 produced in Example 19 demonstrated higher residual activity in comparison with FcR5a and FcR9, the alkaline stability of FcR12 and FcR13 was confirmed to be improved in comparison with FcR5a and RcR9.

TABLE 13

| | Fc-Binding Protein | | Residual |
|---|---|---|---|
| | Name | SEQ ID NO: | Activity (%) |
| Example 19(a) | FcR12 | 63 | 65.5 |
| Example19(b) | FcR13 | 67 | 78.0 |
| Example 7(b) | FcR9 | 47 | 54.9 |
| Example 4(c) | FcR5a | 37 | 51.6 |

Example 21 Introduction of Mutation into FcR13 and Construction of Library

A mutation was randomly introduced into the polynucleotide moiety encoding the FcR13 constructed in section (b) of Example 19 by error-prone PCR.

(1) Error-prone PCR was carried out using the expression vector pET-FcR13 constructed in section (b) of Example 19 as template. With the exception of using pET-Fc13 as template and using oligonucleotides composed of the sequences according to SEQ ID NO: 23 and SEQ ID NO: 24 as primers, error-prone PCR was carried out by preparing a reaction solution having the composition shown in Table 3 followed by subjecting the reaction solution to heat treatment for 2 minutes at 95° C., carrying out the reaction, in which 1 cycle consisted of a first step carried out for 30 seconds at 95° C., a second step carried out for 30 seconds at 50° C. and a third step carried out for 90 seconds at 72° C., for 35 cycles, and finally subjecting the reaction solution to heat treatment for 7 minutes at 72° C. A mutation was favorably introduced into a polynucleotide encoding Fc-binding protein by this reaction.

(2) After purifying the PCR product obtained in (1) and digesting with restriction enzymes NcoI and HindIII, the resulting digested product was ligated to expression vector pETMalE preliminarily digested with restriction enzymes NcoI and HindIII (Japanese Unexamined Patent Publication No. 2011-206046).

(3) Following completion of the ligation reaction, the reaction solution was introduced into Escherichia coli strain BL21(DE3) by electroporation, and after culturing on LB plate medium containing 50 µg/mL of kanamycin, the colonies that formed on the plate were used as a random mutant library.

Example 22 Screening of Alkaline-Stabilized Fc-Binding Protein (1) The random mutant library produced in Example 21 was cultured according to the method described in sections (1) and (2) of Example 3 to express Fc-binding protein.

(2) After culturing, the resulting culture supernatant containing Fc-binding protein obtained by centrifugation was subjected to alkaline treatment according to a method indicated below. Furthermore, following alkaline treatment, the pH was returned to the vicinity of neutrality with four volumes of 1 M Tris buffer (pH 7.0).

(i) The culture supernatant was diluted five-fold with pure water and mixed with an equal volume of 80 mM aqueous sodium hydroxide solution followed by allowing to stand for 2 hours at 30° C.

(ii) The culture supernatant was diluted 20-fold with pure water and mixed with an equal volume of 60 mM aqueous sodium hydroxide solution followed by allowing to stand undisturbed for 2 hours at 30° C.

(3) The antibody binding activity of the Fc-binding protein when subjected to the alkaline treatment described in (2) and the antibody binding activity of the Fc-binding protein when not subjected to the alkaline treatment described in (2) were each measured according to the ELISA procedure described in section (4) of Example 3. Subsequently, residual activity was calculated by dividing the antibody binding activity when the Fc-binding protein was subjected to alkaline treatment by the antibody binding activity when the Fc-binding protein was not subjected to alkaline treatment.

(4) Approximately 2700 strains of transformants were evaluated using the method of (3), and those transformants that expressed Fc-binding protein having improved stability in comparison with FcR13 were selected. The selected transformants were then cultured in 2YT liquid medium containing 50 µg/mL of kanamycin and expression vectors were prepared using the QIAprep Spin Miniprep Kit (Qiagen).

(5) The nucleotide sequences of the polynucleotide region encoding the Fc-binding protein inserted into the resulting expression vectors were analyzed using the same method as that described in section (5) of Example 1 to identify the positions of amino acid mutations.

The positions of amino acid substitutions and residual activity (%) after alkaline treatment of the Fc-binding proteins expressed by the transformants selected in (4) relative to FcR13 are collectively shown in Table 14 (alkaline treatment: conditions of (i)) and Table 15 (alkaline treatment: conditions of (ii)). Those Fc-binding proteins containing the amino acid residues from glycine at position 33 to glutamine at position 208 in the amino acid sequence according to SEQ ID NO: 37, and having at least one of any of the amino acid substitutions of Met18Lys (in this nomenclature, methionine as the 18th amino acid of SEQ ID NO: 1 (34th amino acid of SEQ ID NO; 37) is substituted with lysine, and to apply similarly hereinafter), Met18Thr, Leu (Met)23Arg (in this nomenclature, leucine at position 23 in SEQ ID NO: 1 (39th amino acid in SEQ ID NO: 37) is initially substituted with methionine and then further substituted with arginine, and to apply similarly hereinafter), Lys46Ile, Gln(Arg)48Trp, Tyr51His, Tyr51Asn, Glu54Asp, Glu54Gly, Asn56Ser, Asn56Ile, Phe61Leu, Phe61Tyr, Glu64Gly, Ile67Leu, Ser69Asn, Ala71Thr, Tyr74Phe, Phe(Leu)75Arg, Ala78Glu, Val81Glu, Asp82Glu, Glu86Asp, Gln90Leu, Leu93Gln, Pro114Leu, Lys119Asn, Lys119Tyr, His125Gln, Ser130Thr, Lys138Arg, Gln143His, Gly147Val, Lys149Met, Phe151Tyr, His153Tyr, Tyr158Phe, Lys161Arg, Ser169Gly, Asn180Ser, Thr185Ala, Asn187Ile, Asn187Lys and Thr191Ala in the amino acid residues from position 33 to position 208 can be said to have improved alkaline stability in comparison with FcR13.

TABLE 14

| Amino Acid Substitution | Residual Activity (%) |
|---|---|
| Leu(Met)23Arg | 15.4 |
| Tyr51His | 17.0 |
| Glu54Asp | 14.1 |
| Glu54Gly | 15.0 |
| Phe61Leu | 18.4 |
| Ala78Glu | 14.5 |
| Lys119Asn | 19.0 |
| Thr185Ala | 15.5 |
| Asn56Ser, Glu86Asp | 12.7 |
| Gln90Leu, Thr185Ala | 15.3 |
| His153Tyr, Asn187Ile | 24.2 |
| Met18Lys, Lys46Ile, Asn56Ile | 17.6 |
| Tyr51Asn, Val81Glu, Lys138Arg | 33.1 |
| Asn56Ser, Thr185Ala, Thr191Ala | 17.1 |
| Ala71Thr, Pro114Leu, Phe151Tyr | 16.4 |
| Phe(Leu)75Arg, Gln143His, Asn180Ser | 15.0 |
| Leu93Gln, Lys161Arg, Ser169Gly | 17.0 |
| Phe61Tyr, Ser69Asn, Tyr74Phe, His125Gln, Lys149Met | 19.2 |
| Glu64Gly, Asp82Glu, Lys119Tyr, Ser130Thr, Tyr158Phe, Asn187Lys | 38.0 |
| FcR13 | 12.0 |

TABLE 15

| Amino Acid Substitution | Residual Activity (%) |
|---|---|
| Gly147Val | 53.5 |
| Met18Thr, Gln(Arg)48Trp, Ile67Leu | 13.3 |
| FcR13 | 10.5 |

Among the Fc-binding proteins having amino acid substitutions from FcR13 shown in Table 15, the Fc-binding protein containing the amino acid substitution Gly147Val was designated as FcR14, and the expression vector containing the polynucleotide encoding FcR14 was designated as pET-FcR14. The amino acid sequence of FcR14 is shown in SEQ ID NO: 69, while the sequence of the nucleotide encoding FcR14 is shown in SEQ ID NO: 70. Furthermore, in SEQ ID NO: 69, the sequence from the methionine (Met) at position 1 to alanine (Ala) at position 26 constitutes an MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR14 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 69, the glycine of Glu21Gly is present at position 37, the methionine of Leu23Met is present at position 39, the glutamic acid of Val27Glu is present at position 43, the isoleucine of Phe29Ile is present at position 45, the asparagine of Tyr35Asn is present at position 51, the arginine of Gln48Arg is present at position 64, the proline of Ser68Pro is present at position 84, the leucine of Phe75Leu is present at position 91, the serine of Asn92Ser is present at position 108, the glutamic acid of Val117Glu is present at position 133, the glycine of Glu121Gly is present at position 137, the valine of Gly147Val is present at position 163, the serine of Phe171Ser is present at position 187, and the arginine of Ser178Arg is present at position 194.

Example 23 Construction of Improved Fc Binding Protein

An improved Fc-binding protein was produced by selecting Tyr51His and Glu54Asp from among the amino acid substitutions clearly determined to be involved in improvement of alkaline stability of Fc-binding proteins in Example 22, and integrating these substitutions into FcR14. The following provides a detailed explanation of the production method.

(1) In addition to using the pET-FcR14 obtained in Example 22 as template and using oligonucleotides composed of the sequences according to SEQ ID NO: 24 and SEQ ID NO: 71 (5'-TGCCGGGGCGCGCATAGCCCG-GATGATAAC-3') as PCR primers, PCR was carried out by preparing a reaction solution having the composition shown in Table 5, followed by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 5 minutes at 72° C. The amplified PCR product was subjected to agarose gel electrophoresis and then purified from the gel using the QIAquick Gel Extraction Kit (Qiagen). The purified PCR product was designated as m16F.

(2) PCR was carried out using the same method as (1) with the exception of using the pET-FcR14 obtained in Example 22 as template, and using oligonucleotides composed of the sequences according to SEQ ID NO: 23 and SEQ ID NO: 72 (5'-GGTGCTGTTATCATCCGGGCTAT-GCGCGCC-3') as PCR primers. The purified PCR product was designated as m16R.

(3) The two PCR products (m16F and m16R) obtained in (1) and (2) were mixed and a reaction solution having the composition shown in Table 6 was prepared. PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 5 cycles, and finally subjecting to heat treatment for 5 minutes at 72° C. to obtain PCR product m16p in which m16F and m16R were linked.

(4) PCR was carried out using the PCR product m16p obtained in (3) as template and using oligonucleotides composed of the sequences according to SEQ ID NO: 23 and SEQ ID NO: 24 as PCR primers. After preparing a reaction solution having the composition shown in Table 7, PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 5 minutes at 72° C. As a result, a polynucleotide was constructed that encoded FcR16 having amino acid substitutions introduced at two positions in FcR14.

(5) After purifying the polynucleotide obtained in (4), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(6) The resulting transformant was cultured in LB medium containing 50 µg/mL of kanamycin. As a result of extracting plasmid from the harvested bacterial cells (transformant), plasmid pET-FcR16 was obtained that contained a polynucleotide encoding a polypeptide having amino acid substitutions at two positions relative to FcR14 (16 positions relative to wild-type Fc-binding protein) in the form of FcR16.

(7) The nucleotide sequence of pET-FcR16 was analyzed using the same method as in section (5) of Example 1.

The amino acid sequence of FcR16 containing a signal sequence and polyhistidine tag is shown in SEQ ID NO: 73, and the sequence of the polynucleotide encoding the aforementioned FcR16 is shown in SEQ ID NO: 74. Furthermore, in SEQ ID NO: 73, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR16 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 73, the glycine of Glu21Gly is present at position 37, the methionine of Leu23Met is present at position 39, the glutamic acid of Val27Glu is present at position 43, the isoleucine of Phe29Ile is present at position 45, the asparagine of Tyr35Asn is present at position 51, the arginine of Gln48Arg is present at position 64, the histidine of Tyr51His is present at position 67, the aspartic acid of Glu54Asp is present at position 70, the proline of Ser68Pro is present at position 84, the leucine of Phe75Leu is present at position 91, the serine of Asn92Ser is present at position 108, the glutamic acid of Val117Glu is present at position 133, the glycine of Glu121Gly is present at position 137, the valine of Gly147Val is present at position 163, the serine of Phe171Ser is present at position 187, and the arginine of Ser178Arg is present at position 194.

Example 24 Evaluation of Alkaline Stability of Fc-Binding Proteins (1) Transformants expressing the Fc-binding protein produced in section (b) of Example 19 (FcR13), the Fc-binding protein obtained in Example 22 (FcR14), and the Fc-binding protein produced in Example 23 (FcR16) were cultured according to the method described in sections (1) to (4) of Example 8 followed by extraction of the proteins to prepare FcR13, FcR14 and FcR16.

(2) Antibody binding activity of the FcR13, FcR14 and FcR16 present in the protein extracts prepared in (1) was measured using the ELISA method described in section (4) of Example 3. At this time, concentrations were measured by preparing a calibration curve using purified and quantified FcR9.

(3) After diluting each of the Fc-binding proteins to a concentration of 10 µg/mL with pure water, 50 µL of the aforementioned diluted solutions and 50 µL of 60 mM aqueous sodium hydroxide solution were mixed to subject to alkaline treatment by allowing to stand undisturbed for 2 hours at 30° C. Subsequently, the solutions were neutralized by adding four volumes of 1 M Tris-HCl buffer (pH 7.0) followed by measuring antibody binding activity of the Fc-binding proteins according to the ELISA method described in section (4) of Example 3.

(4) Alkaline stability was evaluated by calculating residual activity by dividing antibody binding activity in the case of having undergone alkaline treatment by antibody binding activity in the case of having not undergone alkaline treatment.

The results are shown in Table 16. Since the FcR14 produced in Example 22 and FcR16 produced in Example 23 demonstrated higher residual activity in comparison with FcR13, the alkaline stability of FcR14 and FcR16 was confirmed to be improved in comparison with FcR13.

TABLE 16

| | Fc-Binding Protein | | Residual |
| --- | --- | --- | --- |
| | Name | SEQ ID NO: | Activity (%) |
| Example 22 | FcR14 | 69 | 49.6 |
| Example 23 | FcF16 | 73 | 62.7 |
| Example 19(b) | FcR13 | 67 | 12.3 |

Example 25 Introduction of Mutation into FcR16 and Construction of Library

A mutation was randomly introduced into the polynucleotide moiety encoding the FcR16 produced in Example 23 by error-prone PCR.

(1) Error-prone PCR was carried out using the expression vector pET-FcR16 constructed Example 23 as template. With the exception of using pET-FcR16 as template and using oligonucleotides composed of the sequences according to SEQ ID NO: 23 and SEQ ID NO: 24 as primers, error-prone PCR was carried out by preparing a reaction solution having the composition shown in Table 3 followed by subjecting the reaction solution to heat treatment for 2 minutes at 95° C., carrying out the reaction, in which 1 cycle consisted of a first step carried out for 30 seconds at 95° C., a second step carried out for 30 seconds at 50° C. and a third step carried out for 90 seconds at 72° C., for 35 cycles, and finally subjecting the reaction solution to heat treatment for 7 minutes at 72° C. A mutation was favorably introduced into a polynucleotide encoding Fc-binding protein by this reaction.

(2) After purifying the PCR product obtained in (1) and digesting with restriction enzymes NcoI and HindIII, the resulting digested product was ligated to expression vector pETMalE preliminarily digested with restriction enzymes NcoI and HindIII (Japanese Unexamined Patent Publication No. 2011-206046).

(3) Following completion of the ligation reaction, the reaction solution was introduced into *Escherichia coli* strain BL21(DE3) by electroporation, and after culturing on LB plate medium containing 50 μg/mL of kanamycin, the colonies that formed on the plate were used as a random mutant library.

Example 26 Screening of Alkaline-Stabilized Fc-Binding Protein (1) The random mutant library produced in Example 25 was cultured according to the method described in sections (1) and (2) of Example 3 to express Fc-binding protein.

(2) After culturing, the resulting culture supernatant containing Fc-binding protein obtained by centrifugation was diluted 20-fold with pure water and subjected to alkaline treatment by mixing with an equal volume of 80 mM aqueous sodium hydroxide solution followed by allowing to stand for 2 hours at 30° C. Following alkaline treatment, the pH was returned to the vicinity of neutrality with four volumes of 1 M Tris buffer (pH 7.0).

(3) The antibody binding activity of the Fc-binding protein when subjected to the alkaline treatment described in (2) and the antibody binding activity of the Fc-binding protein when not subjected to the alkaline treatment described in (2) were each measured according to the ELISA procedure described in section (4) of Example 3. Subsequently, residual activity was calculated by dividing the antibody binding activity when the Fc-binding protein was subjected to alkaline treatment by the antibody binding activity when the Fc-binding protein was not subjected to alkaline treatment.

(4) Approximately 2700 strains of transformants were evaluated using the method of (3), and those transformants that expressed Fc-binding protein having improved stability in comparison with FcR16 were selected. The selected transformants were then cultured in 2YT liquid medium containing 50 μg/mL of kanamycin and expression vectors were prepared using the QIAprep Spin Miniprep Kit (Qiagen).

(5) The nucleotide sequences of the polynucleotide region encoding the Fc-binding protein inserted into the resulting expression vectors were analyzed using the same method as that described in section (5) of Example 1 to identify the positions of amino acid mutations.

The positions of amino acid substitutions and residual activity (%) after alkaline treatment of the Fc-binding proteins expressed by the transformants selected in (4) relative to FcR16 are collectively shown in Table 17. Those Fc-binding proteins containing the amino acid residues from glycine at position 33 to glutamine at position 208 in the amino acid sequence according to SEQ ID NO: 37 (corresponding to position 17 to position 192 in SEQ ID NO: 1), and having at least one of any of the amino acid substitutions of Ala78Ser (in this nomenclature, alanine at position 78 in SEQ ID NO: 1 (position 94 in SEQ ID NO: 37) is substituted with serine, and to apply similarly hereinafter), Asp82Glu, Gln101Leu, Gln101Arg, Thr140Ile, Gln143His, Tyr158His, Lys161Arg, Lys165Glu, Thr185Ala, Asn187Asp and Asn187Tyr in the amino acid residues from position 33 to position 208 can be said to have improved alkaline stability in comparison with FcR16.

TABLE 17

| Amino Acid Substitution | Residual Activity (%) |
|---|---|
| Ala78Ser, Thr185Ala | 63.8 |
| Asp82Glu, Gln101Leu, Asn187Asp | 51.5 |
| Gln101Arg, Lys161Arg | 45.3 |
| Thr140Ile | 76.5 |
| Gln143His | 60.9 |
| Thr140Ile, Tyr158His | 104.1 |
| Lys165Glu | 43.5 |
| Asn187Tyr | 62.6 |
| FcR16 | 36.0 |

Example 27 Construction of Improved Fc Binding Proteins

Stability was attempted to be further improved by integrating those amino acid substitutions determined in Example 26 to be involved in improvement of alkaline stability of Fc-binding protein into FcR16. Integration of amino acid substitutions was mainly carried out using PCR and the three types of Fc-binding proteins indicated in (a) and (b) below were produced.

(a) FCR19 obtained by additional amino acid substitution of Thr140Ile, Tyr158His and Lys165Glu in FcR16

(b) FcR21 obtained by additional amino acid substitution of Asp82Glu, Gln101Leu, Thr140Ile, Tyr158His and Lys165Glu in FcR16

(c) FcR24 obtained by additional amino acid substitution of Ala78Ser, Asp82Glu, Gln101Leu, Thr140Ile, Tyr158His, Lys165Glu, Thr185Ala and Asn187Asp in FcR16

The following provides a detailed explanation of the methods used to produce each of the improved Fc-binding proteins.

(a) FcR19

Thr140Ile, Tyr158His and Lys165Glu were selected from among the amino acid substitutions clearly determined to be involved in improvement of alkaline stability in Example 26, and FcR19 was produced in which these substitutions were integrated into FcR16 (Example 23). More specifically, FcR19 was produced by introducing a mutation that results in the occurrence of Lys165Glu into the polynucleotide containing mutations Thr140Ile and Tyr158His obtained in Example 26.

(a-1) In addition to using the polynucleotide encoding Fc-binding protein containing the mutations Thr140Ile and Tyr158His in FcR16 obtained in Example 26 as template and using oligonucleotides composed of the sequences according to SEQ ID NO: 24 and SEQ ID NO: 75 (5'-ATTC-CCAAAGCGACGCTGGAGGACAGCGGC-3') as PCR primers, after preparing a reaction solution having the composition shown in Table 5, PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 5 minutes at 72° C. The amplified PCR product was subjected to agarose gel electrophoresis and then purified from the gel using the QIAquick Gel Extraction Kit (Qiagen). The purified PCR product was designated as m19F.

(a-2) PCR was carried out using the same method as (a-1) with the exception of using the polynucleotide encoding Fc-binding protein containing the mutations Thr140Ile and Tyr158His in FcR16 acquired in Example 26 and using oligonucleotides composed of the sequences according to SEQ ID NO: 23 and SEQ ID NO: 76 (5'-ATAGCTGCCGCTGTCCTCCAGCGTCGCTTT-3') as PCR primers. The purified PCR product was designated as m19R.

(a-3) The two PCR products (m19F and m19R) obtained in (a-1) and (a-2) were mixed and a reaction solution having the composition shown in Table 6 was prepared. PCR was carried out by subjecting the reaction solution to heat treatment for 5 minutes at 98° C., followed by carrying out a reaction, in which 1 cycle consisted of a first step carried out for 10 seconds at 98° C., a second step carried out for 5 seconds at 55° C. and a third step carried out for 1 minute at 72° C., for 5 cycles to obtain PCR product m19p in which m19F and m19R were linked.

(a-4) PCR was carried out using the PCR product m19p obtained in (a-3) as template and using oligonucleotides composed of the sequences according to SEQ ID NO: 23 and SEQ ID NO: 24 as PCR primers. After preparing a reaction solution having the composition shown in Table 7, PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 30 cycles. As a result, a polynucleotide was constructed that encoded FcR19 having amino acid substitutions introduced at three positions in FcR16.

(a-5) After purifying the polynucleotide obtained in (a-4), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform Escherichia coli strain BL21(DE3).

(a-6) The resulting transformant was cultured in LB medium containing 50 μg/mL of kanamycin. As a result of extracting plasmid from the harvested bacterial cells (transformant), plasmid pET-FcR19 was obtained that contained a polynucleotide encoding a polypeptide having amino acid substitutions at three positions relative to FcR16 (19 positions relative to wild-type Fc-binding protein) in the form of FcR19.

(a-7) The nucleotide sequence of pET-FcR19 was analyzed using the same method as in section (5) of Example 1.

The amino acid sequence of FcR19 containing a signal sequence and polyhistidine tag is shown in SEQ ID NO: 77, and the sequence of the polynucleotide encoding the aforementioned FcR19 is shown in SEQ ID NO: 78. Furthermore, in SEQ ID NO: 77, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR19 (corresponding to the region from position 17 to position 192 of SEQ ID NO: 1), the sequence from position glycine (Gly) at 209 to glycine (Gly) at position 210 constitutes a linker sequence, and the sequence from histidine (His) at position 211 to histidine (His) at position 216 constitutes a tag sequence. In addition, in SEQ ID NO: 73, the glycine of Glu21Gly is present at position 37, the methionine of Leu23Met is present at position 39, the glutamic acid of Val27Glu is present at position 43, the isoleucine of Phe29Ile is present at position 45, the asparagine of Tyr35Asn is present at position 51, the arginine of Gln48Arg is present at position 64, the histidine of Tyr51His is present at position 67, the aspartic acid of Glu54Asp is present at position 70, the proline of Ser68Pro is present at position 84, the leucine of Phe75Leu is present at position 91, the serine of Asn92Ser is present at position 108, the glutamic acid of Val117Glu is present at position 133, the glycine of Glu121Gly is present at position 137, the isoleucine of Thr140Ile is present at position 156, the valine of Gly147Val is present at position 163, the histidine of Tyr158His is present at position 174, the glutamic acid of Lys165Glu is present at position 181, the serine of Phe171Ser is present at position 187, and the arginine of Ser178Arg is present at position 194.

(b) FcR21

Mutations resulting in the occurrence of Thr140Ile, Tyr158His and Lys165Glu were introduced into the polynucleotide containing mutations Asp82Glu, Gln101Leu and Asn187Asp obtained in Example 26 to obtain an improved Fc-binding protein. Furthermore, since Asn187Asp among the aforementioned mutations was deleted during the procedure of (b-9) to be subsequently described, the improved Fc-binding protein actually obtained in this experiment was an Fc-binding protein that integrated the substitutions of Asp82Glu, Gln101Leu, Thr140Ile, Tyr158His and Lys165Glu into FcR16 (Example 23).

(b-1) In addition to using the polynucleotide encoding Fc-binding protein containing the mutations Asp82Glu, Gln101Leu and Asn187Asp in FcR16 obtained in Example 26 as template and using oligonucleotides composed of the sequences according to SEQ ID NO: 24 and SEQ ID NO: 79 (5'-ACCGCCCTGCATAAAGTGATCTACCTGCAA-3') as PCR primers, after preparing a reaction solution having the composition shown in Table 5, PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 5 minutes at 72° C. The amplified PCR product was subjected to agarose gel electrophoresis and then purified from the gel using the QIAquick Gel Extraction Kit (Qiagen). The purified PCR product was designated as m21-2F.

(b-2) PCR was carried out using the same method as (b-1) with the exception of using the polynucleotide encoding Fc-binding protein containing the mutations Asp82Glu, Gln101Leu and Asn187Asp in FcR16 obtained in Example 26 and using oligonucleotides composed of the sequences according to SEQ ID NO: 23 and SEQ ID NO: 80 (5'-TTGCAGGTAGATCACTTTATGCAGGGCGGT-3') as PCR primers. The purified PCR product was designated as m21-2R.

(b-3) The two PCR products (m21-2F and m21-2R) obtained in (b-1) and (b-2) were mixed and a reaction solution having the composition shown in Table 6 was prepared. PCR was carried out by subjecting the reaction solution to heat treatment for 5 minutes at 98° C., followed by carrying out a reaction, in which 1 cycle consisted of a first step carried out for 10 seconds at 98° C., a second step carried out for 5 seconds at 55° C. and a third step carried out for 1 minute at 72° C., for 5 cycles to obtain PCR product m21-2p in which m21-2F and m21-2R were linked.

(b-4) PCR was carried out using the PCR product m21-2p obtained in (b-3) as template and using oligonucleotides composed of the sequences according to SEQ ID NO: 23 and SEQ ID NO: 24 as PCR primers. After preparing a reaction solution having the composition shown in Table 7, PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 30 cycles. As a result, a polynucleotide was constructed that encoded FcR21-2 containing mutations Asp82Glu, Gln101Leu, Thr140Ile and Asn187Asp in FcR16.

(b-5) In addition to using the polynucleotide encoding FcR21-2 containing mutations Asp82Glu, Gln101Leu, Thr140Ile and Asn187Asp in FcR16 obtained in (b-4) as template and using oligonucleotides composed of the sequences according to SEQ ID NO: 24 and SEQ ID NO: 81 (5'-CACCACAACTCCGACTTCCATATTCCCAAA-3') as PCR primers, after preparing a reaction solution having the composition shown in Table 5, PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 5 minutes at 72° C. The amplified PCR product was subjected to agarose gel electrophoresis and then purified from the gel using the QIAquick Gel Extraction Kit (Qiagen). The purified PCR product was designated as m21-1F.

(b-6) PCR was carried out using the same method as (b-5) with the exception of using the polynucleotide encoding FcR21-2 containing the mutations Asp82Glu, Gln101Leu, Thr140Ile and Asn187Asp in FcR16 obtained in (b-4) and using oligonucleotides composed of the sequences according to SEQ ID NO: 23 and SEQ ID NO: 82 (5'-CAGCGTCGCTTTGGGAATATGGAAGTCGGA-3') as PCR primers. The purified PCR product was designated as m21-1R.

(b-7) The two PCR products (m21-1F and m21-1R) obtained in (b-5) and (b-6) were mixed and a reaction solution having the composition shown in Table 6 was prepared. PCR was carried out by subjecting the reaction solution to heat treatment for 5 minutes at 98° C., followed by carrying out a reaction, in which 1 cycle consisted of a first step carried out for 10 seconds at 98° C., a second step carried out for 5 seconds at 55° C. and a third step carried out for 1 minute at 72° C., for 5 cycles to obtain PCR product m21-1p in which m21-1F and m21-1R were linked.

(b-8) PCR was carried out using the PCR product m21-1p obtained in (b-7) as template and using oligonucleotides composed of the sequences according to SEQ ID NO: 23 and SEQ ID NO: 24 as PCR primers. After preparing a reaction solution having the composition shown in Table 7, PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 30 cycles. As a result, a polynucleotide was constructed that encoded FcR21-1 containing mutations Asp82Glu, Gln101Leu, Thr140Ile, Tyr158His and Asn187Asp in FcR16.

(b-9) In addition to using the polynucleotide encoding FcR21-1 containing mutations Asp82Glu, Gln101Leu, Thr140Ile, Tyr158His and Asn187Asp in FcR16 obtained in (b-8) as template and using oligonucleotides composed of the sequences according to SEQ ID NO: 22 and SEQ ID NO: 75 as PCR primers, after preparing a reaction solution having the composition shown in Table 5, PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 5 minutes at 72° C. The amplified PCR product was subjected to agarose gel electrophoresis and then purified from the gel using the QIAquick Gel Extraction Kit (Qiagen). The purified PCR product was designated as m21F (the mutation Asn187Asp was deleted as a result of this procedure).

(b-10) PCR was carried out using the same method as (b-9) with the exception of using the polynucleotide encoding FcR21-1 containing the mutations Asp82Glu, Gln101Leu, Thr140Ile, Tyr158His and Asn187Asp in FcR16 acquired in (b-8) and using oligonucleotides composed of the sequences according to SEQ ID NO: 62 and SEQ ID NO: 76 as PCR primers. The purified PCR product was designated as m21R.

(b-11) The two PCR products (m21F and m21R) obtained in (b-9) and (b-10) were mixed and a reaction solution having the composition shown in Table 6 was prepared. PCR was carried out by subjecting the reaction solution to heat treatment for 5 minutes at 98° C., followed by carrying out a reaction, in which 1 cycle consisted of a first step carried out for 10 seconds at 98° C., a second step carried out for 5 seconds at 55° C. and a third step carried out for 1 minute at 72° C., for 5 cycles to obtain PCR product m21p in which m21F and m21R were linked.

(b-12) PCR was carried out using the PCR product m21p obtained in (b-11) as template and using oligonucleotides composed of the sequences according to SEQ ID NO: 62 and SEQ ID NO: 22 as PCR primers. After preparing a reaction solution having the composition shown in Table 7, PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 30 cycles. As a result, a polynucleotide was constructed that encoded FcR21, in which amino acid substitutions were introduced in FcR16 at five positions (Asp82Glu, Gln101Leu, Thr140Ile, Tyr158His and Lys165Glu) (21 positions relative wild-type Fc-binding protein).

(b-13) After purifying the polynucleotide obtained in (b-12), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(b-14) The resulting transformant was cultured in LB medium containing 50 μg/mL of kanamycin. As a result of extracting plasmid from the harvested bacterial cells (transformant), plasmid pET-FcR21 was obtained that contained a polynucleotide encoding a polypeptide having amino acid substitutions at five positions relative to FcR16 in the form of FcR21.

(b-15) The nucleotide sequence of pET-FcR21 was analyzed using the same method as in section (5) of Example 1.

The amino acid sequence of FcR21 containing a signal sequence and polyhistidine tag is shown in SEQ ID NO: 83, and the sequence of the polynucleotide encoding the aforementioned FcR21 is shown in SEQ ID NO: 84. Furthermore, in SEQ ID NO: 83, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR21 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 83, the glycine of Glu21Gly is present at position 37, the methionine of Leu23Met is present at position 39, the glutamic acid of Val27Glu is present at position 43, the isoleucine of Phe29Ile is present at position 45, the asparagine of Tyr35Asn is present at position 51, the arginine of Gln48Arg is present at position 64, the histidine of Tyr51His is present at position 67, the aspartic acid of Glu54Asp is present at position 70, the proline of Ser68Pro is present at position 84, the leucine of Phe75Leu is present at position 91, the glutamic acid of Asp82Glu is present at position 98, the serine of Asn92Ser is present at position 108, the leucine of Gln101Leu is present at position 117, the glutamic acid of Val117Glu is present at position 133, the glycine of Glu121Gly is present at position 137, the isoleucine of Thr140Ile is present at position 156, the valine of Gly147Val is present at position 163, the histidine of Tyr158His is present at position 174, the glutamic acid of Lys165Glu is present at position 181, the serine of Phe171Ser is present at position 187, and the arginine of Ser178Arg is present at position 194.

(c) FcR24

Ala78Ser, Asp82Glu, Gln101Leu, Thr140Ile, Tyr158His, Lys165Glu, Thr185Ala and Asn187Asp were selected from among the amino acid substitutions clearly determined to be involved in improvement of alkaline stability in Example 26, and FcR24 was produced in which these substitutions were integrated into FcR16 (Example 23). More specifically, FcR24 was produced by introducing mutations that result in the occurrence of Ala78Ser, Thr185Ala and Asn187Asp into the polynucleotide encoding FcR21.

(c-1) In addition to using pET-FcR21 conducted in (b) as template and using oligonucleotides composed of the sequences according to SEQ ID NO: 24 and SEQ ID NO: 85 (5'-AGCAGCTACCTTATTGATTCGGCGACGGTG-3') as PCR primers, after preparing a reaction solution having the composition shown in Table 5, PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 5 minutes at 72° C. The amplified PCR product was subjected to agarose gel electrophoresis and then purified from the gel using the QIAquick Gel Extraction Kit (Qiagen). The purified PCR product was designated as m24-2F.

(c-2) PCR was carried out using the same method as (c-1) with the exception of using the pET-FcR21 constructed in (b) as template and using oligonucleotides composed of the sequences according to SEQ ID NO: 23 and SEQ ID NO: 86 (5'-GCTATCTTCCACCGTCGCCGAATCAATAAG-3') as PCR primers. The purified PCR product was designated as m24-2R.

(c-3) The two PCR products (m24-2F and m24-2R) obtained in (c-1) and (c-2) were mixed and a reaction solution having the composition shown in Table 6 was prepared. PCR was carried out by subjecting the reaction solution to heat treatment for 5 minutes at 98° C., followed by carrying out a reaction, in which 1 cycle consisted of a first step carried out for 10 seconds at 98° C., a second step carried out for 5 seconds at 55° C. and a third step carried out for 1 minute at 72° C., for 5 cycles to obtain PCR product m24-2p in which m24-2F and m24-2R were linked.

(c-4) PCR was carried out using the PCR product m24-2p obtained in (c-3) as template and using oligonucleotides composed of the sequences according to SEQ ID NO: 23 and SEQ ID NO: 24 as PCR primers. After preparing a reaction solution having the composition shown in Table 7, PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 30 cycles. As a result, a polynucleotide was constructed that encoded FcR24-2 containing mutations Ala78Ser, Asp82Glu, Gln101Leu, Thr140Ile, Tyr158His and Lys165Glu in FcR16.

(c-5) In addition to using the polynucleotide encoding FcR24-2 containing mutations Ala78Ser, Asp82Glu, Gln101Leu, Thr140Ile, Tyr158His and Lys165Glu in FcR16 obtained in (c-4) as template and using oligonucleotides composed of the sequences according to SEQ ID NO: 24 and SEQ ID NO: 87 (5'-AAAAATGTGAGCAGCGAGGC-CGTGGATATT-3') as PCR primers, after preparing a reaction solution having the composition shown in Table 5, PCR was carried out by subjecting the reaction solution to heat treatment for 5 minutes at 98° C., carrying out a reaction, in which 1 cycle consisted of a first step carried out for 10 seconds at 98° C., a second step carried out for 5 seconds at 55° C. and a third step carried out for 1 minute at 72° C., for 30 cycles, and finally subjecting to heat treatment for 5 minutes at 72° C. The amplified PCR product was subjected to agarose gel electrophoresis and then purified from the gel using the QIAquick Gel Extraction Kit (Qiagen). The purified PCR product was designated as m24F.

(c-6) PCR was carried out using the same method as (c-5) with the exception of using the polynucleotide encoding FcR24-2 containing the mutations Ala78Ser, Asp82Glu, Gln101Leu, Thr140Ile, Tyr158His and Lys165Glu in FcR16 acquired in (c-4) and using oligonucleotides composed of the sequences according to SEQ ID NO: 62 and SEQ ID NO: 88 (5'-GGTAATGGTAATATCCACGGCCTCGCTGCT-3') as PCR primers. The purified PCR product was designated as m24R.

(c-7) The two PCR products (m24F and m24R) obtained in (c-5) and (c-6) were mixed and a reaction solution having the composition shown in Table 6 was prepared. PCR was carried out by subjecting the reaction solution to heat treatment for 5 minutes at 98° C., followed by carrying out a reaction, in which 1 cycle consisted of a first step carried out for 10 seconds at 98° C., a second step carried out for 5 seconds at 55° C. and a third step carried out for 1 minute at 72° C., for 5 cycles to obtain PCR product m24p in which m24F and m24R were linked.

(c-8) PCR was carried out using the PCR product m24p obtained in (c-7) as template and using oligonucleotides composed of the sequences according to SEQ ID NO: 62 and SEQ ID NO: 24 as PCR primers. After preparing a reaction solution having the composition shown in Table 7, PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 30 cycles. As a result, a polynucleotide was constructed that encoded FcR24 in which amino acid substitutions were introduced at 8 positions relative to FcR16 (24 positions relative to wild-type Fc-binding protein).

(c-9) After purifying the polynucleotide obtained in (c-8), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(c-10) The resulting transformant was cultured in LB medium containing 50 μg/mL of kanamycin. As a result of extracting plasmid from the harvested bacterial cells (transformant), plasmid pET-FcR24 was obtained that contained a polynucleotide encoding a polypeptide having amino acid substitutions at eight positions relative to FcR16 in the form of FcR24.

(c-11) The nucleotide sequence of pET-FcR24 was analyzed using the same method as in section (5) of Example 1.

The amino acid sequence of FcR24 containing a signal sequence and polyhistidine tag is shown in SEQ ID NO: 89, and the sequence of the polynucleotide encoding the aforementioned FcR24 is shown in SEQ ID NO: 90. Furthermore, in SEQ ID NO: 89, the sequence from the methionine (Met) at position 1 to alanine (Ala) at position 26 constitutes the MalE signal peptide, the sequence from lysine (Lys) at position 27 to methionine (Met) at position 32 constitutes a linker sequence, the sequence from glycine (Gly) at position 33 to glutamine (Gln) at position 208 constitutes the amino acid sequence of FcR24 (corresponding to the region from position 17 to position 192 of SEQ ID NO: 1), the sequence from glycine (Gly) at position 209 to glycine (Gly) at position 210 constitutes a linker sequence, and the sequence from histidine (His) at position 211 to histidine (His) at position 216 constitutes a tag sequence. In addition, in SEQ ID NO: 89, the glycine of Glu21Gly is present at position 37, the methionine of Leu23Met is present at position 39, the glutamic acid of Val27Glu is present at position 43, the isoleucine of Phe29Ile is present at position 45, the asparagine of Tyr35Asn is present at position 51, the arginine of Gln48Arg is present at position 64, the histidine of Tyr51His is present at position 67, the aspartic acid of Glu54Asp is present at position 70, the proline of Ser68Pro is present at position 84, the leucine of Phe75Leu is present at position 91, the serine of Ala78ser is present at position 94, the glutamic acid of Asp82Glu is present at position 98, the serine of Asn92Ser is present at position 108, the leucine of Gln101Leu is present at position 117, the glutamic acid of Val117Glu is present at position 133, the glycine of Glu121Gly is present at position 137, the isoleucine of Thr140Ile is present at position 156, the valine of Gly147Val is present at position 163, the histidine of Tyr158His is present at position 174, the glutamic acid of Lys165Glu is present at position 181, the serine of Phe171Ser is present at position 187, the arginine of Ser178Arg is present at position 194, the alanine of Thr185Ala is present at position 201, and the aspartic acid of Asn187Asp is present at position 203.

Example 28 Evaluation of Alkaline Stability of Fc-Binding Proteins (1) Transformants expressing the Fc-binding protein produced in Example 23 (FcR16) and the Fc-binding proteins acquired in Example 27 (FcR19, FcR21 and FcR24) were cultured according to the method described in sections (1) to (4) of Example 8 followed by extraction of the proteins to prepare FcR16, FcR19, FcR21 and FcR24.

(2) Antibody binding activity of the FcR16, FcR19, FcR21 and FcR24 present in the protein extracts prepared in (1) was measured using the ELISA method described in section (4) of Example 3. At this time, concentrations were measured by preparing a calibration curve using purified and quantified FcR13.

(3) After diluting each of the Fc-binding proteins to a concentration of 10 μg/mL with pure water, 50 μL of the aforementioned diluted solutions and 50 μL of 80 mM aqueous sodium hydroxide solution were mixed to subject to alkaline treatment by allowing to stand undisturbed for 2 hours at 30° C. Subsequently, the solutions were neutralized by adding four volumes of 1 M Tris-HCl buffer (pH 7.0) followed by measuring antibody binding activity of the Fc-binding proteins according to the ELISA method described in section (4) of Example 3.

(4) Alkaline stability was evaluated by calculating residual activity by dividing antibody binding activity in the case of having undergone alkaline treatment by antibody binding activity in the case of having not undergone alkaline treatment.

The results are shown in Table 18. Since the FcR19, FcR21 and FcR24 produced in Example 27 demonstrated higher residual activity in comparison with FcR16, the alkaline stability thereof was confirmed to be improved in comparison with FcR16.

TABLE 18

| | Fc-Binding Protein | | Residual |
| --- | --- | --- | --- |
| | Name | SEQ ID NO: | Activity (%) |
| Example 27(a) | FcR19 | 77 | 78.7 |
| Example 27(b) | FcR21 | 83 | 77.3 |
| Example 27(c) | FcR24 | 89 | 89.8 |
| Example 23 | FcR16 | 73 | 15.3 |

Example 29 Introduction of Mutation into FcR24 and Construction of Library

A mutation was randomly introduced into the polynucleotide moiety encoding the FcR24 constructed in section (c) of Example 27 by error-prone PCR.

(1) Error-prone PCR was carried out using the expression vector pET-FcR24 constructed section (c) of Example 27 as template. With the exception of using pET-FcR24 as template and using oligonucleotides composed of the sequences according to SEQ ID NO: 23 and SEQ ID NO: 24 as primers, error-prone PCR was carried out by preparing a reaction solution having the composition shown in Table 3 followed by subjecting the reaction solution to heat treatment for 2 minutes at 95° C., carrying out a reaction, in which 1 cycle consisted of a first step carried out for 30 seconds at 95° C., a second step carried out for 30 seconds at 50° C. and a third step carried out for 90 seconds at 72° C., for 35 cycles, and finally subjecting the reaction solution to heat treatment for 7 minutes at 72° C. A mutation was favorably introduced into a polynucleotide encoding Fc-binding protein by this reaction.

(2) After purifying the PCR product obtained in (1) and digesting with restriction enzymes NcoI and HindIII, the resulting digested product was ligated to expression vector pETMalE preliminarily digested with restriction enzymes NcoI and HindIII (Japanese Unexamined Patent Publication No. 2011-206046).

(3) Following completion of the ligation reaction, the reaction solution was introduced into *Escherichia coli* strain BL21(DE3) by electroporation, and after culturing on LB plate medium containing 50 μg/mL of kanamycin, the colonies that formed on the plate were used to prepare a random mutant library.

Example 30 Screening of Alkaline-Stabilized Fc-Binding Protein (1) The random mutant library produced in Example 29 was cultured according to the method described in sections (1) and (2) of Example 3 to express Fc-binding protein.

(2) After culturing, the resulting culture supernatant containing Fc-binding protein obtained by centrifugation was diluted 20-fold with pure water and subjected to alkaline treatment by mixing with an equal volume of 80 mM aqueous sodium hydroxide solution followed by allowing to stand for 2 hours at 30° C. Following alkaline treatment, the pH was returned to the vicinity of neutrality with four volumes of 1 M Tris buffer (pH 7.0).

(3) The antibody binding activity of the Fc-binding protein when subjected to the alkaline treatment described in (2) and the antibody binding activity of the Fc-binding protein when not subjected to the alkaline treatment described in (2) were each measured according to the ELISA procedure described in section (4) of Example 3. Subsequently, residual activity was calculated by dividing the antibody binding activity when the Fc-binding protein was subjected to alkaline treatment by the antibody binding activity when the Fc-binding protein was not subjected to alkaline treatment.

(4) Approximately 2700 strains of transformants were evaluated using the method of (3), and those transformants that expressed Fc-binding protein having improved stability in comparison with FcR24 were selected. The selected transformants were then cultured in 2YT liquid medium containing 50 μg/mL of kanamycin and expression vectors were prepared using the QIAprep Spin Miniprep Kit (Qiagen).

(5) The nucleotide sequences of the polynucleotide region encoding the Fc-binding protein inserted into the resulting expression vectors were analyzed using the same method as that described in section (5) of Example 1 to identify the positions of amino acid mutations.

The positions of amino acid substitutions and residual activity (%) after alkaline treatment of the Fc-binding proteins expressed by the transformants selected in (4) relative to FcR24 are collectively shown in Table 19. Those Fc-binding proteins containing the amino acid residues from glycine at position 33 to glutamine at position 208 in the amino acid sequence according to SEQ ID NO: 89 (corresponding to position 17 to position 192 in SEQ ID NO: 1), and having at least one of any of the amino acid substitutions of Lys40Gln (in this nomenclature, lysine at position 40 of SEQ ID NO: 1 (position 56 of SEQ ID NO; 37) is substituted with glutamine, and to apply similarly hereinafter), Lys46Asn, Ala50Thr, Asn56Tyr, His62Leu, Ser65Gly, Tyr74His, Asp77Val, Gln90Leu, Lys119Thr, Lys119Glu, Asp122Glu, His137Gln, Thr(Ile)140Met (in this nomenclature, threonine at position 140 in SEQ ID NO: 1 (position 156 in SEQ ID NO: 37) is initially substituted with isoleucine and then further substituted with methionine, and to apply similarly hereinafter), Tyr141Phe, Tyr(His)158Leu, Leu175Arg, Asn180Lys, Asn180Ser, Ile190Val and Thr191Ile in the amino acid residues from position 33 to position 208 can be said to have improved alkaline stability in comparison with FcR24.

TABLE 19

| Amino Acid Substitution | Residual Activity (%) |
| --- | --- |
| Lys40Gln, Ile190Val | 61.4 |
| Lys46Asn, Lys119Thr, Tyr(His)158Leu, Asn180Lys | 55.8 |
| Ala50Thr | 25.7 |
| Asn56Tyr, Ser65Gly, Gln90Leu, Tyr141Phe | 55.7 |
| His62Leu, Tyr74His, Asp122Glu | 42.0 |
| Asp77Val, His137Gln, Asn180Lys | 62.4 |
| Lys119Glu, Tyr141Phe | 72.0 |
| Lys119Glu, Leu175Arg | 38.7 |
| Asp122Glu | 25.8 |
| Thr(Ile)140Met | 33.8 |
| Asn180Ser | 32.0 |
| Ile190Val | 52.7 |
| Thr191Ile | 40.6 |
| FcR24 | 23.3 |

Example 31 Construction of Amino Acid Substituents of Thr140 or Tyr158

Alkaline resistance in particular was able to be improved by substituting threonine (Thr140) at position 140 of the amino acid of SEQ ID NO: 1 (position 156 in SEQ ID NO: 37) with isoleucine (Ile) and substituting tyrosine (Tyr158) at position 158 of the amino acid SEQ ID NO:1 (position 174 in SEQ ID NO: 37) with histidine among the amino acid substitutions that were clearly determined in Example 26 to be involved in improving alkaline resistance of Fc-binding protein. Therefore, in order to confirm the usefulness of substituting other amino acids for Thr140 and Tyr158, Fc-binding proteins were produced in which Thr140 (position 156 of SEQ ID NO. 89) or Tyr158 (position 174 in SEQ ID NO: 89) in the FcR24 produced in section (c) of Example 27 was substituted with other amino acids.

(a) Construction of Amino Acid Substituents of Thr140

(a-1) In addition to using pET-FcR24 constructed in section (c) of Example 27 as template and using oligonucleotides composed of the sequences according to SEQ ID NO: 24 and SEQ ID NO: 91 (5'-CCTGCATAAAGTGNNKTAC-CTGCAAAACGG-3') as primers, after preparing a reaction solution having the composition shown in Table 3, PCR was carried out by subjecting the reaction solution to heat treatment for 2 minutes at 95° C., carrying out a reaction, in which 1 cycle consisted of a first step carried out for 30 seconds at 95° C., a second step carried out for 30 seconds at 50° C. and a third step carried out for 90 seconds at 72° C., for 35 cycles, and finally subjecting to heat treatment for 7 minutes at 72° C. The resulting PCR product was designated as T140p1.

(a-2) In addition to using pET-FcR24 constructed in section (c) of Example 27 as template and using oligonucleotides composed of the sequences according to SEQ ID NO: 23 and SEQ ID NO: 92 (5'-CCGTTTTGCAGG-TAMNNCACTTTATGCAGG-3') as primers, after preparing a reaction solution having the composition shown in Table 3, PCR was carried out by subjecting the reaction solution to heat treatment for 2 minutes at 95° C., carrying out a reaction, in which 1 cycle consisted of a first step carried out for 30 seconds at 95° C., a second step carried out for 30 seconds at 50° C. and a third step carried out for 90 seconds at 72° C., for 35 cycles, and finally subjecting to heat treatment for 7 minutes at 72° C. The resulting PCR product was designated as T140p2.

(a-3) The two PCR products (T140p1 and T140p2) obtained in (a-1) and (a-2) were mixed and a reaction solution having the composition shown in Table 6 was prepared. PCR was carried out by subjecting the reaction solution to heat treatment for 5 minutes at 98° C., followed by carrying out a reaction, in which 1 cycle consisted of a first step carried out for 10 seconds at 98° C., a second step carried out for 5 seconds at 55° C. and a third step carried out for 1 minute at 72° C., for 5 cycles to obtain PCR product T140p in which T140p1 and T140p2 were linked.

(a-4) PCR was carried out using the PCR product T140p obtained in (a-3) as template and using oligonucleotides composed of the sequences according to SEQ ID NO: 23 and SEQ ID NO: 24 as PCR primers. After preparing a reaction solution having the composition shown in Table 7, PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 30 cycles. As a result, a polynucleotide was obtained that encoded Fc-binding protein in which 140th amino acid of an Fc-binding protein (FcR24) was substituted with a random amino acid. The resulting polynucleotide was designated as T140p3.

(a-5) After purifying the polynucleotide obtained in (a-4), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(a-6) The resulting transformant was cultured in LB medium containing 50 μg/mL of kanamycin.

When plasmid was extracted from the harvested bacterial cells (transformant) and the nucleotide sequence of the polynucleotide region was analyzed according to the method described in section (5) of Example 1, transformants were obtained in which Thr140 of Fc-binding protein FcR24 (isoleucine at position 156 in SEQ ID NO: 89) was substituted with Ala, Arg, Gly, Leu, Lys, Phe, Thr, Ser or Val.

(b) Construction of Amino Acid Substituents of Tyr158

(b-1) In addition to using pET-FcR24 constructed in section (c) of Example 27 as template and using oligonucleotides composed of the sequences according to SEQ ID NO: 24 and SEQ ID NO: 93 (5'-CAACTCCGACTTCNNKAT-TCCCAAAGCGAC-3') as primers, after preparing a reaction solution having the composition shown in Table 3, PCR was carried out by subjecting the reaction solution to heat treatment for 2 minutes at 95° C., carrying out a reaction, in which 1 cycle consisted of a first step carried out for 30 seconds at 95° C., a second step carried out for 30 seconds at 50° C. and a third step carried out for 90 seconds at 72° C., for 35 cycles, and finally subjecting to heat treatment for 7 minutes at 72° C. The resulting PCR product was designated as Y158p1.

(b-2) In addition to using pET-FcR24 constructed in section (c) of Example 27 as template and using oligonucleotides composed of the sequences according to SEQ ID NO: 23 and SEQ ID NO: 94 (5'-GTCGCTTTGGGAAT-MNNGAAGTCGGAGTTG-3') as primers, after preparing a reaction solution having the composition shown in Table 3, PCR was carried out by subjecting the reaction solution to heat treatment for 2 minutes at 95° C., carrying out a reaction, in which 1 cycle consisted of a first step carried out for 30 seconds at 95° C., a second step carried out for 30 seconds at 50° C. and a third step carried out for 90 seconds at 72° C., for 35 cycles, and finally subjecting to heat treatment for 7 minutes at 72° C. The resulting PCR product was designated as Y158p2.

(b-3) The two PCR products (Y158p1 and Y158p2) obtained in (b-1) and (b-2) were mixed and a reaction solution having the composition shown in Table 6 was prepared. PCR was carried out by subjecting the reaction solution to heat treatment for 5 minutes at 98° C., followed by carrying out a reaction, in which 1 cycle consisted of a first step carried out for 10 seconds at 98° C., a second step carried out for 5 seconds at 55° C. and a third step carried out for 1 minute at 72° C., for 5 cycles to obtain PCR product Y158p in which Y158p1 and Y158p2 were linked.

(b-4) PCR was carried out using the PCR product Y158p obtained in (b-3) as template and using oligonucleotides composed of the sequences according to SEQ ID NO: 23 and SEQ ID NO: 24 as PCR primers. After preparing a reaction solution having the composition shown in Table 7, PCR was carried out by subjecting the reaction solution to heat treatment for 5 minutes at 98° C., and carrying out a reaction, in which 1 cycle consisted of a first step carried out for 10 seconds at 98° C., a second step carried out for 5 seconds at 55° C. and a third step carried out for 1 minute at 72° C., for 30 cycles. As a result, a polynucleotide was obtained that encoded Fc-binding protein in which 158th amino acid of an Fc-binding protein (FcR24) was substituted with a random amino acid. The resulting polynucleotide was designated as Y158p3.

(b-5) After purifying the polynucleotide obtained in (b-4), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(b-6) The resulting transformant was cultured in LB medium containing 50 μg/mL of kanamycin.

When plasmid was extracted from the harvested bacterial cells (transformant) and the nucleotide sequence of the sequence of the polynucleotide region was analyzed according to the method described in section (5) of Example 1, transformants were obtained in which Tyr158 of Fc-binding protein FcR24 (histidine at position in SEQ ID NO: 89) was substituted with Ala, Arg, Asn, Cys, Gln, Glu, Gly, Ile, Leu, Lys, Met, Phe, Pro, Ser, Thr, Trp, Tyr or Val.

Example 32 Evaluation of Amino Acid Substituents of Thr140 or Tyr158

(1) The transformants expressing Fc-binding protein produced in Example 31 were cultured according to the method described in sections (1) to (4) of Example 8 followed by extraction of protein.

(2) The antibody binding activity of the Fc-binding protein in the protein extract prepared in (1) was measured using the ELISA procedure described in section (4) of Example 3. At this time, concentrations were measured by preparing a calibration curve using purified and quantified FcR24.

(3) After diluting each of the Fc-binding proteins to a concentration of 10 μg/mL with pure water, 50 μL of the aforementioned diluted solutions and 50 μL of 300 mM aqueous sodium hydroxide solution (case of amino acid substituents of Thr140) or 350 mM aqueous sodium hydroxide solution (case of amino acid substituents of Tyr158) were mixed to subject to alkaline treatment by allowing to stand undisturbed for 2 hours at 30° C. Subsequently, the solutions were neutralized by adding four volumes of 1 M Tris-HCl buffer (pH 7.0) followed by measuring antibody binding activity of the Fc-binding proteins according to the ELISA method described in section (4) of Example 3.

(4) Alkaline stability was evaluated by calculating residual activity by dividing antibody binding activity in the case of having undergone alkaline treatment by antibody binding activity in the case of having not undergone alkaline treatment.

The results are shown in Table 20 (results for amino acid substituents of Thr140) and Table 21 (results for amino acid substituents of Tyr158). Furthermore, the results for Ile in Table 20 and the results for His in Table 21 indicate the results for FcR24. In the case of Thr140 (Table 20), alkaline stability was confirmed to improve by substituting with Ala, Arg, Ile, Leu, Lys, Phe, Ser or Val, while in the case of Tyr158 (Table 21), alkaline stability was confirmed to improve by substituting with Cys, His, Ile, Leu, Lys, Phe, Trp or Val.

TABLE 20

| Amino Acid Substitution | Residual Activity (%) |
|---|---|
| Ala | 12.9 |
| Arg | 14.8 |
| Ile | 22.4 |
| Gly | 2.5 |
| Leu | 33.6 |
| Lys | 26.5 |
| Phe | 30.5 |
| Ser | 8.0 |
| Val | 23.2 |
| Thr | 4.3 |

TABLE 21

| Amino Acid Substitution | Residual Activity (%) |
|---|---|
| Ala | 1.7 |
| Arg | 2.7 |
| Asn | 3.4 |
| Cys | 8.4 |
| Gln | 3.4 |
| Glu | 2.2 |
| Gly | 2.1 |
| His | 29.2 |
| Ile | 32.4 |
| Leu | 21.9 |
| Lys | 8.4 |
| Met | 4.8 |
| Phe | 15.7 |
| Pro | 1.3 |
| Ser | 1.6 |
| Thr | 3.8 |
| Trp | 29.5 |
| Val | 45.5 |
| Tyr | 5.5 |

Example 33 Preparation of Fc-Binding Protein-Immobilized Gel (1) A ligand that is immobilized on an insoluble support was prepared by culturing the transformant obtained by transforming *Escherichia coli* with a plasmid containing a polynucleotide encoding human Fc-binding protein composed of the amino acid sequence according to SEQ ID NO: 60, and purifying the aforementioned Fc-binding protein from the resulting bacterial cells. Furthermore, the human Fc-binding protein composed of the amino acid sequence according to SEQ ID NO: 60 is a protein having the amino acid substitutions of (a) to (d) indicated below in a human Fc-binding protein composed of the amino acid sequence according to SEQ ID NO: 58:

(a) phenylalanine at position 45 of SEQ ID NO: 58 is substituted with isoleucine, (b) glutamine at position 64 of SEQ ID NO: 58 is substituted with arginine, (c) valine at position 133 of SEQ ID NO: 58 is substituted with glutamic acid, and (d) phenylalanine at position 187 of SEQ ID NO: 58 is substituted with serine.

(2) A vinyl polymer gel activated by iodoacetyl groups was obtained by subjecting hydroxyl groups of vinyl polymer gel (particle diameter: 10 μm, Tosoh) to functional group transformation in accordance with ordinary methods.

(3) A human Fc-binding protein-immobilized gel was produced by reacting the ligand prepared in (1) with the resulting activated gel.

(4) The resulting gel was packed into a stainless steel column measuring 4.6 mm in diameter×75 mm to prepare a separation column.

Comparative Example 1 Separation of Monoclonal Antibodies (1) Commercially available monoclonal antibodies (Rituxan, Zenyaku Kogyo) were prepared to a concentration of 1 mg/mL with phosphate buffered saline (PBS) and used as a monoclonal antibody solution.

(2) After equilibrating the separation column prepared in Example 1 with 20 mM sodium acetate buffer solution (pH 5.0) (Buffer A), 5 μL of the monoclonal antibody solution prepared in (1) were added thereto.

(3) Buffer A was passed through the column for 2 minutes after having added the monoclonal antibody solution, and monoclonal antibodies added to the column were separated and eluted according to a gradient ranging from 100% Buffer A/0% 10 mM glycine-HCl buffer solution (pH 3.0) (Buffer B) to 0% Buffer A/100% Buffer B for 2 minutes to 40 minutes thereafter. The eluted monoclonal antibodies were detected with a UV detector (absorbance: 280 nm).

Figure 7:
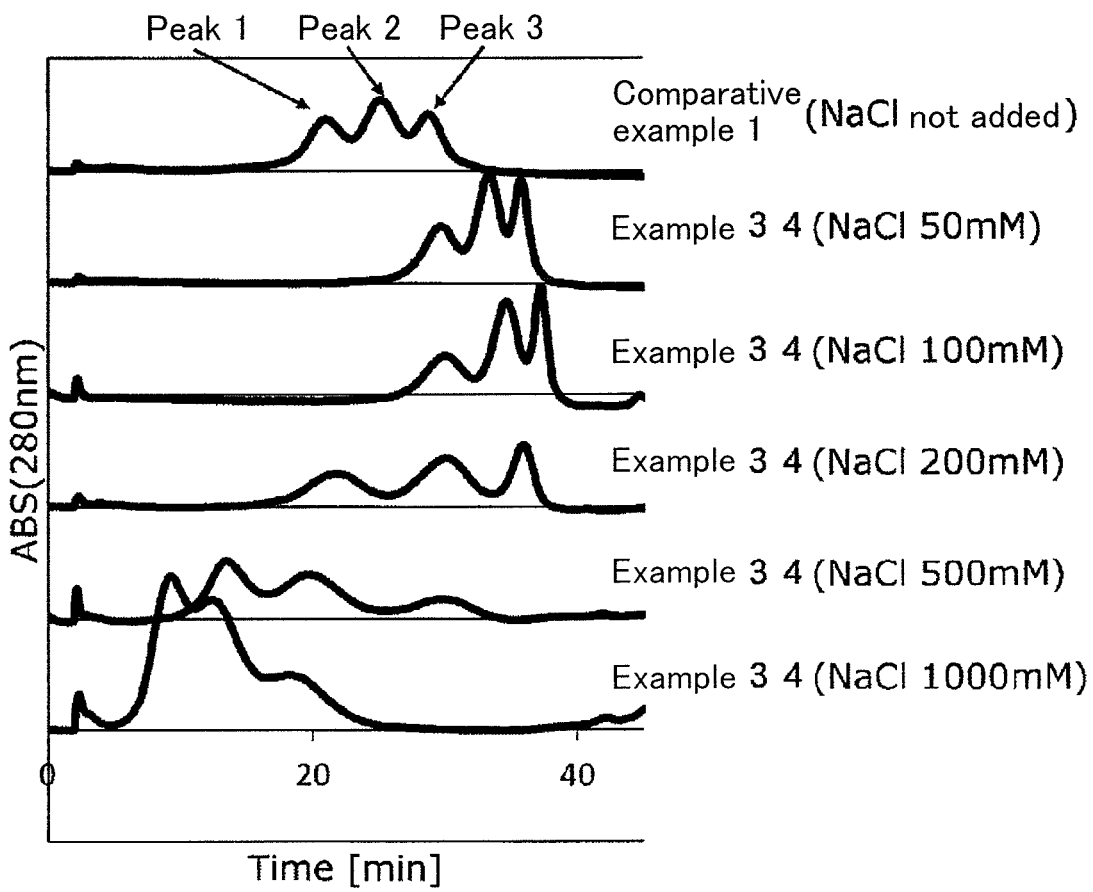
FIG. 7 is a chromatograph obtained by separating monoclonal antibodies using buffer solution (equilibration solution) to which sodium chloride had been added or not added.

The results (chromatogram) of separating the monoclonal antibodies are shown in FIG. 7. Three large peaks were detected that were designated Peak 1, Peak 2 and Peak 3 in order starting with the peak having the earliest elution time. In addition, when the resolution (Rs value) of each peak was calculated according to the equation indicated below, the resolution between Peak 1 and Peak 2 was 0.63 and the resolution between Peak 2 and Peak 3 was 0.61.

Rs value=1.18×(elution time of peak having late elution time−elution time of peak having early elution time)/(half width value of peak having early elution time+half width value of peak having late elution time)

Example 34 Separation of Monoclonal Antibodies According to Present Invention (Part 1)

An experiment was carried out in the same manner as Comparative Example 1 with the exception of using 20 mM sodium acetate buffer solution (pH 5.0) containing 50 mM, 100 mM, 200 mM, 500 mM or 1000 mM sodium chloride for the Buffer A. The results are shown in FIG. 7. The peaks were designated Peak 1, Peak 2 and Peak 3 in order starting with the peak having the early elution time, and when Rs values were calculated using the same method as Comparative Example 1, the results shown in Table 22 were obtained. The addition of sodium chloride (chloride ion) to the 20 mM sodium acetate buffer solution (pH 5.0) was determined to improve Rs values between Peak 1 and Peak 2 and/or Rs values between Peak 2 and Peak 3. In the case of the buffer solutions to which sodium chloride (chloride ion) was added at 50 mM to 500 mM in particular, Rs values between Peak 1 and Peak 2 and Rs values between Peak 2 and Peak 3 both improved, thereby making these particularly preferable.

TABLE 22

| Concentration of | Rs Value | |
|---|---|---|
| Added NaCl (mM) | Peak 1-Peak 2 | Peak 2-Peak 3 |
| 0 | 0.63 | 0.61 |
| 50 | 0.77 | 0.79 |
| 100 | 0.92 | 0.88 |
| 200 | 1.01 | 1.05 |
| 500 | 0.73 | 1.08 |
| 1000 | 0.41 | 0.63 |

Example 35 Separation of Monoclonal Antibodies According to Present Invention (Part 2)

Figure 8:
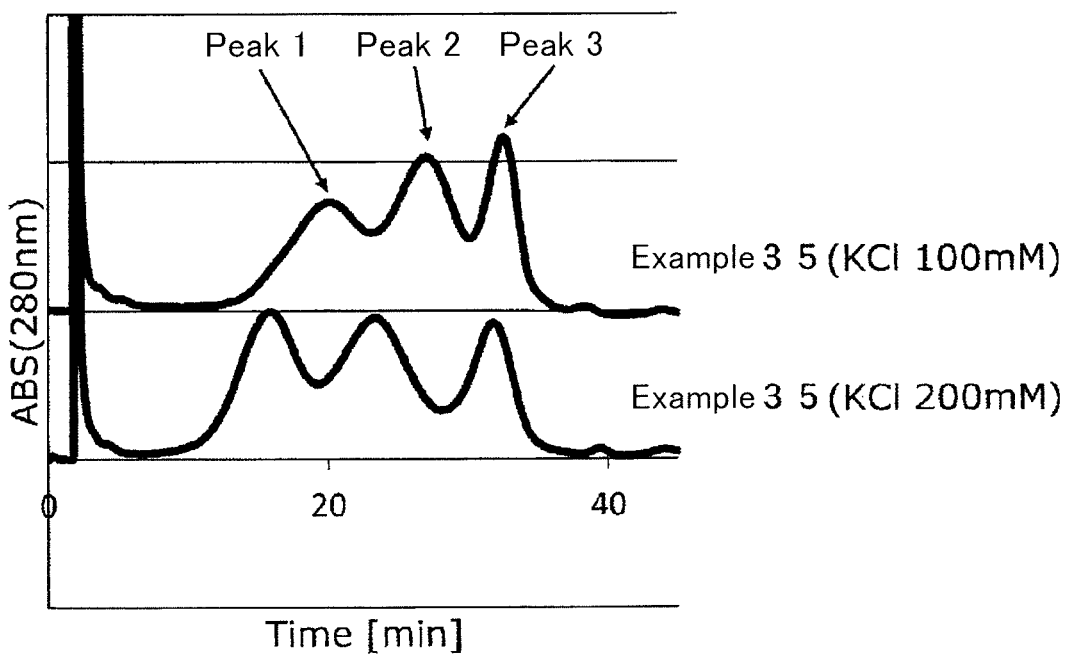
FIG. 8 is a chromatograph obtained by separating monoclonal antibodies using a buffer solution (equilibration solution) to which potassium chloride had been added.

An experiment was carried out in the same manner as Comparative Example 1 with the exception of using 20 mM sodium acetate buffer solution (pH 5.0) containing 100 mM or 200 mM potassium chloride for the Buffer A. The results are shown in FIG. 8. The peaks were designated Peak 1, Peak 2 and Peak 3 in order starting with the peak having the early elution time, and when Rs values were calculated using the same method as Comparative Example 1, the results shown in Table 23 were obtained. On the basis of these results, Rs values between Peak 1 and Peak 2 and/or Rs values between Peak 2 and Peak 3 were determined to improve in the same manner as the results of Example 34 even if potassium chloride is used instead of sodium chloride.

TABLE 23

| Concentration of | Rs Value | |
|---|---|---|
| Added KCl (mM) | Peak 1-Peak 2 | Peak 2-Peak 3 |
| 0 | 0.63 | 0.61 |
| 100 | 0.59 | 0.74 |
| 200 | 0.69 | 0.93 |

Example 36 Separation of Monoclonal Antibodies According to Present Invention (Part 3)

Figure 9:
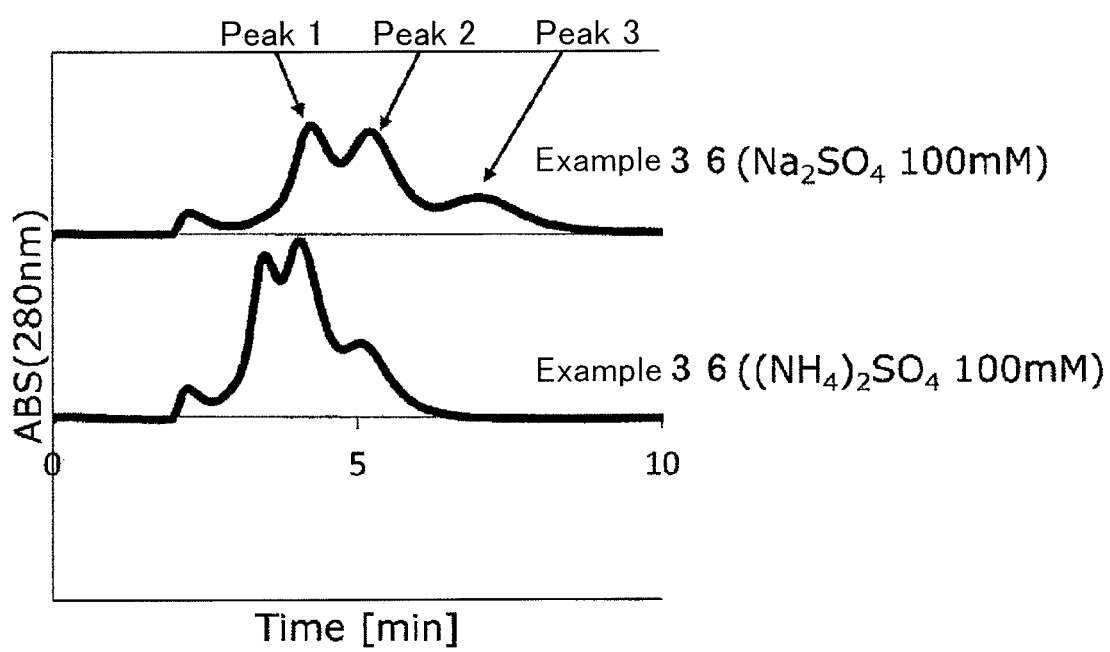
FIG. 9 is a chromatograph obtained by separating monoclonal antibodies using a buffer solution (equilibration solution) to which sodium sulfate and ammonium sulfate had been added.

An experiment was carried out in the same manner as Comparative Example 1 with the exception of using 20 mM sodium acetate buffer solution (pH 5.0) containing 100 mM sodium sulfate or 100 mM ammonium sulfate for the Buffer A. The results are shown in FIG. 9. The peaks were designated Peak 1, Peak 2 and Peak 3 in order starting with the peak having the early elution time, and when Rs values were calculated using the same method as Comparative Example 1, the results shown in Table 24 were obtained. On the basis of these results, Rs values between Peak 1 and Peak 2 or Rs values between Peak 2 and Peak 3 were determined to improve in the same manner as the results of Example 34 even if sulfate ion is used instead of chloride ion.

TABLE 24

| Concentration of | Rs Value | |
|---|---|---|
| Added Sulfate | Peak 1-Peak 2 | Peak 2-Peak 3 |
| None | 0.63 | 0.61 |
| $Na_2SO_4$ 100 mM | 0.62 | 0.78 |
| $(NH_4)_2SO_4$ 100 mM | 0.69 | 0.61 |

Example 37 Construction of Fc-Binding Protein Having Single Amino Acid Substitution Fc binding proteins in which valine (Val) at position 27, tyrosine (Tyr) at position 35 and glutamic acid (Glu) at position 121 in SEQ ID NO: 1, among those amino acid substitutions clearly determined in Example 3 to be involved in improving the stability of Fc-binding protein, were substituted with other amino acids were produced according to each of the methods indicated below.

(A) Construction of Fc-Binding Protein in which Valine (Val) at Position 27 of SEQ ID NO: 1 is Substituted with Other Amino Acids (A-1) PCR was carried out using the same method as section (a-1) of Example 4 with the exception of using the pET-eFcR constructed in Example 1 as template and using oligonucleotides composed of the sequences according to SEQ ID NO: 24 and SEQ ID NO: 95 (5'-CTGC-CGAAAGCGNNKGTGTTTCTGGAACCG-3') as PCR primers. The purified PCR product was designated as 27 pF.

(A-2) PCR was carried out using the same method as section (a-1) of Example 4 with the exception of using the pET-eFcR constructed in Example 1 as template and using oligonucleotides composed of the sequences according to SEQ ID NO: 23 and SEQ ID NO: 96 (5'-TTCCA-GAAACACMNNCGCTTTCGGCAGATC-3') as PCR primers. The purified PCR product was designated as 27pR.

(A-3) After mixing the two PCR products (27 pF and 27pR) obtained in (A-1) and (A-2), PCR was carried out in the same manner as section (a-3) of Example 4 to link 27 pF and 27pR. The resulting PCR product was designated as 27p.

(A-4) PCR was carried out using the same method as section (a-4) of Example 4 by using the PCR product 27p obtained in (A-3) as template and using oligonucleotides composed of the sequences according to SEQ ID NO: 23 and SEQ ID NO: 24 as PCR primers. As a result, a polynucleotide was produced that encoded an Fc-binding protein in which valine at position 27 of SEQ ID NO: 1 was substituted with a random amino acid.

(A-5) After purifying the polynucleotide obtained in (A-4), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(A-6) The resulting transformant was cultured in LB medium containing 50 μg/mL of kanamycin. Plasmid was extracted from the harvested bacterial cells (transformant) and the nucleotide sequence was analyzed using the same method as section (5) of Example 1.

As a result, a polynucleotide was obtained that encoded Fc-binding protein having the amino acid substitution of Val27Gly (V27G), Val27Lys (V27K), Val27Thr (V27T), Val27Ala (V27A), Val27Trp (V27W) or Val27Arg (V27R).

(B) Construction of Fc-Binding Protein in which Tyrosine (Tyr) at Position 35 of SEQ ID NO: 1 is Substituted with Other Amino Acids (B-1) PCR was carried out using the same method as section (a-1) of Example 4 with the exception of using the pET-eFcR constructed in Example 1 as template and using oligonucleotides composed of the sequences according to SEQ ID NO: 24 and SEQ ID NO: 97 (5'-AACCGCAGTG-GNNKCGCGTGCTGGAGAAAG-3') as PCR primers. The purified PCR product was designated as 35 pF.

(B-2) PCR was carried out using the same method as section (a-1) of Example 4 with the exception of using the pET-eFcR constructed in Example 1 as template and using oligonucleotides composed of the sequences according to SEQ ID NO: 23 and SEQ ID NO: 98 (5'-AGCACGCG-MNNCCACTGCGGTTCCAGAAAC-3') as PCR primers. The purified PCR product was designated as 35pR.

(B-3) After mixing the two PCR products (35 pF and 35pR) obtained in (B-1) and (B-2), PCR was carried out in the same manner as section (a-3) of Example 4 to link 35 pF and 35pR. The resulting PCR product was designated as 35p.

(B-4) PCR was carried out using the same method as section (a-4) of Example 4 by using the PCR product 35p obtained in (B-3) as template and using oligonucleotides composed of the sequences according to SEQ ID NO: 23 and SEQ ID NO: 24 as PCR primers. As a result, a polynucleotide was constructed that encoded an Fc-binding protein in which tyrosine at position 35 of SEQ ID NO: 1 was substituted with a random amino acid.

(B-5) After purifying the polynucleotide obtained in (B-4), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(B-6) The resulting transformant was cultured in LB medium containing 50 μg/mL of kanamycin. Plasmid was extracted from the harvested bacterial cells (transformant) and the nucleotide sequence was analyzed using the same method as section (5) of Example 1.

As a result, a polynucleotide was obtained that encoded Fc-binding protein having the amino acid substitution of Tyr35Cys (Y35C), Tyr35Asp (Y35D), Tyr35Phe (Y35F), Tyr35Gly (Y35G), Tyr35Lys (Y35K), Tyr35Leu (Y35L), Tyr35Asn (Y35N), Tyr35Pro (Y35P), Tyr35Arg (Y35R), Tyr35Ser (Y35S), Tyr35Thr (Y35T), Tyr35Val (Y35V) or Tyr35Trp (Y35W).

(C) Construction of Fc-Binding Protein in which Glutamic Acid (Glu) at Position 121 of SEQ ID NO: 1 is Substituted with Other Amino Acids (C-1) PCR was carried out using the same method as section (a-1) of Example 4 with the exception of using the pET-eFcR constructed in Example 1 as template and using oligonucleotides composed of the sequences according to SEQ ID NO: 24 and SEQ ID NO: 99 (5'-GTGT-TCAAAGAGNNKGATCCGATTCATCTG-3') as PCR primers. The purified PCR product was designated as 121 pF.

(C-2) PCR was carried out using the same method as section (a-1) of Example 4 with the exception of using the pET-eFcR constructed in Example 1 as template and using oligonucleotides composed of the sequences according to SEQ ID NO: 23 and SEQ ID NO: 100 (5'-AATCGGATC-MNNCTCTTTGAACACCCACCG-3') as PCR primers. The purified PCR product was designated as 121pR.

(C-3) After mixing the two PCR products (121 pF and 121pR) obtained in (C-1) and (C-2), PCR was carried out in the same manner as section (a-3) of Example 4 to link 121 pF and 121pR. The resulting PCR product was designated as 121p.

(C-4) PCR was carried out using the same method as section (a-4) of Example 4 by using the PCR product 121p obtained in (C-3) as template and using oligonucleotides composed of the sequences according to SEQ ID NO: 23 and SEQ ID NO: 24 as PCR primers. As a result, a polynucleotide was constructed that encoded an Fc-binding protein in which glutamic acid at position 121 of SEQ ID NO: 1 was substituted with a random amino acid.

(C-5) After purifying the polynucleotide obtained in (C-4), the polynucleotide was digested with restriction enzymes NcoI and HindIII and ligated to expression vector pETMalE preliminarily digested with restriction enzymes NcoI and HindIII (Japanese Unexamined Patent Publication No. 2011-206046), followed by using this expression vector to transform *Escherichia coli* strain BL21(DE3).

(C-6) The resulting transformant was cultured in LB medium containing 50 μg/mL of kanamycin. Plasmid was extracted from the harvested bacterial cells (transformant) and the nucleotide sequence was analyzed using the same method as section (5) of Example 1.

As a result, a polynucleotide was obtained that encoded Fc-binding protein having the amino acid substitution of Glu121Lys (E121K), Glu121Pro (E121P), Glu121Arg (E121R), Glu121Gly (E121G), Glu121His (E121H) or Glu121Val (E121V).

Example 38 Evaluation of Antibody Binding Activity of Fc-Binding Protein Having Single Amino Acid Substitution (1) Transformants expressing the wild-type Fc-binding protein prepared in Example 1 and the Fc-binding proteins having a single amino acid substitution prepared in Example 37 were each cultured using the same method as sections (1) and (2) of Example 3 to express wild-type Fc-binding protein and Fc-binding proteins having a single amino acid substitution.

(2) Antibody binding activity was investigated for the expressed Fc-binding proteins having a single amino acid substitution according to the ELISA procedure described in sections (3) and (4) of Example 3.

Figure 10:
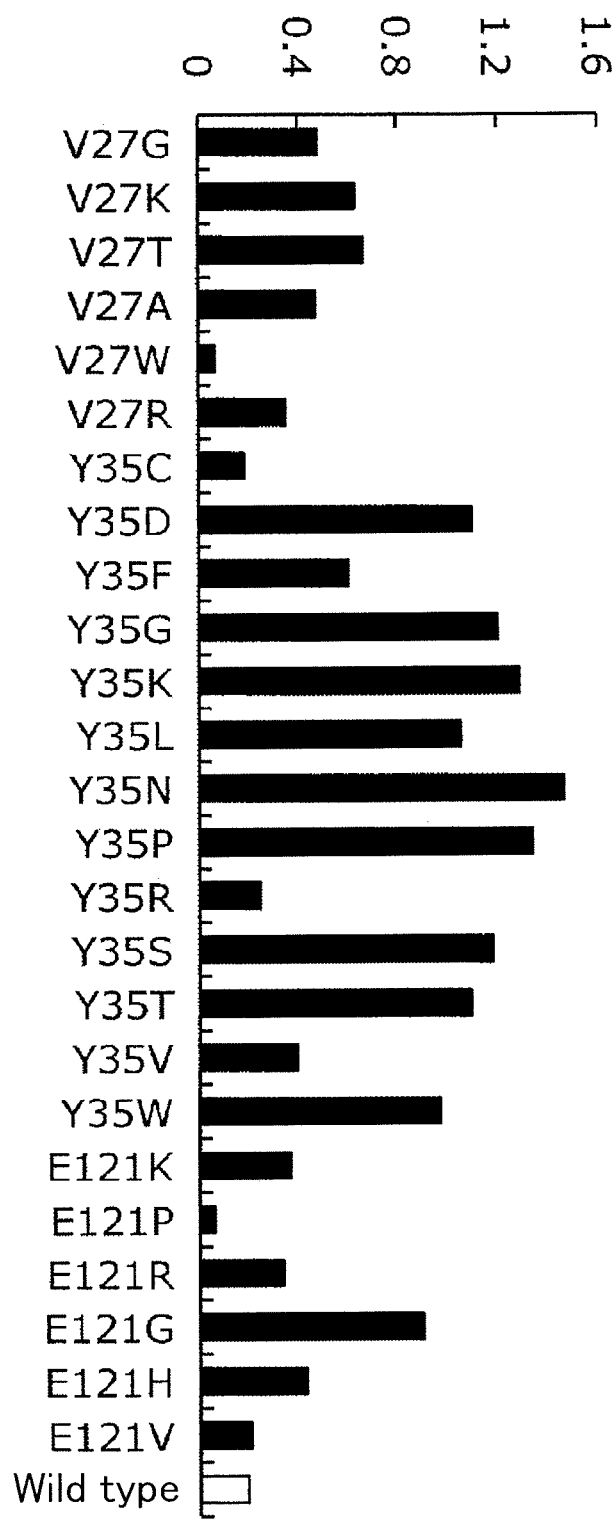
FIG. 10 is a drawing indicating the results of evaluating antibody binding activity of Fc-binding proteins containing amino acid substitutions. In the drawing, the wild type indicates Fc-binding protein not containing an amino acid substitution.

The results are shown in FIG. 10. Antibody binding activity improved in comparison with the wild-type Fc-binding protein as a result of substituting valine at position 27 of SEQ ID NO: 1 with glycine (V27G), lysine (V27K), threonine (V27T), alanine (V27A) and arginine (V27R). On the other hand, antibody binding activity decreased in comparison with the wild-type Fc-binding protein when Val at position 27 of SEQ ID NO: 1 was substituted with tryptophan (V27W).

Antibody binding activity improved in comparison with the wild-type Fc-binding protein as a result of substituting tyrosine at position 35 of SEQ ID NO: 1 with aspartic acid (Y35D), phenylalanine (Y35F), glycine (Y35G), lysine (Y35K), leucine (Y35L), asparagine (Y35N), proline (Y35P), serine (Y35S), threonine (Y35T), valine (Y35V) and tryptophan (Y35W). Among these, Y35D, Y35G, Y35K, Y35L, Y35N, Y35P, Y35S, Y35T and Y35W demonstrated considerably improved antibody binding activity in comparison with the wild-type Fc-binding protein. On the other hand, in the case of having substituted tyrosine at position 35 of SEQ ID NO: 1 with cysteine (Y35C) or arginine (Y35R), antibody binding activity was roughly equal to that of the wild-type Fc-binding protein.

Antibody binding activity improved in comparison with the wild-type Fc-binding protein as a result of substituting glutamic acid at position 121 of SEQ ID NO: 1 with lysine (E121K), arginine (E121R), glycine (E121G) and histidine (E121H). Among these, E121G demonstrated considerably improved antibody binding activity in comparison with the wild-type Fc-binding protein. On the other hand, in the case of having substituted glutamic acid at position 121 of SEQ ID NO: 1 with valine (E121V), antibody binding activity was roughly equal to that of the wild-type Fc-binding protein, and in the case of substituting with proline (E121P), antibody binding activity decreased in comparison with the wild-type Fc-binding protein.

Example 39 Construction of Fc-Binding Protein Expression Vector

A polynucleotide encoding a signal peptide, in which proline (P) at position 6 of the PelB signal peptide according to SEQ ID NO: 101 (MKYLLPTAAAGLLLLAAQPAMA) was substituted with serine (S), was inserted into expression vector pTrc99a to construct an expression vector containing a signal peptide.

(1) Equal volumes of oligonucleotides composed of the sequences according to SEQ ID NO: 102 (5'-CATGAAATACCTGCTGTCGACCGCTGCTGCTGGTCTGCTG CTCCTCGCTGCCCAGCCGGCGATGGC-3') and SEQ ID NO: 103 (5'-CATGGCC ATCGCCGGCTGGGCAGCGAGGAGCAGCAGACCAGCAGCAGCGGTC-GACAGCAGGTAT TT-3') were mixed, and after heating for 5 minutes at 95° C., the temperature was lowered at the rate of 1° C. per minute followed by holding at 15° C. when the mixture reached that temperature to construct a double-stranded oligonucleotide.

(2) The double-stranded oligonucleotide constructed in (1) was ligated to expression vector pTrc99a preliminarily treated with restriction enzyme NcoI, followed by using this expression vector to transform *Escherichia coli* strain JM109 (Takara Bio).

(3) After culturing the resulting transformant in LB medium containing 100 μg/mL of carbenicillin, expression vector pTrc-PelBV3 was obtained using the QIAprep Spin Miniprep Kit (Qiagen).

Example 40 Preparation of Fc-Binding Protein with Added Cysteine Tag (FcRCys)

(1) PCR was carried out using the pET-eFcR constructed in Example 1 as template. The primers used in this PCR consisted of oligonucleotides composed of the sequences according to SEQ ID NO: 21 and SEQ ID NO: 57 (5'-CCCAAGCTTATCCGCAGG TATCGTTGCGGCACCCT-TGGGTAATGGTAATATTCACGGTCTCGCTGC-3'). After preparing a reaction solution having the composition shown in Table 2 and subjecting the reaction solution to heat treatment for 5 minutes at 98° C., a reaction, in which 1 cycle consisted of a first step carried out for 10 seconds at 98° C., a second step carried out for 5 seconds at 55° C. and a third step carried out for 1 minute at 72° C., was repeated for 30 cycles.

(2) After purifying the polynucleotide obtained in (1) and digesting with restriction enzymes NcoI and HindIII, the polynucleotide was ligated to the expression vector pTrc-PelBV3 constructed in Example 39 after preliminarily digesting with restriction enzymes NcoI and HindIII, and the ligation product was used to transform *Escherichia coli* strain W3110.

(3) After culturing the resulting transformant in LB medium containing 100 μg/mL of carbenicillin, expression vector pTrc-eFcRCys was obtained using the QIAprep Spin Miniprep Kit (Qiagen).

(4) The nucleotide sequence of pTrc-eFcRCys was analyzed using the same method as section (5) of Example 1 with the exception of using oligonucleotides composed of the sequences according to SEQ ID NO: 104 (5'-TGTGG-TATGGCTGTGCAGG-3') and SEQ ID NO: 105 (5'-TCG-GCATGGGGTCAGGTG-3') as sequence primers.

The amino acid sequence of the polypeptide expressed with expression vector pTrc-eFcRCys is shown in SEQ ID NO: 106, and the sequence of the polynucleotide encoding that polypeptide is shown in SEQ ID NO: 107. Furthermore, in SEQ ID NO: 107, the sequence from methionine (Met) at position 1 to alanine (Ala) at position 22 constitutes a PelB signal peptide in which proline at position 6 is substituted with serine, the sequence from glycine (Gly) at position 24 to glutamine (Gln) at position 199 constitutes the amino acid sequence of the Fc-binding protein (corresponding to the region from position 17 to position 192 of SEQ ID NO: 1), and the sequence from glycine (Gly) at position the 200 to glycine (Gly) at position 207 constitutes a cysteine tag sequence.

Example 41 Preparation of FcRCys (1) The transformant expressing FcRCys constructed in Example 40 was inoculated into 400 mL of 2YT liquid medium (peptone: 16 g/L, yeast extract: 10 g/L, sodium chloride: 5 g/L) containing 100 μg/mL of carbenicillin contained in a 2 L baffled flask followed by pre-culturing by shake culturing aerobically overnight at 37° C.

(2) 180 mL of the culture broth of (1) were inoculated into 1.8 L of liquid medium containing 10 g/L of glucose, 20 g/L of yeast extract, 3 g/L of trisodium phosphate dodecahydrate, 9 g/L of disodium hydrogen phosphate dodecahydrate, 1 g/L of ammonium chloride and 50 mg/L of kanamycin sulfate followed by final culturing using a 3 L fermenter (Biott). Final culturing was begun by setting to conditions consisting of a temperature of 30° C., pH of 6.9 to 7.1, ventilation rate of 1 VVM, and dissolved oxygen concentration of 30% of saturated concentration. The pH was controlled by using acid in the form of 50% phosphoric acid and base in the form of 14% aqueous ammonia, dissolved oxygen was controlled by changing the stirring speed, and the stirring speed was set to a lower limit of 500 rpm and upper limit of 1000 rpm. Following the start of culturing, feed medium (248.9 g/L of glucose, 83.3 g/L of yeast extract and 7.2 g/L of magnesium sulfate heptahydrate) was added while controlling according to the level of dissolved oxygen (DO) at the point glucose concentration was no longer able to be measured.

(3) The culturing temperature was lowered to 25° C. by using the time when optical absorbance at 600 nm (OD600) reached about 150 as an indicator of the number of bacterial cells, and after confirming that the culturing temperature had reached the set temperature, IPTG was added to a final concentration of 0.5 mM followed by continuing culturing at 25° C.

(4) Culturing was discontinued about 48 hours after the start of culturing, and the culture broth was centrifuged for 20 minutes at 4° C. and 8000 rpm to harvest the bacterial cells.

(5) The harvested cells were suspended in 20 mM Tris-HCl buffer (pH 7.0) at 5 mL/1 g (cells) followed by disrupting the cells using an ultrasonic generator (Insonator 201M (trade name), Kubota) at 4° C. for about 10 minutes at an output of about 150 W. The disrupted cell suspension was centrifuged twice for 20 minutes at 4° C. and 8000 rpm followed by collection of the supernatant.

(6) The supernatant obtained in (5) was applied to a VL32×250 column (Merck Millipore) packed with 140 mL of ToyoPearl CM-650M (Tosoh) preliminarily equilibrated with 20 mM phosphate buffer solution (8 mM sodium dihydrogen phosphate, 12 mM disodium hydrogen phosphate) (pH 7.0) at a flow rate of 5 mL/min. After washing with the buffer solution used for equilibration, the column was eluted with 20 mM phosphate buffer solution (pH 7.0) containing 0.5 M sodium chloride.

(7) The eluate obtained in (6) was applied to an XK26/20 column (GE Healthcare) packed with 90 mL of IgG Sepharose (GE Healthcare) preliminarily equilibrated with 20 mM Tris-HCl buffer (pH 7.4) containing 150 mM sodium chloride. After washing with the buffer solution used for equilibration, the column was eluted with 0.1 M glycine-HCl buffer (pH 3.0). Furthermore, the pH of the eluate was returned to the vicinity of neutrality by adding 1 M Tris-HCl buffer (pH 8.0) at one-fourth the amount of eluate.

About 12 mg of highly pure FcRCys was obtained as a result of the aforementioned purification.

Example 42 Preparation of Fc-Binding Protein (FcR)-Immobilized Gel and Antibody Separation (1) After activating hydroxyl groups on the surface of 2 mL of a hydrophilic vinyl polymer for use as a separating agent (TOYOPEARL, Tosoh) with iodoacetyl groups, a gel having FcR immobilized thereon was obtained by reacting 4 mg of the FcRCys prepared in Example 41.

(2) 0.5 mL of the FcR-immobilized gel prepared in (1) was packed into a stainless steel column measuring 4.6 mm in diameter×75 mm to prepare an FcR column.

(3) The FcR column prepared in (2) was connected to a high-performance chromatography system (Tosoh) and equilibrated with 20 mM acetate buffer solution (pH 4.5).

(4) 0.15 mL of monoclonal antibodies (Rituxan, Zenyaku Kogyo) diluted to 4.0 mg/mL with phosphate buffered saline (PBS) (pH 7.4) were applied to the column at a flow rate of 0.3 mL/min.

(5) After washing the column with equilibration buffer for 2 minutes while maintaining the flow rate at 0.3 mL/min, adsorbed monoclonal antibodies were eluted at a pH gradient generated with 10 mM glycine-HCl buffer (pH 3.0) (gradient at which 100% of the 10 mM glycine-HCl buffer (pH 3.0) elutes in 38 minutes).

Figure 11:
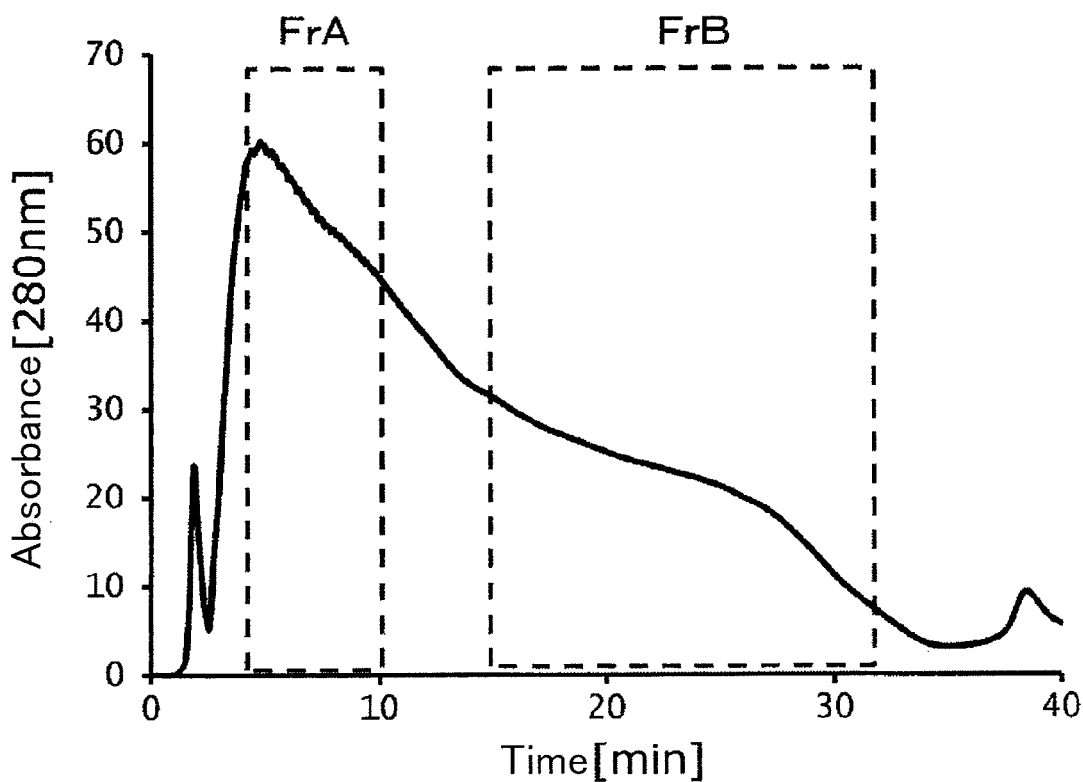
FIG. 11 is a drawing indicating the elution pattern of an antibody using FcR-immobilized gel. FrA and FrB in the drawing indicate the positions of Fraction A and Fraction B, respectively.

The results (elution pattern) are shown in FIG. 11. As a result of interacting with FcR, the monoclonal antibodies were separated into multiple peaks instead of a single peak in the manner of gel filtration chromatography.

Example 43 Measurement of Antibody-Dependent Cell-Medicated Cytotoxicity (ADCC) Activity of Antibodies Separated with FcR-Immobilized Gel (1) The monoclonal antibodies that eluted under the conditions described in Example 42 were separated and fractionated into regions consisting of Fraction A (FrA) and Fraction B (FrB) in the elution pattern indicated in FIG. 11.

(2) The buffer solution was exchanged with phosphate buffered saline (PBS, 10 mM disodium hydrogen phosphate, 1.76 mM potassium dihydrogen phosphate, 137 mM sodium chloride, 2.7 mM potassium chloride, pH 7.4) while concentrating the fractionated FrA and FrB with an ultrafiltration membrane (Merck Millipore).

(3) The concentrations of antibodies contained in the FrA and FrB subjected to concentration and buffer exchange and monoclonal antibodies prior to separation were measured at an optical absorbance of 280 nm.

(4) The ADCC activities of antibodies contained in FrA and FrB and the monoclonal antibodies prior to separation were measured according to the method indicated below.

(4-1) An 8-step dilution series was prepared at dilution factor of ⅓ from 3 µg/mL of the antibodies contained in FrA and FrB and the monoclonal antibodies prior to separation using ADCC assay buffer prepared by mixing 1.4 mL of low IgG serum and 33.6 mL of RPMI1640 medium.

(4-2) Raji cells were prepared to a concentration of about $5 \times 10^5$ cells/mL with ADCC assay buffer and added to a 96-well plate (3917, Corning) at 25 µL/well.

(4-3) The Fraction A, Fraction B and monoclonal antibodies prior to separation prepared in (2) along with a blank (ADCC assay buffer only) were added to the wells containing Raji cells at 25 µL/well.

(4-4) Effector cells (Promega) were prepared at a concentration of about $3.0 \times 10^5$ cells/mL with ADCC assay buffer and added to the wells containing Raji cells and antibodies at 25 µL/well. Subsequently, the plate was allowed to stand undisturbed for 6 hours in a $CO_2$ incubator (5% $CO_2$, 37° C.)

(4-5) After allowing the 96-well plate to stand undisturbed for 5 minutes to 30 minutes at room temperature, Luciferase Assay Reagent (Promega) was added at 75 µL/well. After allowing to react for 30 minutes at room temperature, luminescence was measured with the GloMax Multi Detection System (Promega).

Figure 12:
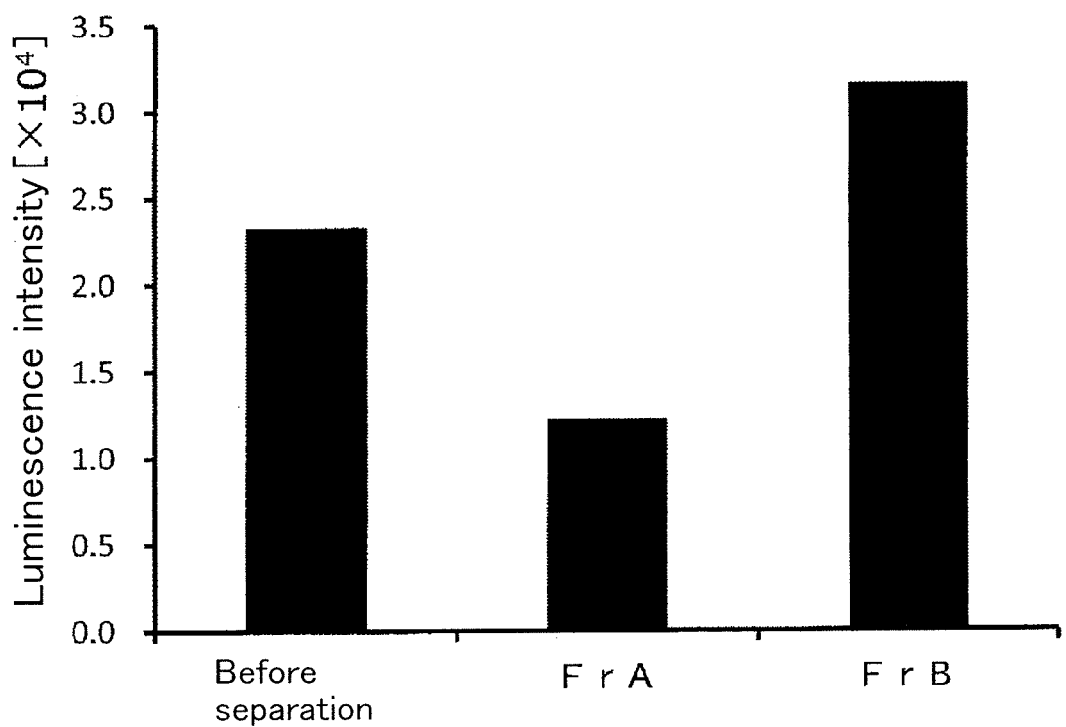
FIG. 12 is a drawing indicating the results of measuring the ADCC activity of antibody separated with FcR-immobilized gel.

The results of comparing the luminescence intensities of the FrA and FrB, fractionated under the elution conditions described in Example 42, and the monoclonal antibodies prior to separation are shown in FIG. 12. Furthermore, the results of FIG. 12 indicate values obtained by subtracting the luminescence intensity of the blank from the measured luminescence intensity, and higher luminescence intensity indicates greater ADCC activity.

Although luminescence intensity of FrA decreased in comparison with that of the monoclonal antibodies prior to separation, the luminescence intensity of FrB improved by about 1.4 times. In other words, FrB was identified to demonstrate higher ADCC activity in comparison with the monoclonal antibodies prior to separation and FrA. In addition, since antibodies demonstrating potent ADCC activity are contained in the fraction (FrB) that eluted late from the FcR-immobilized gel (or in other words, had a long column retention time), the FcR-immobilized gel was identified to be able to separate antibodies based on the degree of ADCC activity.

Furthermore, the entire contents of the specifications, sequence listings, claims, drawings and abstracts of Japanese Patent Application No. 2014-133181 filed on Jun. 27, 2014, Japanese Patent Application No. 2014-147206 filed on Jul. 17, 2014, Japanese Patent Application No. 2014-147207 filed on Jul. 17, 2014, Japanese Patent Application No. 2014-263407 filed on Dec. 25, 2014, Japanese Patent Application No. 2015-047462 filed on Mar. 10, 2015 and Japanese Patent Application No. 2015-115078 filed on Jun. 5, 2015 are cited herein, and are incorporated as disclosures of the specification of the present invention.

The invention claimed is:

1. An Fc-binding protein, comprising the amino acid residues from position 33 to position 208 of the amino acid sequence according to SEQ ID NO: 37, wherein the Fc-binding protein is introduced with one of the following (1) to (14) amino acid substitutions in the amino acid residues from position 33 to position 208:

(1) valine at position 133 of SEQ ID NO: 37 is substituted with glutamic acid, (2) phenylalanine at position 45 of SEQ ID NO: 37 is substituted with isoleucine and valine at position 133 of SEQ ID NO: 37 is substituted with glutamic acid, (3) phenylalanine at position 187 of SEQ ID NO: 37 is substituted with serine, (4) glutamine at position 64 of SEQ ID NO: 37 is substituted with arginine, (5) aspartic acid at position 98 of SEQ ID NO: 37 is substituted with glutamic acid, (6) glutamine at position 128 of SEQ ID NO: 37 is substituted with leucine, (7) lysine at position 135 of SEQ ID NO: 37 is substituted with asparagine, (8) leucine at position 158 of SEQ ID NO: 37 is substituted with glutamine, (9) asparagine at position 196 of SEQ ID NO: 37 is substituted with serine,

(10) isoleucine at position 204 of SEQ ID NO: 37 is substituted with valine,

(11) tyrosine at position 67 of SEQ ID NO: 37 is substituted with serine and glutamine at position 106 of SEQ ID NO: 37 is substituted with arginine,

(12) phenylalanine at position 77 of SEQ ID NO: 37 is substituted with tyrosine, lysine at position 135 of SEQ ID NO: 37 is substituted with glutamic acid, and leucine at position 191 of SEQ ID NO: 37 is substituted with arginine,

(13) phenylalanine at position 45 of SEQ ID NO: 37 is substituted with leucine, glutamic acid at position 55 of SEQ ID NO: 37 is substituted with glycine, aspartic acid at position 93 of SEQ ID NO: 37 is substituted with glycine, and threonine at position 156 of SEQ ID NO: 37 is substituted with isoleucine, and

(14) phenylalanine at position 45 of SEQ ID NO: 37 is substituted with isoleucine, glutamine at position 64 of SEQ ID NO: 37 is substituted with arginine, valine at position 133 of SEQ ID NO: 37 is substituted with glutamic acid, and phenylalanine at position 187 of SEQ ID NO: 37 is substituted with serine, wherein the Fc-binding protein has improved heat stability compared to an Fc-binding protein comprising the amino acid residues from position 33 to position 208 of the amino acid sequence according to SEQ ID NO: 37.

2. The Fc-binding protein according to claim 1, wherein at least one amino acid substitution of the following (73) to (76) is further introduced into the Fc-binding protein):

(73) leucine at position 82 of SEQ ID NO: 37 is substituted with histidine or arginine,

(74) glycine at position 163 of SEQ ID NO: 37 is substituted with aspartic acid,

(75) tyrosine at position 174 of SEQ ID NO: 37 is substituted with histidine, and

(76) valine at position 192 of SEQ ID NO: 37 is substituted with phenylalanine.

3. An adsorbent comprising the Fc-binding protein according to claim 1 and an insoluble support, the Fc-binding protein being immobilized on the insoluble support.

4. A polynucleotide encoding the Fc-binding protein according to claim 2.

5. An expression vector containing the polynucleotide according to claim 4.

6. A transformant comprising a host and the expression vector according to claim 5, the host expressing the expression vector.

7. The transformant according to claim 6, wherein the host is *Escherichia coli*.

8. A method for producing an Fc-binding protein, comprising expressing an Fc-binding protein by culturing the transformant according to claim 6; and recovering the expressed Fc-binding protein from the culture.

* * * * *

UNITED STATES PATENT AND TRADEMARK OFFICE
CERTIFICATE OF CORRECTION

PATENT NO. : 10,815,289 B2
APPLICATION NO. : 15/321916
DATED : October 27, 2020
INVENTOR(S) : Y. Asaoka et al.

It is certified that error appears in the above-identified patent and that said Letters Patent is hereby corrected as shown below:

In the Claims

At Column 146, Line 57 (Claim 3, Line 2) please change "claim 1" to -- claim 2 --.

Signed and Sealed this
Eighth Day of December, 2020

Andrei Iancu
*Director of the United States Patent and Trademark Office*